US010738015B2

(12) United States Patent
Ratcliffe et al.

(10) Patent No.: US 10,738,015 B2
(45) Date of Patent: Aug. 11, 2020

(54) 1,3-DIAZA-SPIRO-[3.4]-OCTANE DERIVATIVES

(71) Applicant: GRÜNENTHAL GMBH, Aachen (DE)

(72) Inventors: Paul Ratcliffe, Aachen (DE); Ingo Konetzki, Aachen (DE); Nikolay Sitnikov, Aachen (DE); Thomas Koch, Stolberg (DE); Ruth Jostock, Stolberg (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 16/554,847

(22) Filed: Aug. 29, 2019

(65) Prior Publication Data
US 2019/0382355 A1 Dec. 19, 2019

Related U.S. Application Data

(63) Continuation of application No. 16/033,446, filed on Jul. 12, 2018, now abandoned.

(30) Foreign Application Priority Data

Jul. 12, 2017 (EP) .................................... 17020299

(51) Int. Cl.
| C07D 235/02 | (2006.01) |
| C07D 401/04 | (2006.01) |
| C07D 401/14 | (2006.01) |
| C07D 403/04 | (2006.01) |
| C07D 405/06 | (2006.01) |
| C07D 405/14 | (2006.01) |
| A61P 25/00 | (2006.01) |
| C07D 401/06 | (2006.01) |
| C07D 413/10 | (2006.01) |
| C07D 413/14 | (2006.01) |
| C07D 417/06 | (2006.01) |

(52) U.S. Cl.
CPC ............ *C07D 235/02* (2013.01); *A61P 25/00* (2018.01); *C07D 401/04* (2013.01); *C07D 401/06* (2013.01); *C07D 401/14* (2013.01); *C07D 403/04* (2013.01); *C07D 405/06* (2013.01); *C07D 405/14* (2013.01); *C07D 413/10* (2013.01); *C07D 413/14* (2013.01); *C07D 417/06* (2013.01)

(58) Field of Classification Search
CPC .. C07D 235/02; C07D 401/04; C07D 401/14; C07D 403/04; C07D 405/06; C07D 405/14
See application file for complete search history.

(56) References Cited

U.S. PATENT DOCUMENTS

| 6,878,732 B2 * | 4/2005 | Wrobleski | .......... | C07C 43/1747 514/385 |
| 2006/0004034 A1 | 1/2006 | Hinze et al. | | |
| 2009/0247530 A1 | 10/2009 | Nolte et al. | | |
| 2012/0029006 A1 | 2/2012 | Linz et al. | | |
| 2017/0101420 A1 | 4/2017 | Virgili-Bernado et al. | | |

FOREIGN PATENT DOCUMENTS

| WO | 2004-043967 A1 | 5/2004 |
| WO | 2009-118168 A1 | 10/2009 |
| WO | 2012-013343 A1 | 2/2012 |
| WO | 2015/192039 A1 | 12/2015 |

OTHER PUBLICATIONS

Cheng et al., Relationship Between the Inhibition Constant ((K,) and the Concentration of Inhibitor Which Causes 50 Percent Inhibitor ((I50 of an Enzymatic Reaction*) 1973, pp. 3099-3108.
Fiedler, 2002, Cover, Table of Contents.
Gupta et al., "A Systematic Review of the Peripheral Analgesic Effects of Intraarticular Morphine"; Anesth Analg. 2001, 93: pp. 761-770.
Jenck et al., "Orphanin FQ Acts as an Anxiolytic to Attenuate Behavioral Responses to Stress"; Proc. Natl. Acad. Sci. USA, vol. 94, 1997, pp. 14854-14858.
Kalso et al., "No pain, no gain: Clinical Excellence and Scientific Rigour—Lessons learned from IA Morphine"; Pain, vol. 98, (2002) pp. 269-275.
Mabrouk et al., "Stimulation of O Opioid Receptor and Blockade of Nociceptin/Orphanin FQ Receptor Synergistically Attenuate Parkinsonism"; The Journal of Neuroscience, Sep. 24, 2014, 34(39), pp. 12953-12962.
Pradhan et al.,"The delta opioid receptor: an evolving target for the treatment of brain disorders", Pharm. Sci. vol. 32, No. 10, 2011, pp. 581-590.
Schroeder et al., "Functional Plasticity of the N/OFQ—NOOP receptor system determines analgesic properties of NOP receptor agonists", Br. J. Pharmacology, 2014; 171, pp. 3777-3800.
Stein et al., "Attacking Pain at its source: New Persepective on Opioids"; Natural Medicine, vol. 9, No. 8, Aug. 2003, pp. 1003-1008.
Witkin et al., "The biology of Nociceptin/Orphanin FQ (N/OFQ) related to obesity, stress, anxiety, mood, and drug dependence", Pharmacology & Therapeutics, 141, (2014) pp. 283-299.
Zoellner et al., "Topical Fentanyl in a Randomized, Double-blind Study in Patients With Corneal Damage", Clin. J. Pain, vol. 24, No. 8, Oct. 2008, pp. 690-696.
European Search Report corresponds to EP Application No. 17020299.8 dated Nov. 13, 2017.

* cited by examiner

*Primary Examiner* — Laura L Stockton

(74) *Attorney, Agent, or Firm* — Norris McLaughlin, P.A.

(57) ABSTRACT

The invention relates to 1,3-diaza-spiro-[3.4]-octane derivatives, their preparation and use in medicine, particularly in various neurological disorders, including but not limited to pain, neurodegenerative disorders, neuroinflammatory disorders, neuropsychiatric disorders, substance abuse/dependence.

21 Claims, No Drawings

1,3-DIAZA-SPIRO-[3.4]-OCTANE DERIVATIVES

This application is a continuation of U.S. Nonprovisional application Ser. No. 16/033,446, filed Jul. 12, 2018, which claims priority of European Patent Application No. 17020299.8, filed Jul. 12, 2017, the contents of which are incorporated herein by reference.

The invention relates to 1,3-diaza-spiro-[3.4]-octane derivatives, their preparation and use in medicine, particularly in various neurological disorders, including but not limited to pain, neurodegenerative disorders, neuroinflammatory disorders, neuropsychiatric disorders, substance abuse/dependence.

Opioid receptors are a group of Gi/o protein-coupled receptors which are widely distributed in the human body. The opioid receptors are currently subdivided into four major classes, i.e. the three classical opioid receptors mu-opioid (MOP) receptor, kappa-opioid (KOP) receptor, and delta-opioid (DOP) receptor as well as the opioid receptor-like (ORL-1) receptor, which was more recently discovered based on its high homology with said classical opioid receptors. After identification of the endogenous ligand of the ORL-1 receptor, known as nociceptin/orphanin FQ, a highly basic 17 amino acid peptide isolated from tissue extracts in 1995, the ORL-1 receptor was renamed "nociceptin opioid peptide receptor" and abbreviated as "NOP-receptor".

The classical opioid receptors (MOP, KOP and DOP) as well as the NOP receptor are widely distributed/expressed in the human body, including in the brain, the spinal cord, on peripheral sensory neurons and the intestinal tract, wherein the distribution pattern differs between the different receptor classes.

Nociceptin acts at the molecular and cellular level in very much the same way as opioids. However, its pharmacological effects sometimes differ from, and even oppose those of opioids. NOP-receptor activation translates into a complex pharmacology of pain modulation, which, depending on route of administration, pain model and species involved, leads to either pronociceptive or antinociceptive activity. Furthermore, the NOP receptor system is upregulated under conditions of chronic pain. Systemic administration of selective NOP receptor agonists was found to exert a potent and efficacious analgesia in non-human primate models of acute and inflammatory pain in the absence of side effects. The activation of NOP receptors has been demonstrated to be devoid of reinforcing effects but to inhibit opioid-mediated reward in rodents and non-human primates (Review: Schroeder et al, Br J Pharmacol 2014; 171 (16): 3777-3800, and references therein).

Besides the involvement of the NOP receptor in nociception, results from preclinical experiments suggest that NOP receptor agonists might be useful inter alia in the treatment of neuropsychiatric disorders (Witkin et al, Pharmacology & Therapeutics, 141 (2014) 283-299; Jenck et al., Proc. Nall. Acad. Sci. USA 94, 1997, 14854-14858). Remarkably, the DOP receptor is also implicated to modulate not only pain but also neuropsychiatric disorders (Mabrouk et al, 2014; Pradhan et al., 2011).

Strong opioids acting at the MOP receptor site are widely used to treat moderate to severe acute and chronic pain. However, the therapeutic window of strong opioids is limited by severe side effects such as nausea and vomiting, constipation, dizziness, somnolence, respiratory depression, physical dependence and abuse. Furthermore, it is known that MOP receptor agonists show only reduced effectiveness under conditions of chronic and neuropathic pain.

It is known that some of the above mentioned side-effects of strong opioids are mediated by activation of classic opioid-receptors within the central nervous system. Furthermore, peripheral opioid receptors, when activated, can inhibit transmission of nociceptive signals shown in both, clinical and animal studies (Gupta et al., 2001; Kalso et al., 2002; Stein et al., 2003; Zollner et al., 2008).

Thus, to avoid CNS-mediated adverse effects after systemic administration, one approach has been to provide peripherally restricted opioid receptor ligands that do not easily cross the blood-brain barrier and therefore distribute poorly to the central nervous system (see for instance WO 2015/192039). Such peripherally acting compounds might combine effective analgesia with limited side-effects.

Another approach has been to provide compounds which interact with both the NOP receptor and the MOP receptor. Such compounds have for instance been described in WO 2004/043967, WO 2012/013343 and WO 2009/118168.

A further approach has been to provide multi-opioid receptor analgesics that modulate more than one of the opioid receptor subtypes to provide additive or synergistic analgesia and/or reduced side effects like abuse liability or tolerance.

On the one hand, it would be desirable to provide analgesics that selectively act on the NOP receptor system but less pronounced on the classic opioid receptor system, especially MOP receptor system, whereas it would be desirable to distinguish between central nervous activity and peripheral nervous activity. On the other hand, it would be desirable to provide analgesics that act on the NOP receptor system and also to a balanced degree on the MOP receptor system, whereas it would be desirable to distinguish between central nervous activity and peripheral nervous activity.

There is a need for medicaments which are effective in the treatment of pain and which have advantages compared to the compounds of the prior art. Where possible, such medicaments should contain such a small dose of active ingredient that satisfactory pain therapy can be ensured without the occurrence of intolerable treatment-emergent adverse events.

It is an object of the invention to provide pharmacologically active compounds, preferably analgesics that have advantages compared to the prior art.

This object has been achieved by the subject-matter of the patent claims.

A first aspect of the invention relates to 1,3-diaza-spino-[3.4]-octane derivatives according to general formula (I)

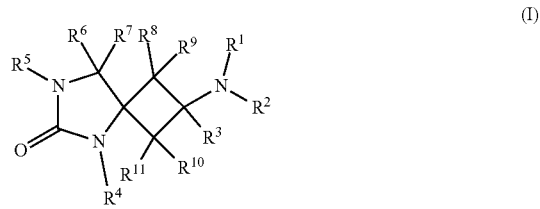

wherein
$R^1$ and $R^2$ independently of one another mean
—H;
—$C_1$-$C_6$-alkyl, linear or branched, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$;

a 3-12-membered cycloalkyl moiety, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$; wherein said 3-12-membered cycloalkyl moiety is optionally connected through —C$_1$-C$_6$-alkylene-, linear or branched, saturated or unsaturated, unsubstituted; or a 3-12-membered heterocycloalkyl moiety, saturated or unsaturated, unsubstituted or substituted with one, two, three or four substituents independently of one another selected from the group consisting of —F, —Cl, —Br, —OH, —OCH$_3$, —CN and —CO$_2$CH$_3$; wherein said 3-12-membered heterocycloalkyl moiety is optionally connected through —C$_1$-C$_6$-alkylene-, linear or branched, saturated or unsaturated, unsubstituted;

or

R$^1$ and R$^2$ together with the nitrogen atom to which they are attached form a ring and mean —(CH$_2$)$_{3-6}$—; —(CH$_2$)$_2$—O—(CH$_2$)$_2$—; or —(CH$_2$)$_2$—NR$^A$—(CH$_2$)$_2$—, wherein R$^A$ means —H or —C$_1$-C$_6$-alkyl, linear or branched, saturated or unsaturated, unsubstituted or substituted with one, two, three or four substituents independently of one another selected from the group consisting of —F, —Cl, —Br and —I;

preferably with the proviso that R$^1$ and R$^2$ do not simultaneously mean —H;

R$^3$ means

—C$_1$-C$_6$-alkyl, linear or branched, saturated or unsaturated, unsubstituted, mono- or polysubstituted;

a 3-12-membered cycloalkyl moiety, saturated or unsaturated, unsubstituted, mono- or polysubstituted; wherein said 3-12-membered cycloalkyl moiety is optionally connected through —C$_1$-C$_6$-alkylene-, linear or branched, saturated or unsaturated, unsubstituted, mono- or polysubstituted;

a 3-12-membered heterocycloalkyl moiety, saturated or unsaturated, unsubstituted, mono- or polysubstituted; wherein said 3-12-membered heterocycloalkyl moiety is optionally connected through —C$_1$-C$_6$-alkylene-, linear or branched, saturated or unsaturated, unsubstituted, mono- or polysubstituted;

a 6-14-membered aryl moiety, unsubstituted, mono- or polysubstituted; wherein said 6-14-membered aryl moiety is optionally connected through —C$_1$-C$_6$-alkylene-, linear or branched, saturated or unsaturated, unsubstituted, mono- or polysubstituted; or a 5-14-membered heteroaryl moiety, unsubstituted, mono- or polysubstituted; wherein said 5-14-membered heteroaryl moiety is optionally connected through —C$_1$-C$_6$-alkylene-, linear or branched, saturated or unsaturated, unsubstituted, mono- or polysubstituted;

R$^4$ means

—H;

C$_1$-C$_6$-alkyl, linear or branched, saturated or unsaturated, unsubstituted, mono- or polysubstituted; wherein said —C$_1$-C$_6$-alkyl is optionally connected through —C(=O)—, —C(=O)O—, or —S(=O)$_2$—;

a 3-12-membered cycloalkyl moiety, saturated or unsaturated, unsubstituted, mono- or polysubstituted; wherein said 3-12-membered cycloalkyl moiety is optionally connected through —C$_1$-C$_6$-alkylene-, linear or branched, saturated or unsaturated, unsubstituted, mono- or polysubstituted; or wherein said 3-12-membered cycloalkyl moiety is optionally connected through —C(=O)—, —C(=O)O—, —C(=O)O—CH$_2$—, or —S(=O)$_2$—;

a 3-12-membered heterocycloalkyl moiety, saturated or unsaturated, unsubstituted, mono- or polysubstituted; wherein said 3-12-membered heterocycloalkyl moiety is optionally connected through —C$_1$-C$_6$-alkylene-, linear or branched, saturated or unsaturated, unsubstituted, mono- or polysubstituted; or wherein said 3-12-membered heterocycloalkyl moiety is optionally connected through —C(=O)—, —C(=O)O—, —C(=O)O—CH$_2$—, or —S(=O)$_2$—;

a 6-14-membered aryl moiety, unsubstituted, mono- or polysubstituted; wherein said 6-14-membered aryl moiety is optionally connected through —C$_1$-C$_6$-alkylene-, linear or branched, saturated or unsaturated, unsubstituted, mono- or polysubstituted; or wherein said 6-14-membered aryl moiety is optionally connected through —C(=O)—, —C(=O)O—, —C(=O)O—CH$_2$—, or —S(=O)$_2$—; or a 5-14-membered heteroaryl moiety, unsubstituted, mono- or polysubstituted; wherein said 5-14-membered heteroaryl moiety is optionally connected through —C(=O)—, —C(=O)O—, —C(=O)O—CH$_2$—, or —S(=O)$_2$—;

R$^5$ means

—H;

—C$_1$-C$_6$-alkyl, linear or branched, saturated or unsaturated, unsubstituted, mono- or polysubstituted; wherein said —C$_1$-C$_6$-alkyl is optionally connected through —C(=O)—, —C(=O)O—, or —S(=O)$_2$—;

a 3-12-membered cycloalkyl moiety, saturated or unsaturated, unsubstituted, mono- or polysubstituted; wherein said 3-12-membered cycloalkyl moiety is optionally connected through —C$_1$-C$_6$-alkylene-, linear or branched, saturated or unsaturated, unsubstituted, mono- or polysubstituted; or wherein said 3-12-membered cycloalkyl moiety is optionally connected through —C(=O)—, —C(=O)O—, —C(=O)O—CH$_2$—, or —S(=O)$_2$—;

a 3-12-membered heterocycloalkyl moiety, saturated or unsaturated, unsubstituted, mono- or polysubstituted; wherein said 3-12-membered heterocycloalkyl moiety is optionally connected through —C$_1$-C$_6$-alkylene-, linear or branched, saturated or unsaturated, unsubstituted, mono- or polysubstituted; or wherein said 3-12-membered heterocycloalkyl moiety is optionally connected through —C(=O)—, —C(=O)O—, —C(=O)O—CH$_2$—, or —S(=O)$_2$—;

a 6-14-membered aryl moiety, unsubstituted, mono- or polysubstituted; wherein said 6-14-membered aryl moiety is optionally connected through —C$_1$-C$_6$-alkylene-, linear or branched, saturated or unsaturated, unsubstituted, mono- or polysubstituted; or wherein said 6-14-membered aryl moiety is optionally connected through —C(=O)—, —C(=O)O—, —C(=O)O—CH$_2$—, or —S(=O)$_2$—; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted; or wherein said 5-14-membered heteroaryl moiety is optionally connected through —C(=O)—, —C(=O)O—, —C(=O)O—$CH_2$—, or —S(=O)$_2$—;

$R^6$, $R^7$, $R^8$, $R^9$, $R^{10}$, and $R^{11}$ independently of one another mean —H, —F, —Cl, —Br, —I, —OH, or —$C_1$-$C_6$-alkyl, linear or branched, saturated or unsaturated, unsubstituted, mono- or polysubstituted;

or $R^6$ and $R^7$ together mean =O;

wherein "mono- or polysubstituted" means that one or more hydrogen atoms are replaced by a substituent independently of one another selected from the group consisting of —F, —Cl, —Br, —I, —CN, —$R^{12}$, —C(=O)$R^{12}$, —C(=O)O$R^{12}$, —C(=O)N$R^{12}R^{13}$, —O—($CH_2CH_2$—O)$_{1-30}$—H, —O—($CH_2CH_2$—O)$_{1-30}$—$CH_3$, =O, —O$R^{12}$, —OC(=O)$R^{12}$, —OC(=O)O$R^{12}$, —OC(=O)N$R^{12}R^{13}$, —$NO_2$, —N$R^{12}R^{13}$, —N$R^{12}$—($CH_2$)$_{1-6}$—C(=O)$R^{13}$, —N$R^{12}$—($CH_2$)$_{1-6}$—C(=O)O$R^{13}$, —N$R^{14}$—($CH_2$)$_{1-6}$—C(=O)N$R^{12}R^{13}$, —N$R^{12}$C(=O)$R^{13}$, —N$R^{12}$C(=O)—O$R^{13}$, —N$R^{14}$C(=O)N$R^{12}R^{13}$, —N$R^{12}$S(=O)$_2R^{13}$, —S$R^{12}$, —S(=O)$R^{12}$, —S(=O)$_2R^{12}$, —S(=O)$_2$O$R^{12}$, and —S(=O)$_2$N$R^{12}R^{13}$;

wherein $R^{12}$, $R^{13}$ and $R^{14}$ independently of one another mean

—H;

—$C_1$-$C_6$-alkyl, linear or branched, saturated or unsaturated, unsubstituted or substituted with one, two, three or four substituents independently of one another selected from the group consisting of —F, —Cl, —Br, —I, —CN, =O, —OH, —$NH_2$, —NH—$C_1$-$C_6$-alkyl, —N($C_1$-$C_6$-alkyl)$_2$, —$C_1$-$C_6$-alkyl, —O—$C_1$-$C_6$-alkyl, —C(=O)OH, —C(=O)O$C_1$-$C_4$-alkyl, —C(=O)$NH_2$, —C(=O)NH—$C_1$-$C_6$-alkyl, —C(=O)N($C_1$-$C_6$-alkyl)$_2$, —S—$C_1$-$C_6$-alkyl, —S(=O)—$C_1$-$C_6$-alkyl and —S(=O)$_2$—$C_1$-$C_6$-alkyl;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, =O, —OH, —$NH_2$, —NH—$C_1$-$C_6$-alkyl, —N($C_1$-$C_6$-alkyl)$_2$, —$C_1$-$C_6$-alkyl, —O—$C_1$-$C_6$-alkyl, —C(=O)OH, —C(=O)O$C_1$-$C_4$-alkyl, —C(=O)$NH_2$, —C(=O)NH—$C_1$-$C_6$-alkyl, —C(=O)N($C_1$-$C_6$-alkyl)$_2$, —S—$C_1$-$C_6$-alkyl, —S(=O)—$C_1$-$C_6$-alkyl and —S(=O)$_2$—$C_1$-$C_6$-alkyl;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, =O, —OH, —$NH_2$, —NH—$C_1$-$C_6$-alkyl, —N($C_1$-$C_6$-alkyl)$_2$, —$C_1$-$C_6$-alkyl, —O—$C_1$-$C_6$-alkyl, —C(=O)OH, —C(=O)O$C_1$-$C_4$-alkyl, —C(=O)$NH_2$, —C(=O)NH—$C_1$-$C_6$-alkyl, —C(=O)N($C_1$-$C_6$-alkyl)$_2$, —S—$C_1$-$C_6$-alkyl, —S(=O)—$C_1$-$C_6$-alkyl and —S(=O)$_2$—$C_1$-$C_6$-alkyl;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, =O, —OH, —$NH_2$, —NH—$C_1$-$C_6$-alkyl, —N($C_1$-$C_6$-alkyl)$_2$, —$C_1$-$C_6$-alkyl, —O—$C_1$-$C_6$-alkyl, —C(=O)OH, —C(=O)O$C_1$-$C_4$-alkyl, —C(=O)$NH_2$, —C(=O)NH—$C_1$-$C_6$-alkyl, —C(=O)N($C_1$-$C_6$-alkyl)$_2$, —S—$C_1$-$C_6$-alkyl, —S(=O)—$C_1$-$C_6$-alkyl and —S(=O)$_2$—$C_1$-$C_6$-alkyl; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, =O, —OH, —$NH_2$, —NH—$C_1$-$C_6$-alkyl, —N($C_1$-$C_6$-alkyl)$_2$, —$C_1$-$C_6$-alkyl, —O—$C_1$-$C_6$-alkyl, —C(=O)OH, —C(=O)O$C_1$-$C_4$-alkyl, —C(=O)$NH_2$, —C(=O)NH—$C_1$-$C_6$-alkyl, —C(=O)N($C_1$-$C_6$-alkyl)$_2$, —S—$C_1$-$C_6$-alkyl, —S(=O)—$C_1$-$C_6$-alkyl and —S(=O)$_2$—$C_1$-$C_6$-alkyl;

or $R^{12}$ and $R^{13}$ within —C(=O)N$R^{12}R^{13}$, —OC(=O)N$R^{12}R^{13}$, —N$R^{12}R^{13}$, —N$R^{14}$—($CH_2$)$_{1-6}$—C(=O)N$R^{12}R^{13}$, —N$R^{14}$C(=O)—N$R^{12}R^{13}$, or —S(=O)$_2$N$R^{12}R^{13}$ together with the nitrogen atom to which they are attached form a ring and mean —($CH_2$)$_{3-6}$—; —($CH_2$)$_2$—O—($CH_2$)$_2$—; or —($CH_2$)$_2$—N$R^B$—($CH_2$)$_2$—, wherein $R^B$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;

or a physiologically acceptable salt thereof.

Preferably, aryl includes but is not limited to phenyl and naphthyl. Preferably, heteroaryl includes but is not limited to -1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, -benzo[c][1,2,5]oxadiazolyl, -imidazo[1,2-a]pyrazinyl, or -1H-pyrrolo[2,3-b]pyridinyl. Preferably, cycloalkyl includes but is not limited to -cyclopropyl, -cyclobutyl, -cyclopentyl and -cyclohexyl. Preferably, heterocycloalkyl includes but is not limited to -aziridinyl, -azetidinyl, -pyrrolidinyl, -piperidinyl, -piperazinyl, -morpholinyl, -sulfamorpholinyl, -oxiridinyl, -oxetanyl, -tetrahydropyranyl, and -pyranyl.

When a moiety is connected through an asymmetric group such as —C(=O)O— or —C(=O)O—$CH_2$—, said asymmetric group may be arranged in either direction. For example, when $R^4$ is connected to the core structure through —C(=O)O—, the arrangement may be either $R^4$—C(=O)O-core or core-C(=O)O—$R^4$.

In a preferred embodiment, $R^6$ and $R^7$ together mean =O such that the five membered ring is a hydantoin; and/or $R^8$, $R^9$, $R^{10}$, and $R^{11}$ independently of one another mean —H, —F, —OH, or —$C_1$-$C_6$-alkyl; preferably —H.

In preferred embodiments of the compound according to the invention, $R^6$, $R^7$, $R^8$, $R^9$, $R^{10}$, and $R^{11}$ independently of one another mean —H, —F, —OH, or —$C_1$-$C_6$-alkyl; preferably —H.

In a preferred embodiment of the compound according to the invention, $R^1$ means —H; and $R^2$ means —$C_1$-$C_6$-alkyl, linear or branched, saturated or unsaturated, unsubstituted, mono- or polysubstituted. Preferably, $R^1$ means —H and $R^2$ means —$CH_3$.

In another preferred embodiment of the compound according to the invention, $R^1$ means —$CH_3$; and $R^2$ means —$C_1$-$C_6$-alkyl, linear or branched, saturated or unsaturated, unsubstituted, mono- or polysubstituted. Preferably, $R^1$ means —$CH_3$ and $R^2$ means —$CH_3$.

In still another preferred embodiment of the compound according to the invention, $R^1$ and $R^2$ together with the nitrogen atom to which they are attached form a ring and mean —$(CH_2)_{3-6}$—. Preferably, $R^1$ and $R^2$ together with the nitrogen atom to which they are attached form a ring and mean —$(CH_2)_3$— or —$(CH_2)_4$—.

In another preferred embodiment,
  means —H or —$CH_3$; and
  —$R^2$ means a 3-12-membered cycloalkyl moiety, saturated or unsaturated, unsubstituted; preferably -cycloalkyl, -cyclobutyl or -cyclopentyl; or $R^2$ means a 3-12-membered heterocycloalkyl moiety, saturated or unsaturated, unsubstituted; preferably -oxetanyl or -tetrahydrofuranyl.

In yet another preferred embodiment,
  means —H or —$CH_3$; and
  —$R^2$ means a 3-12-membered cycloalkyl moiety, saturated or unsaturated, unsubstituted; wherein said 3-12-membered cycloalkyl moiety is connected through —$CH_2$—, unsubstituted; preferably —$CH_2$-cycloalkyl, —$CH_2$— cyclobutyl or —$CH_2$-cyclopentyl; or $R^2$ means a 3-12-membered heterocycloalkyl moiety, saturated or unsaturated, unsubstituted; wherein said 3-12-membered heterocycloalkyl moiety is connected through —$CH_2$—, unsubstituted; preferably —$CH_2$-oxetanyl or —$CH_2$-tetrahydrofuranyl.

In a preferred embodiment of the compound according to the invention, $R^3$ means —$C_1$-$C_6$-alkyl, linear or branched, saturated or unsaturated, unsubstituted, mono- or polysubstituted. Preferably, $R^3$ means —$C_1$-$C_6$-alkyl, linear or branched, saturated or unsaturated, unsubstituted or monosubstituted with —$OCH_3$.

In another preferred embodiment of the compound according to the invention, $R^3$ means a 6-14-membered aryl moiety, unsubstituted, mono- or polysubstituted, optionally connected through —$C_1$-$C_6$-alkylene-, linear or branched, saturated or unsaturated, unsubstituted. In a preferred embodiment, $R^3$ means -phenyl unsubstituted, mono- or polysubstituted. More preferably, $R^3$ means -phenyl unsubstituted, mono-, di- or trisubstituted with —F; —Cl; —Br; —$C_1$-$C_4$-alkyl, preferably —$CH_3$; —$CF_3$; —$CHF_2$; —$CH_2F$; —CN; —OH; —$OC_1$-$C_4$-alkyl, preferably —$OCH_3$; —$OCF_3$ or —$OCH_2OCH_3$; preferably —F. Preferably, $R^3$ means -phenyl unsubstituted or -phenyl monosubstituted with —F. In another preferred embodiment, $R^3$ means -benzyl unsubstituted, mono- or polysubstituted. More preferably, $R^3$ means -benzyl unsubstituted, mono-, di- or trisubstituted with —F; —Cl; —Br; —$C_1$-$C_4$-alkyl, preferably —$CH_3$; —$CF_3$; —$CHF_2$; —$CH_2F$; —CN; —OH; —$OC_1$-$C_4$-alkyl, preferably —$OCH_3$; —$OCF_3$ or —$OCH_2OCH_3$; preferably —F.

In still another preferred embodiment of the compound according to the invention, $R^3$ means a 5-14-membered heteroaryl moiety, unsubstituted, mono- or polysubstituted. Preferably, $R^3$ means -thienyl or -pyridinyl, in each case unsubstituted, mono- or polysubstituted. More preferably, $R^3$ means -thienyl, -pyridinyl, -imidazolyl or benzimidazolyl, in each case unsubstituted, mono-, di- or trisubstituted with —F; —Cl; —Br; —$C_1$-$C_4$-alkyl, preferably —$CH_3$; —$CF_3$; —$CHF_2$; —$CH_2F$; —CN; —OH; —$OC_1$-$C_4$-alkyl, preferably —$OCH_3$; —$OCF_3$ or —$OCH_2OCH_3$; preferably —F.

In a preferred embodiment of the compound according to the invention, $R^4$ means —H.

In another preferred embodiment of the compound according to the invention, $R^4$ means —$C_1$-$C_6$-alkyl, linear or branched, saturated or unsaturated, unsubstituted, mono- or polysubstituted. Preferably, $R^4$ means —$C_1$-$C_6$-alkyl, linear or branched, saturated or unsaturated, unsubstituted or monosubstituted with a substituent selected from the group consisting of —F, —Cl, —Br, —I, —CN, —$CF_3$, —OH, —O—$C_1$-$C_4$-alkyl, —$OCF_3$, —O—$(CH_2CH_2$—O$)_{1-30}$—H, —O—$(CH_2CH_2$—O$)_{1-30}$—$CH_3$, —OC(=O)$C_1$-$C_4$-alkyl, —C(=O)$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)NH$C_1$-$C_4$-alkylene-CN, —C(=O)NH$C_1$-$C_4$-alkylene-O—$C_1$-$C_4$-alkyl, —C(=O)N($C_1$-$C_4$-alkyl)$_2$; —S(=O)$C_1$-$C_4$-alkyl, and —S(=O)$_2C_1$-$C_4$-alkyl; or with —C(=O)$NR^{12}R^{13}$ wherein $R^{12}$ and $R^{13}$ together with the nitrogen atom to which they are attached form a ring and mean —$(CH_2)_{3-6}$—, —$(CH_2)_2$—O—$(CH_2)_2$—, or —$(CH_2)_2$—$NR^B$—$(CH_2)_2$—, wherein $R^B$ means —H or —$C_1$-$C_6$-alkyl; or with —C(=O)NH-3-12-membered cycloalkyl, saturated or unsaturated, unsubstituted or monosubstituted with —F, —Cl, —Br, —I, —CN, or —OH; or with —C(=O)NH—3-12-membered heterocycloalkyl, saturated or unsaturated, unsubstituted or monosubstituted with —F, —Cl, —Br, —I, —CN, or —OH. More preferably, $R^4$ means —$C_1$-$C_6$-alkyl, linear or branched, saturated or unsaturated, unsubstituted or monosubstituted with —O—$C_1$-$C_4$-alkyl or —C(=O)N($C_1$-$C_4$-alkyl)$_2$.

In still another preferred embodiment of the compound according to the invention, $R^4$ means a 3-12-membered cycloalkyl moiety, saturated or unsaturated, unsubstituted, mono- or polysubstituted; wherein the 3-12-membered cycloalkyl moiety is connected through —$C_1$-$C_6$-alkylene-, linear or branched, saturated or unsaturated, unsubstituted, mono- or polysubstituted. Preferably, $R^4$ means a 3-12-membered cycloalkyl moiety, saturated or unsaturated, unsubstituted, mono- or polysubstituted; preferably cyclopropyl or cyclobutyl; wherein said 3-12-membered cycloalkyl moiety is connected through —$CH_2$— or —$CH_2CH_2$—. More preferably, $R^4$ means a 3-12-membered cycloalkyl moiety, saturated or unsaturated, unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(=O)OH, —C(=O)O$C_1$-$C_4$-alkyl, —C(=O)$NH_2$, —C(=O)NHC1-$C_4$-alkyl, —C(=O)N($C_1$-$C_4$-alkyl)$_2$, —S(=O)$C_1$-$C_4$-alkyl and —S(=O)$_2C_1$-$C_4$-alkyl; wherein said 3-12-membered cycloalkyl moiety is connected through —$CH_2$— or —$CH_2CH_2$—. Preferably, $R^4$ means cyclopropyl, optionally monosubstituted with —F or —OH, and connected through —$CH_2$—, or cyclobutyl, optionally monosubstituted with —F or —OH, and connected through —$CH_2$—.

In a preferred embodiment of the compound according to the invention, $R^4$ means a 3-12-membered heterocycloalkyl moiety, saturated or unsaturated, unsubstituted, mono- or polysubstituted; wherein said 3-12-membered heterocycloalkyl moiety is connected through —$C_1$-$C_6$-alkylene-, linear or branched, saturated or unsaturated, unsubstituted, mono- or polysubstituted. Preferably, $R^4$ means a 3-12-membered heterocycloalkyl moiety, saturated or unsaturated, unsubstituted, mono- or polysubstituted; wherein said 3-12-membered heterocycloalkyl moiety is connected through —$CH_2$— or —$CH_2CH_2$—. More preferably, $R^4$ means -oxetanyl, -tetrahydrofuranyl or -tetrahydropyranyl, in each case unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2C_1$-$C_4$-alkyl; wherein said -oxetanyl, -tetrahydrofuranyl or -tetrahydropyranyl is connected through —$CH_2$— or —$CH_2CH_2$—. Preferably, $R^4$ means oxetanyl, optionally monosubstituted with —F, and connected through —$CH_2$—

In yet another preferred embodiment of the compound according to the invention, $R^4$ means a 6-14-membered aryl moiety, unsubstituted, mono- or polysubstituted; wherein said 6-14-membered aryl moiety is connected through —$C_1$-$C_6$-alkylene-, linear or branched, saturated or unsaturated, unsubstituted, mono- or polysubstituted. Preferably, $R^4$ means -phenyl, unsubstituted, mono- or polysubstituted; wherein said -phenyl is connected through —$CH_2$— or —$CH_2CH_2$—. More preferably, $R^4$ means -phenyl, unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2C_1$-$C_4$-alkyl; wherein said -phenyl is connected through —$CH_2$— or —$CH_2CH_2$—.

In a further preferred embodiment of the compound according to the invention, $R^4$ means a 5-14-membered heteroaryl moiety, unsubstituted, mono- or polysubstituted; wherein said 5-14-membered heteroaryl moiety is connected through —$C_1$-$C_6$-alkylene-, linear or branched, saturated or unsaturated, unsubstituted, mono- or polysubstituted. Preferably, $R^4$ means a 5-14-membered heteroaryl moiety, unsubstituted, mono- or polysubstituted; wherein said -phenyl is connected through —$CH_2$— or —$CH_2CH_2$—. More preferably, $R^4$ means -pyridinyl, -pyrimidinyl, -pyrazinyl, or -pyrazolinyl, in each case unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2C_1$-$C_4$-alkyl; wherein said -pyridinyl, -pyrimidinyl, -pyrazinyl, or -pyrazolinyl is connected through —$CH_2$— or —$CH_2CH_2$—.

In a preferred embodiment of the compound according to the invention, $R^5$ means —H.

In another preferred embodiment of the compound according to the invention, $R^5$ means —$C_1$-$C_6$-alkyl, linear or branched, saturated or unsaturated, unsubstituted or substituted with one, two, three or four substituents independently of one another selected from the group consisting of —F, —Cl, —Br, —I, —CN, —OH, —O—$C_1$-$C_4$-alkyl, —O—($CH_2CH_2$—O)$_{1-30}$—H, —O—($CH_2CH_2$—O)$_{1-30}$—$CH_3$, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2C_1$-$C_4$-alkyl. Preferably, $R^5$ means —$C_1$-$C_6$-alkyl, linear or branched, saturated or unsaturated, unsubstituted or monosubstituted with —F, —Cl, —Br, —I, —CN, —OH, —$C_1$-$C_4$-alkyl, —O—($CH_2CH_2$—O)$_{1-30}$—H, —O—($CH_2CH_2$—O)$_{1-30}$—$CH_3$, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl or —S(=O)$_2C_1$-$C_4$-alkyl.

Preferably, $R^5$ is selected from the group consisting of —$CH_2$—C(=O)$NH_2$, —$CH_2CH_2$—S(=O)$_2CH_3$, —$CH_2$C($CH_3$)$_2$O$CH_3$, and —$CH_2CH_2$CN.

In particularly preferred embodiments of the compound according to the invention, $R^5$ means —$C_1$-$C_6$-alkyl-(C=O)NR$^{12}$R$^{13}$, —$C_1$-$C_6$-alkyl-OC(=O)NR$^{12}$R$^{13}$, —$C_1$-$C_6$-alkyl-NR$^{12}$R$^{13}$, —$C_1$-$C_6$-alkyl-NR$^{14}$—(CH$_2$)$_{1-6}$—C(=O)NR$^{12}$R$^{13}$, —$C_1$-$C_6$-alkyl-NR$^{14}$C(=O)—NR$^{12}$R$^{13}$, or —$C_1$-$C_6$-alkyl-S(=O)$_2$NR$^{12}$R$^{13}$; preferably —$C_1$-$C_6$-alkyl-(C=O)NR$^{12}$R$^{13}$; wherein in each case said —$C_1$-$C_6$-alkyl- is linear or branched, saturated or unsaturated, unsubstituted or substituted with one, two, three or four substituents independently of one another selected from the group consisting of —F, —Cl, —Br, —I, —CN, —OH, and —O—$C_1$-$C_4$-alkyl; more preferably $R^5$ means —$CH_2CH_2$—C(=O)NR$^{12}$R$^{13}$, —$CH_2CH(CH_3)$—C(=O)NR$^{12}$R$^{13}$, or —$CH_2$C($CH_3$)$_2$—C(=O)NR$^{12}$R$^{13}$; and wherein in each case R$^{12}$, R$^{13}$ and R$^{14}$ independently of one another mean

—H;

—$C_1$-$C_6$-alkyl, linear or branched, saturated or unsaturated, unsubstituted or substituted with one, two, three or four substituents independently of one another selected from the group consisting of —F, —Cl, —Br, —I, —CN, —OH, —$NH_2$, and —O—$C_1$-$C_6$-alkyl;

a 3-12-membered cycloalkyl moiety, saturated or unsaturated, unsubstituted; wherein said 3-12-membered cycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 3-12-membered heterocycloalkyl moiety, saturated or unsaturated, unsubstituted; wherein said 3-12-membered heterocycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl; or R$^{12}$ and R$^{13}$ within —C(=O)NR$^{12}$R$^{13}$, —OC(=O)NR$^{12}$R$^{13}$, —NR$^{12}$R$^{13}$, —NR$^{14}$—(CH$_2$)$_{1-6}$—C(=O)NR$^{12}$R$^{13}$, —NR$^{14}$C(=O)—NR$^{12}$R$^{13}$, or —S(=O)$_2$NR$^{12}$R$^{13}$ together with the nitrogen atom to which they are attached form a ring and mean —(CH$_2$)$_{3-6}$—; —(CH$_2$)$_2$—O—(CH$_2$)$_2$—; or —(CH$_2$)$_2$—NR$^B$—(CH$_2$)$_2$—, wherein R$^B$ means —H or —$C_1$-$C_6$-alkyl, linear or branched, saturated or unsaturated, unsubstituted or substituted with one, two, three or four substituents independently of one another selected from the group consisting of —F, —Cl, —Br and —I.

In another preferred embodiment of the compound according to the invention, $R^5$ means —$C_1$-$C_6$-alkyl, linear or branched, saturated or unsaturated, monosubstituted with a 3-12-membered heterocycloalkyl moiety, saturated or unsaturated, unsubstituted, mono- or polysubstituted; wherein said 3-12-membered heterocycloalkyl moiety is optionally connected through —C=O—. Preferably, $R^5$ means —$C_1$-$C_6$-alkyl-(C=O)-3-12-membered heterocycloalkyl, saturated or unsaturated, unsubstituted, mono- or polysubstituted. More preferably, $R^5$ means —$CH_2$—(=O)-oxetanyl, —$CH_2$—(=O)-tetrahydrofuranyl, —$CH_2$—(=O)-tetrahydropyranyl, —$CH_2$—(=O)-oxetanyl, —$CH_2$—(=O)-tetrahydrofuranyl, —$CH_2$—(=O)-tetrahydropyranyl, —$CH_2$—(=O)-piperidinyl, —$CH_2$—(=O)-piperazinyl, —$CH_2$—(=O)-morpholinyl, —$CH_2$—(=O)-thiomorpholinyl, —$CH_2$—(=O)-1-oxo-thiomorpholinyl, or —$CH_2$—(=O)-1,1-dioxo-thiomorpholinyl, in each case unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2C_1$-$C_4$-alkyl. Preferably, $R^5$ means oxetanyl, optionally monosubstituted with —F or —OH, and connected through —$CH_2$— or —$CH_2CH_2$—.

In another preferred embodiment of the compound according to the invention, $R^5$ means a 3-12-membered cycloalkyl moiety, saturated or unsaturated, unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —$C_1$-$C_4$-alkyl-OH, —O—($CH_2CH_2$—O)$_{1-30}$—H, —O—($CH_2CH_2$—O)$_{1-30}$—$CH_3$, —C(=O)OH, —C(=O)$C_1$-$C_4$-alkyl, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —$NH_2$, —NH$C_1$-$C_4$-alkyl, N($C_1$-$C_4$-alkyl)$_2$, —NHC(=O)—$C_1$-$C_4$-alkyl, —N($C_1$-$C_4$-alkyl)C(=O)$C_1$-$C_4$-alkyl, —S(=O)$C_1$-$C_4$-alkyl and —S(=O)$_2C_1$-$C_4$-alkyl; wherein said 3-12-membered cycloalkyl moiety is optionally connected through —$C_1$-$C_6$-alkylene-, linear or branched, saturated or unsaturated, unsubstituted. Preferably, $R^5$ means cyclobutyl, optionally monosubstituted with —F or —OH, and connected through —$CH_2$—.

In a preferred embodiment of the compound according to the invention, $R^5$ means a 3-12-membered heterocycloalkyl moiety, saturated or unsaturated, unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —$C_1$-$C_4$-alkyl-OH, —O—($CH_2CH_2$—O)$_{1-30}$—H, —O—($CH_2CH_2$—O)$_{1-30}$—$CH_3$, —C(=O)OH, —C(=O)$C_1$-$C_4$-alkyl, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —$NH_2$, —NH$C_1$-$C_4$-alkyl, N($C_1$-$C_4$-alkyl)$_2$, —NHC(=O)—$C_1$-$C_4$-alkyl, —N($C_1$-$C_4$-alkyl)C(=O)$C_1$-$C_4$-alkyl, —S(=O)$C_1$-$C_4$-alkyl and —S(=O)$_2C_1$-$C_4$-alkyl; wherein said 3-12-membered heterocycloalkyl moiety is optionally connected through —$C_1$-$C_6$-alkylene-, linear or branched, saturated or unsaturated, unsubstituted. Preferably, $R^5$ means -oxetanyl, -tetrahydrofuranyl, -tetrahydropyranyl, -piperidinyl, -piperazinyl, -morpholinyl or -thiomorpholinyl, in each case unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2C_1$-$C_4$-alkyl; wherein said -oxetanyl, -tetrahydrofuranyl, -tetrahydropyranyl, -piperidinyl, -piperazinyl, -morpholinyl or -thiomorpholinyl is connected through —$CH_2$— or —$CH_2CH_2$—.

In a preferred embodiment of the compound according to the invention, $R^5$ means -phenyl, unsubstituted, mono- or polysubstituted; wherein said phenyl is optionally connected through —$C_1$-$C_6$-alkylene-, linear or branched, saturated or unsaturated, unsubstituted, mono- or polysubstituted; or wherein said phenyl is optionally connected through —C(=O)—, —C(=O)O—, —C(=O)O—$CH_2$—, or —S(=O)$_2$—. Preferably, $R^5$ means -phenyl unsubstituted or substituted with one, two, three or four substituents independently of one another selected from the group consisting of —F; —Cl; —Br; —I; —CN; —OH; —$C_1$-$C_4$-alkyl; —C($CH_3$)$_2$OH; —$CF_3$; -3-12-membered cycloalkyl, saturated or unsaturated, unsubstituted, mono- or polysubstituted; preferably -cyclopropyl, saturated, unsubstituted; -3-12-membered heterocycloalkyl, saturated or unsaturated, unsubstituted, mono- or polysubstituted; preferably -pyrrolidinyl, -piperidinyl, -morpholinyl, -piperazinyl, -thiomorpholinyl, or -thiomorpholinyl dioxide, in each case saturated, unsubstituted or monosubstituted with —$C_1$-$C_4$-alkyl; -6-14-membered aryl, unsubstituted, mono- or polysubstituted; preferably -phenyl, unsubstituted; —O—$C_1$-$C_4$-alkyl; —S—$C_1$-$C_4$-alkyl; —C(=O)OH; —C(=O)O—$C_1$-$C_4$-alkyl; —C(=O)$NH_2$; —C(=O)NH$C_1$-$C_4$-alkyl; —C(=O)N($C_1$-$C_4$-alkyl)$_2$; —C(=O)N($C_1$-$C_4$-alkyl)($C_1$-$C_4$-alkyl-OH); —C(=O)NH—($CH_2$)$_{1-3}$-3-12-membered cycloalkyl, saturated or unsaturated, unsubstituted or monosubstituted with —OH; preferably —C(=O)NH—($CH_2$)$_{1-3}$-cyclobutyl, saturated or unsaturated, unsubstituted or monosubstituted with —OH; —C(=O)-3-12-membered heterocycloalkyl, saturated or unsaturated, unsubstituted, mono- or polysubstituted; preferably —C(=O)-morpholinyl, saturated, unsubstituted; —S(=O)$C_1$-$C_4$-alkyl; —S(=O)$_2C_1$-$C_4$-alkyl; and —S(=O)$_2$N($C_1$-$C_4$-alkyl)$_2$; in each case optionally connected through —C(=O)—, —C(=O)O—, —C(=O)O—$CH_2$—, or —S(=O)$_2$—. Preferably, $R^5$ means phenyl or benzyl, in each case unsubstituted or substituted with one, two, or three substituents independently of one another selected from the group consisting of —$CH_3$, —C($CH_3$)$_2$OH, and -morpholinyl.

In another preferred embodiment of the compound according to the invention, $R^5$ means -1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, -benzo[c][1,2,5]oxadiazolyl, -imidazo[1,2-a]pyrazinyl, or -1H-pyrrolo[2,3-b]pyridinyl, in each case unsubstituted, mono- or polysubstituted; preferably -pyrazinyl, -pyridazinyl, -pyridinyl, -pyrimidinyl, or -thienyl, in each case unsubstituted, mono- or polysubstituted; in each case optionally connected through —$C_1$-$C_6$-alkylene-, linear or branched, saturated or unsaturated, unsubstituted, mono- or polysubstituted; or in each case optionally connected through —C(=O)—, —C(=O)O—, —C(=O)O—$CH_2$—, or —S(=O)$_2$—. Preferably, $R^5$ means -pyrazinyl, -pyridazinyl, -pyridinyl, -pyrimidinyl, or -thienyl, in each case unsubstituted or substituted with one, two, three or four substituents independently of one another selected from the group consisting of —F; —Cl; —Br; —I; —CN; —OH; —$C_1$-$C_4$-alkyl; —$CF_3$; -3-12-membered cycloalkyl, saturated or unsaturated, unsubstituted, mono- or polysubstituted; preferably -cyclopropyl, saturated, unsubstituted; -3-12-membered heterocycloalkyl, saturated or unsaturated, unsubstituted, mono- or polysubstituted; preferably -pyrrolidinyl, -piperidinyl, -morpholinyl, -piperazinyl, -thiomorpholinyl, or -thiomorpholinyl dioxide, in each case saturated, unsubstituted or monosubstituted with —$C_1$-$C_4$-alkyl; -6-14-membered aryl, unsubstituted, mono- or polysubstituted; preferably -phenyl, unsubstituted; —O—$C_1$-$C_4$-alkyl; —S—$C_1$-$C_4$-alkyl; —C(=O)OH; —C(=O)O—$C_1$-$C_4$-alkyl; —C(=O)$NH_2$; —C(=O)NH$C_1$-$C_4$-alkyl; —C(=O)N($C_1$-$C_4$-alkyl)$_2$; —C(=O)N($C_1$-$C_4$-alkyl)($C_1$-$C_4$-alkyl-OH); —C(=O)NH—$(CH_2)_{1-3}$-3-12-membered cycloalkyl, saturated or unsaturated, unsubstituted or monosubstituted with —OH; preferably —C(=O)NH—$(CH_2)_{1-3}$-cyclobutyl, saturated or unsaturated, unsubstituted or monosubstituted with —OH; —C(=O)-3-12-membered heterocycloalkyl, saturated or unsaturated, unsubstituted, mono- or polysubstituted; preferably —C(=O)-morpholinyl, saturated, unsubstituted; —S(=O)$C_1$-$C_4$-alkyl; —S(=O)$_2$$C_1$-$C_4$-alkyl; and —S(=O)$_2$N($C_1$-$C_4$-alkyl)$_2$. Preferably, $R^5$ means -pyridinyl, —$CH_2$-pyridinyl, or -pyrimidinyl, in each case unsubstituted or substituted with one, two, or three substituents independently of one another selected from the group consisting of —CN, —$CH_3$, —$CHF_2$, —$C(CH_3)_2$OH, —$OCH_3$, —$OCF_3$, -cyclopropyl, -morpholinyl, -azetanyl, and -pyridyl.

In still another preferred embodiment of the compound according to the invention, $R^5$ means a bicyclic 9-10-membered heteroaryl moiety, unsubstituted, mono- or polysubstituted. Preferably, $R^5$ means imidazo[1,2-a]pyrazine, unsubstituted or monosubstituted with —$C_1$-$C_4$-alkyl.

In a particularly preferred embodiment of the compound according to the invention
$R^1$ means —H or —$CH_3$;
$R^2$ means —$C_1$-$C_6$-alkyl, linear or branched, saturated, unsubstituted; -cyclopropyl; or -cyclopropylmethylene; or $R^1$ and $R^2$ together with the nitrogen atom to which they are attached form a ring and mean -azetidine or -pyrrolidine;
$R^3$ means -phenyl, -thienyl or -pyridinyl, in each case unsubstituted or substituted with one, two, three or four substituents independently of one another selected from the group consisting of —F, —Cl, —Br, —CN, —$C_1$-$C_4$-alkyl, —$CH_3$, —$CH_2CH_3$, —$CH_2$F, —$CHF_2$, —$CF_3$, —$OCF_3$, —OH, —O—$C_1$-$C_4$-alkyl, —$OCH_3$, —C(=O)$NH_2$, C(=O)NH$CH_3$, —C(=O)N($CH_3$)$_2$, —$NH_2$, —NH$CH_3$, —N($CH_3$)$_2$, —NHC(=O)$CH_3$, —$CH_2$OH, SO$CH_3$ and SO$_2$$CH_3$; or
$R^4$ means
—H;
—$C_1$-$C_6$-alkyl, linear or branched, saturated, unsubstituted or substituted with one, two, three or four substituents independently of one another selected from the group consisting of —F, —Cl, —Br, —I, —CN, —OH, =O, —S(=O)$_2$—$C_1$-$C_4$-alkyl and —O—$C_1$-$C_4$-alkyl;
3-6-membered cycloalkyl, unsubstituted or substituted with one, two, three or four substituents independently of one another selected from the group consisting of —F, —Cl, —Br, —I, —CN, —OH, and —O—$C_1$-$C_4$-alkyl, wherein said 3-6-membered cycloalkyl is connected through —$C_1$-$C_6$-alkylene;
3-12-membered heterocycloalkyl, saturated or unsaturated, unsubstituted or substituted with one, two, three or four substituents independently of one another selected from the group consisting of —F, —Cl, —Br, —I, —CN, —OH, and —O—$C_1$-$C_4$-alkyl; wherein said 3-12-membered heterocycloalkyl is optionally connected through —$C_1$-$C_6$-alkylene-, unsubstituted or substituted with =O;
6-14-membered aryl, unsubstituted or substituted with one, two, three or four substituents independently of one another selected from the group consisting of —F, —Cl, —Br, —I, —CN, —OH, and —O—$C_1$-$C_4$-alkyl; wherein said 6-14-membered aryl is optionally connected through —$C_1$-$C_6$-alkylene- or —S(=O)$_2$—;
$R^5$ means
—H;
—$C_1$-$C_6$-alkyl, linear or branched, saturated or unsaturated, unsubstituted or substituted with one, two, three or four substituents independently of one another selected from the group consisting of —F, —Cl, —Br, —I, —CN, =O, —OH, —O—$C_1$-$C_4$-alkyl, —O—$(CH_2CH_2$—O)$_{1-30}$—H, —O—$(CH_2CH_2$—O)$_{1-30}$—$CH_3$, —C(=O)OH, —C(=O)$C_1$-$C_4$-alkyl, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —(C=O)-heterocycloalkyl, —S(=O)$C_1$-$C_4$-alkyl, —S(=O)$_2$$C_1$-$C_4$-alkyl, —$NH_2$, —NH—$C_1$-$C_4$-alkyl, —N($C_1$-$C_4$-alkyl)$_2$, —NHC(=O)—$C_1$-$C_4$-alkyl, —NH—S(=O)$_2$$C_1$-$C_4$-alkyl; preferably —$C_1$-$C_6$-alkyl, linear or branched, saturated or unsaturated, monosubstituted with a 3-12-membered heterocycloalkyl moiety, saturated or unsaturated, unsubstituted, mono- or polysubstituted; wherein said 3-12-membered heterocycloalkyl moiety is optionally connected through —C=O—;
3-12-membered heterocycloalkyl, saturated or unsaturated, unsubstituted or substituted with one, two, three or four substituents independently of one another selected from the group consisting of —F, —Cl, —Br, —I, —CN, =O, —OH, —$C_1$-$C_4$-alkyl, —$NH_2$, —NH—$C_1$-$C_4$-alkyl, —N($C_1$-$C_4$-alkyl)$_2$, —NHC(=O)—$C_1$-$C_4$-alkyl, —NHS(=O)$_2$—$C_1$-$C_4$-alkyl, —O—$C_1$-$C_4$-alkyl, —O—$(CH_2CH_2$—O)$_{1-30}$—H, —O—$(CH_2CH_2$—O)$_{1-30}$—$CH_3$, —C(=O)OH, —C(=O)O$C_1$-$C_4$-alkyl, —C(=O)$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl, —S(=O)$_2$$C_1$-$C_4$-alkyl, -phenyl, —C(=O)-phenyl, —C(=O)-pyridyl, -pyridyl, -pyrimidinyl, and -pyridazinyl; wherein said 3-12-membered heterocycloalkyl moiety is optionally connected through —$C_1$-$C_6$-alkylene-, linear or branched, saturated or unsaturated, unsubstituted; or wherein said 3-12-membered heterocycloalkyl moiety is optionally connected through —C=O— or —$CH_2$—C=O—;
-1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, -benzo[c][1,2,5]oxadiazolyl, -imidazo[1,2-a]pyrazinyl, or -1H-pyrrolo[2,3-b]pyridinyl, in each case unsubstituted, mono- or polysubstituted;
and
$R^6$, $R^7$, $R^8$, $R^9$, $R^{10}$, and $R^{11}$ mean —H; or $R^6$ and $R^7$ together mean =O and $R^8$, $R^9$, $R^{10}$, and $R^{11}$ mean —H.

In preferred embodiments, the compound according to the invention has a structure according to any of general formulas (II-A) to (VI-F):

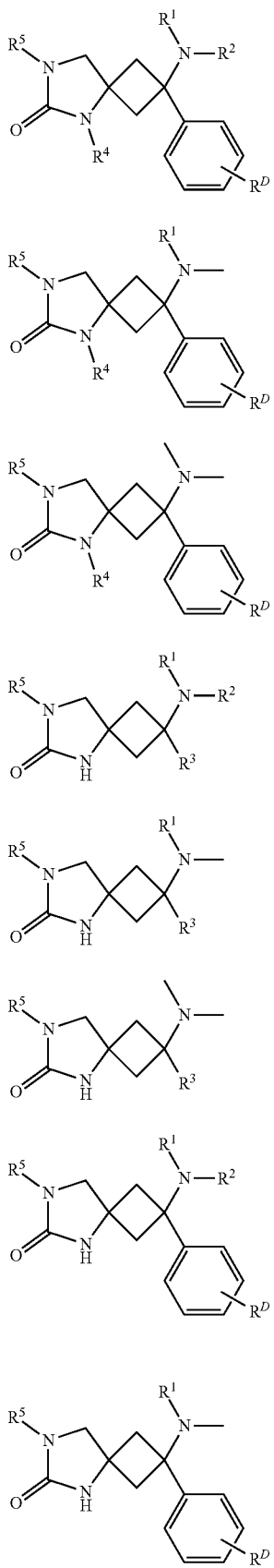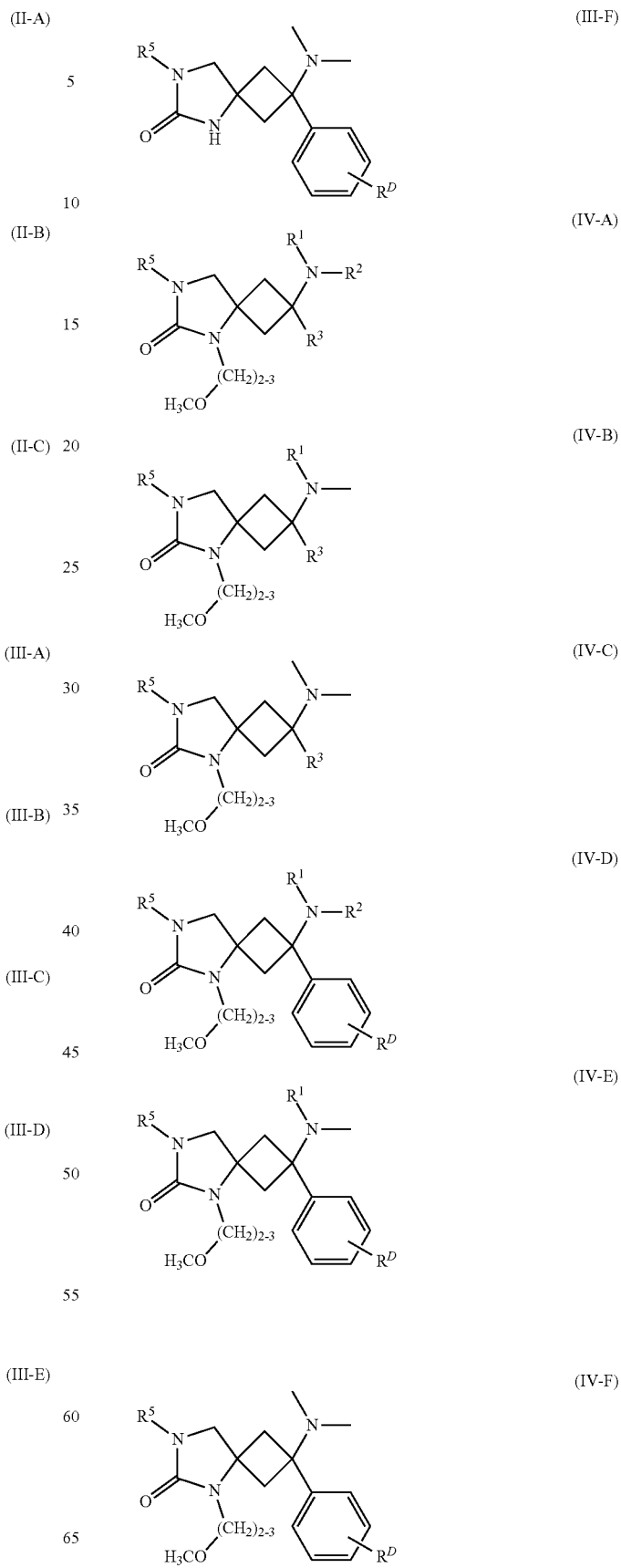

(V-A)
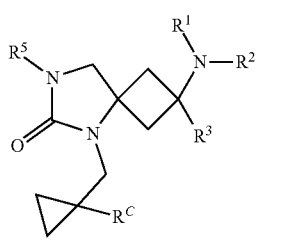
(V-B)
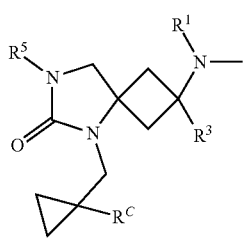
(V-C)
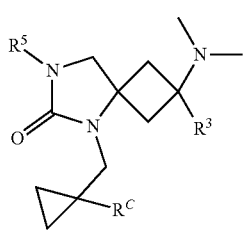
(V-D)
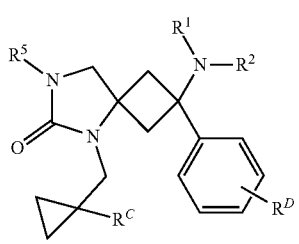
(V-E)
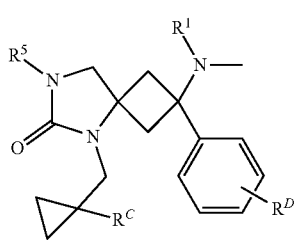
(V-F)
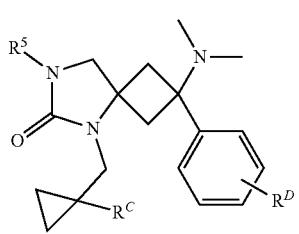
(VI-A)
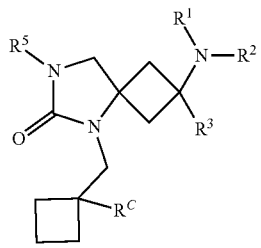
(VI-B)
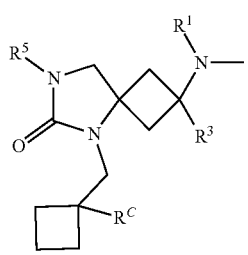
(VI-C)
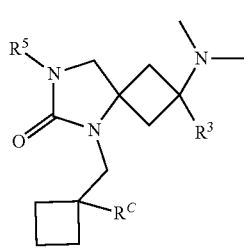
(VI-D)
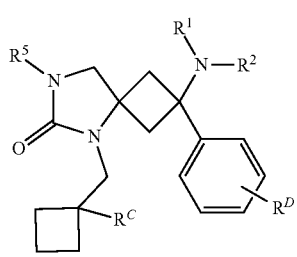
(VI-E)
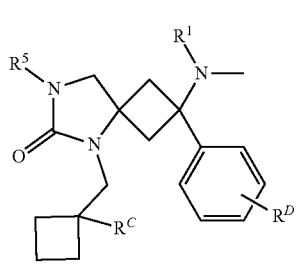
(VI-F)
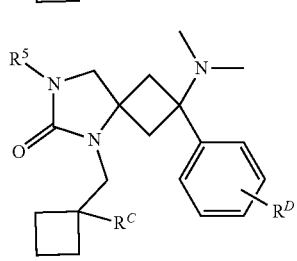
wherein in each case
$R^1$, $R^2$, $R^3$, $R^4$, and $R^5$ are defined as above,
$R^C$ means —H, —OH, —F, —CN or —$C_1$-$C_4$-alkyl; preferably —H or —OH;
$R^D$ means —H or —F;
or a physiologically acceptable salt thereof.

In preferred embodiments, the compound according to the invention, preferably the compound according to any of general formulas (II-A) to (VI-F), has a structure wherein $R^5$ means

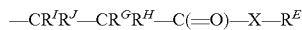
—$CR^IR^J$—$CR^GR^H$—C(=O)—X—$R^E$ wherein
X means —O—, —S— or —$NR^F$—;
$R^E$ means
- —H;
- —$C_1$-$C_6$-alkyl, linear or branched, saturated or unsaturated, unsubstituted, mono- or polysubstituted;
- a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;
- a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;
- a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or
- a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;

in case X means $NR^F$, RF means
- —H;
- —$C_1$-$C_6$-alkyl, linear or branched, saturated or unsaturated, unsubstituted, mono- or polysubstituted; a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;
- a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;
- a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or
- a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;

or in case X means $NR^F$, $R^E$ and RF together with the nitrogen atom to which they are attached form a 3-12-membered heterocycloalkyl moiety, saturated or unsaturated, unsubstituted, mono- or polysubstituted; $R^G$, $R^H$, $R^I$, $R^J$, independently of one another mean —H, —F, —Cl, —Br, —I, —OH, or —$C_1$-$C_6$-alkyl, linear or branched, saturated or unsaturated, unsubstituted, mono- or polysubstituted;

or $R^G$ and $R^H$ together with the carbon atom to which they are attached form a 3-12-membered cycloalkyl moiety, saturated or unsaturated, unsubstituted, mono- or polysubstituted; or a 3-12-membered heterocycloalkyl moiety, saturated or unsaturated, unsubstituted, mono- or polysubstituted;

In preferred embodiments,
$R^G$ and $R^H$ independently of one another mean —H or —$C_1$-$C_6$-alkyl; preferably —H or —$CH_3$; or $R^G$ and $R^H$ together with the carbon atom to which they are attached form a 3-12-membered cycloalkyl moiety, saturated or unsaturated, unsubstituted, mono- or polysubstituted; preferably cyclopropyl, cyclobutyl or cyclopentyl, in each case unsubstituted; or a 3-12-membered heterocycloalkyl moiety, saturated or unsaturated, unsubstituted, mono- or polysubstituted; preferably oxetanyl, tetrahydrofuranyl or tetrahydropyranyl, in each case unsubstituted; and/or
$R^I$, $R^J$, independently of one another mean —H, —F, —OH, or —$C_1$-$C_6$-alkyl; preferably —H.

In a preferred embodiment, $R^E$ means —H.

In another preferred embodiment, $R^E$ means —$C_1$-$C_6$-alkyl, linear or branched, saturated or unsaturated, unsubstituted, mono- or polysubstituted. Preferably, $R^E$ means —$C_1$-$C_6$-alkyl, linear or branched, saturated, unsubstituted, mono- or polysubstituted. More preferably, $R^E$ means —$C_1$-$C_6$-alkyl, linear or branched, saturated, unsubstituted or monosubstituted with a substituent selected from the group consisting of —F, —Cl, —Br, —I, —CN, —OH, —O—$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2$$C_1$-$C_4$-alkyl.

In still another preferred embodiment, $R^E$ means a 3-12-membered cycloalkyl moiety, saturated or unsaturated, unsubstituted, mono- or polysubstituted, wherein said 3-12-membered cycloalkyl moiety is optionally connected through —$C_1$-$C_6$-alkylene-, linear or branched, saturated or unsaturated, unsubstituted, mono- or polysubstituted; preferably through —$CH_2$— or —$CH_2CH_2$—. Preferably, $R^E$ means a 3-6-membered cycloalkyl moiety, saturated, unsubstituted, mono- or polysubstituted, wherein said 3-12-membered cycloalkyl moiety is connected through —$C_1$-$C_6$-alkylene-, linear or branched, saturated, unsubstituted. More preferably, $R^E$ means -cyclobutyl, unsubstituted or monosubstituted with —F, —OH, —CN or —$C_1$-$C_4$-alkyl, wherein said -cyclobutyl is connected through —$CH_2$— or —$CH_2CH_2$—.

In yet another preferred embodiment, $R^E$ means a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted. Preferably, $R^E$ means a 4-6-membered heterocycloalkyl moiety, saturated or unsaturated, unsubstituted, mono- or polysubstituted. More preferably, $R^E$ means -heterocyclobutyl, unsubstituted.

In a further preferred embodiment, $R^E$ means a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted. Preferably, $R^E$ means a 5-6-membered heteroaryl moiety, unsubstituted, mono- or polysubstituted, wherein said 5-6-membered heteroaryl moiety is optionally connected through —CH$_2$—. More preferably, R$^E$ means a 5-6-membered heteroaryl moiety, unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl and —S(=O)$_2$C$_1$-C$_4$-alkyl, wherein said 5-6-membered heteroaryl moiety is optionally connected through —CH$_2$—. Still more preferably, R$^E$ means -oxazolyl, -pyridinyl, -pyridazinyl or -pyrimidinyl, in each case unsubstituted or substituted with one, two, three or four substituents independently of one another selected from the group consisting of —F, —Cl, Br, —I, —CN, —OH, —C$_1$-C$_4$-alkyl, —O—C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, S(=O)C$_1$-C$_4$-alkyl and —S(=O)$_2$C$_1$-C$_4$-alkyl, wherein said -oxazolyl, -pyridinyl, -pyridazinyl or -pyrimidinyl is optionally connected through —CH$_2$—.

In a preferred embodiment, X means NR$^F$ and R$^E$ and RF together with the nitrogen atom to which they are attached form a 3-12-membered heterocycloalkyl moiety, saturated or unsaturated, unsubstituted, mono- or polysubstituted. Preferably, X means NR$^F$ and R$^E$ and RF together with the nitrogen atom to which they are attached form a 5-6-membered heterocycloalkyl moiety, saturated or unsaturated, unsubstituted, mono- or polysubstituted. More preferably, X means NR$^F$ and R$^E$ and RF together with the nitrogen atom to which they are attached form -pyrrolidinyl, -pyrimidinyl, -morpholinyl, -thiomorpholinyl, -thiomorpholinyl dioxide, or -piperazinyl, in each case unsubstituted or substituted with one, two, three or four substituents independently of one another selected from the group consisting of =O, —OH, and —C(=O)NH$_2$, wherein said -pyrrolidinyl, -pyrimidinyl, -morpholinyl, -thiomorpholinyl, -thiomorpholinyl dioxide, or -piperazinyl is optionally condensed with an imidazole moiety, unsubstituted.

In a preferred embodiment, R$^E$ means
— H;
—C$_1$-C$_6$-alkyl, linear or branched, saturated or unsaturated, unsubstituted or substituted with one, two, three or four substituents independently of one another selected from the group consisting of —F, —Cl, —Br, —I, —CN, —O—C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —OH, —S(=O)C$_1$-C$_4$-alkyl and —S(=O)$_2$C$_1$-C$_4$-alkyl;
-cyclobutyl, unsubstituted or monosubstituted with —OH; wherein said -cyclobutyl is connected through —CH$_2$—;
-heterocyclobutyl, unsubstituted; or
-oxazolyl, -pyridinyl, -pyridazinyl or -pyrimidinyl, in each case unsubstituted or substituted with one, two, three or four substituents independently of one another selected from the group consisting of —F, —Cl, Br, —I, —OH, —O—C$_1$-C$_4$-alkyl, —CN, and —S(=O)$_2$C$_1$-C$_4$-alkyl; wherein said -oxazolyl, -pyridinyl, -pyridazinyl or -pyrimidinyl is optionally connected through —CH$_2$—;
in case X means NR$^F$, RF means —H or —CH$_3$;
or in case X means NR$^F$, R$^E$ and R$^F$ together with the nitrogen atom to which they are attached form a piperidine moiety, a pyrrolidine moiety, a morpholine moiety, a thiomorpholine moiety, a thiomorpholine dioxide moiety, or a piperazine moiety, in each case unsubstituted or substituted with one, two, three or four substituents independently of one another selected from the group consisting of =O, —OH, and —C(=O)NH$_2$; wherein said piperidine moiety, pyrrolidine moiety, morpholine moiety, thiomorpholine moiety, thiomorpholine dioxide moiety, or piperazine moiety is optionally condensed with an imidazole moiety, unsubstituted.

In a preferred embodiment, X means NR$^F$ and R$^F$ means —H or —C$_1$-C$_6$-alkyl, linear or branched, saturated or unsaturated, unsubstituted, mono- or polysubstituted. Preferably, R$^E$ means —H or —CH$_3$. More preferably, R$^F$ means —H.

Preferably, R$^5$ has a meaning selected from the group consisting of:

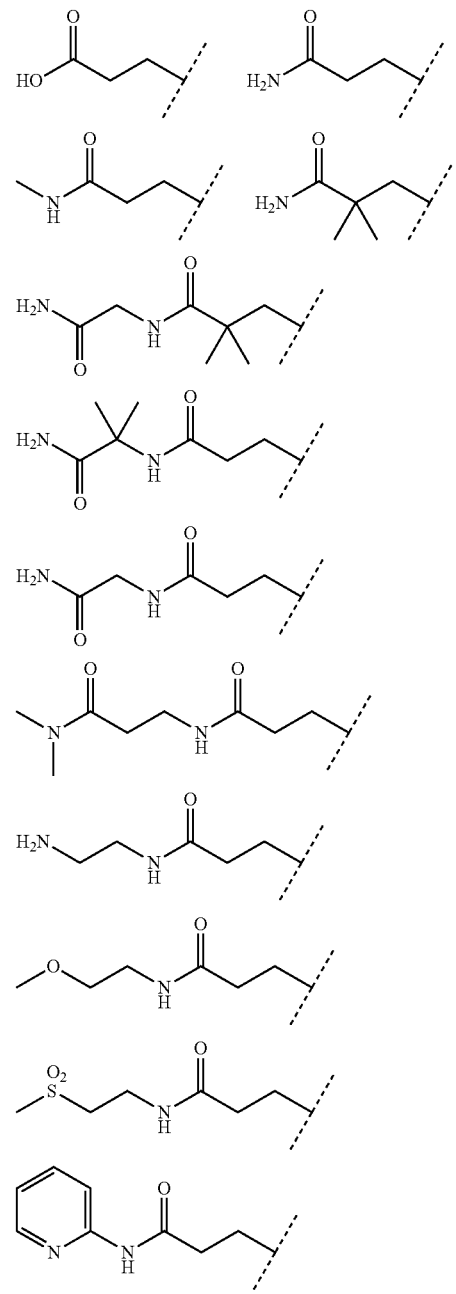

-continued
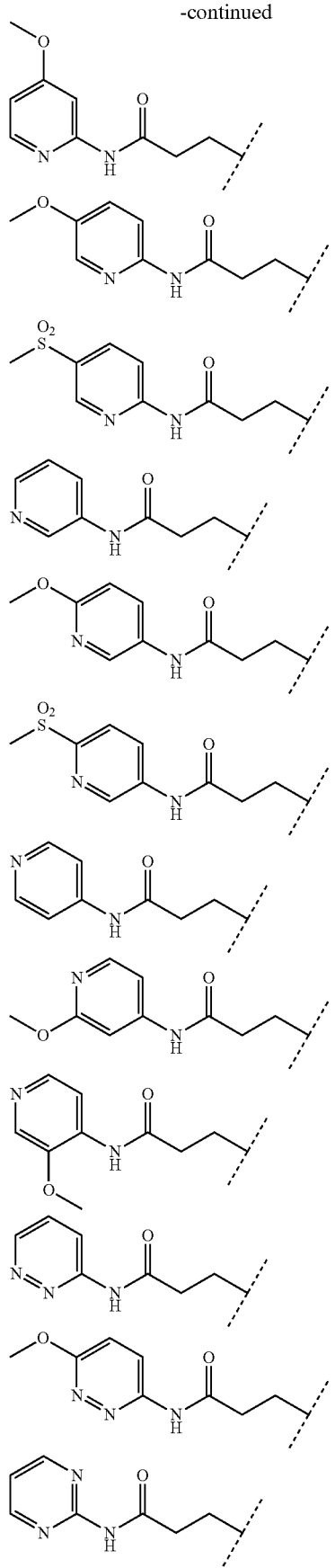
-continued
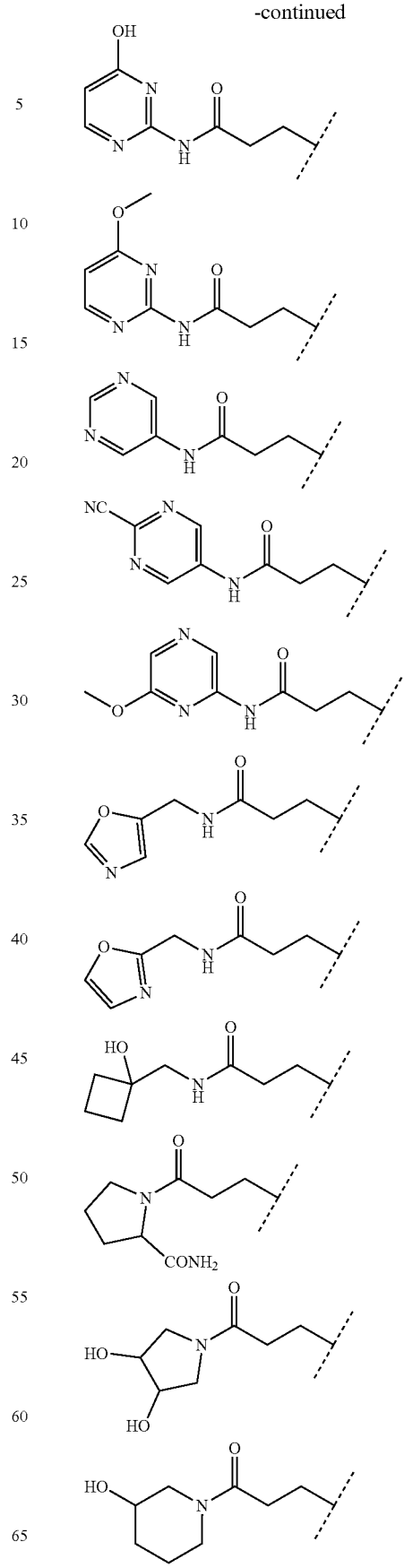

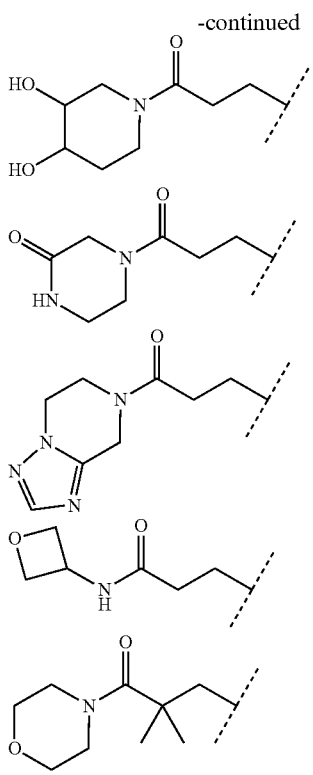

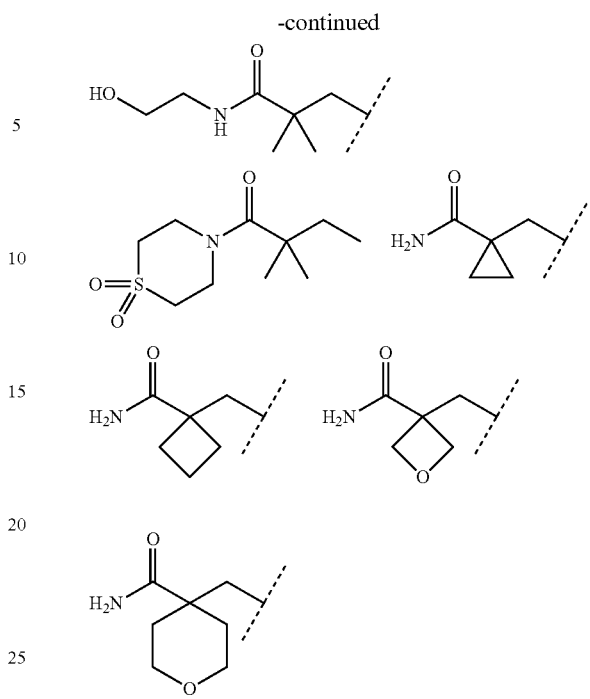

Preferred compounds according to the invention are selected from the group consisting of:

2-(2-(dimethylamino)-6-oxo-2-phenyl-5,7-diazaspiro[3.4]octan-7-yl)acetamide
2-(dimethylamino)-7-(2-(1,1-dioxidothiomorpholino)-2-oxoethyl)-2-phenyl-5,7-diazaspiro-[3.4]-octan-6-one
5-(2-(dimethylamino)-6-oxo-2-phenyl-5,7-diazaspiro[3.4]octan-7-yl)-4-methoxypyrimidine-2-carbonitrile
5-(cyclobutylmethyl)-2-(dimethylamino)-7-(2-(1,1-dioxidothiomorpholino)-2-oxoethyl)-2-phenyl-5,7-diazaspiro[3.4]octan-6-one
2-(5-(cyclobutylmethyl)-2-(dimethylamino)-6-oxo-2-phenyl-5,7-diazaspiro[3.4]octan-7-yl)acetamide
5-(5-(cyclobutylmethyl)-2-(dimethylamino)-6-oxo-2-phenyl-5,7-diazaspiro[3.4]octan-7-yl)-4-methoxypyrimidine-2-carbonitrile
2-(dimethylamino)-7-(4-methyl-2-morpholin-4-ylpyrimidin-5-yl)-2-phenyl-5,7-diazaspiro[3.4]octan-6-one
7-(6-(azetidin-1-yl)-4-methylpyridin-3-yl)-2-(dimethylamino)-2-phenyl-5,7-diazaspiro[3.4]octan-6-one
5-(2-(dimethylamino)-2-(3-fluorophenyl)-6-oxo-5,7-diazaspiro[3.4]octan-7-yl)-4-methylpicolinonitrile
5-(5-(cyclopropylmethyl)-2-(dimethylamino)-2-(3-fluorophenyl)-6-oxo-5,7-diazaspiro[3.4]octan-7-yl)-4-methyl-picolinonitrile
6-(5-(cyclopropylmethyl)-2-(dimethylamino)-2-(3-fluorophenyl)-6-oxo-5,7-diazaspiro[3.4]octan-7-yl)-5-methyl-nicotinonitrile
2-(dimethylamino)-2-(3-fluorophenyl)-7-(5-(trifluoromethoxy)pyridin-2-yl)-5,7-diazaspiro[3.4]-octan-6-one
5-(cyclopropylmethyl)-2-(dimethylamino)-2-(3-fluorophenyl)-7-(5-(trifluoromethoxy)pyridin-2-yl)-5,7-diazaspiro[3.4]octan-6-one
2-(dimethylamino)-7-(4-methyl-6-morpholinopyridin-3-yl)-2-phenyl-5,7-diazaspiro[3.4]octan-6-one
2-(dimethylamino)-7-(6-(2-hydroxypropan-2-yl)-4-methylpyridin-3-yl)-2-phenyl-5,7-diazaspiro-[3.4]octan-6-one
2-(dimethylamino)-7-(4-(2-hydroxypropan-2-yl)-2-methylphenyl)-2-phenyl-5,7-diazaspiro[3.4]-octan-6-one
7-(6-(difluoromethyl)-4-methylpyridin-3-yl)-2-(dimethylamino)-2-(3-fluorophenyl)-5,7-diazaspiro-[3.4]octan-6-one
2-(dimethylamino)-5-((3-fluorooxetan-3-yl)methyl)-2-(3-fluorophenyl)-7-(5-(trifluoromethoxy)-pyridin-2-yl)-5,7-diazaspiro[3.4]octan-6-one
5-(cyclopropylmethyl)-7-(6-(difluoromethyl)-4-methylpyridin-3-yl)-2-(dimethylamino)-2-(3-fluoro-phenyl)-5,7-diazaspiro[3.4]octan-6-one
2-(dimethylamino)-7-(2-morpholinopyrimidin-5-yl)-2-phenyl-5,7-diazaspiro[3.4]octan-6-one
2-(dimethylamino)-5-((1-fluorocyclopropyl)methyl)-2-(3-fluorophenyl)-7-(5-(trifluoromethoxy)-pyridin-2-yl)-5,7-diazaspiro[3.4]octan-6-one
2-(dimethylamino)-2-(3-fluorophenyl)-5-((1-hydroxycyclobutyl)methyl)-7-(5-(trifluoromethoxy)-pyridin-2-yl)-5,7-diazaspiro[3.4]octan-6-one
5-(cyclopropylmethyl)-2-(dimethylamino)-2-(3-fluorophenyl)-7-(4-(2-hydroxypropan-2-yl)phenyl)-5,7-diazaspiro[3.4]octan-6-one 2-(dimethylamino)-5-((3-fluorooxetan-3-yl)methyl)-2-phenyl-7-(5-(trifluoromethoxy)pyridin-2-yl)-5,7-diazaspiro[3.4]octan-6-one
5-(cyclopropylmethyl)-2-(dimethylamino)-2-(3-fluorophenyl)-7-((6-(trifluoromethyl)pyridin-3-yl)methyl)-5,7-diazaspiro[3.4]octan-6-one
5-(cyclopropylmethyl)-2-(dimethylamino)-2-(3-fluorophenyl)-7-(2-(methylsulfonyl)ethyl)-5,7-diazaspiro[3.4]octan-6-one
5-(cyclopropylmethyl)-2-(dimethylamino)-2-phenyl-7-(5-(trifluoromethoxy)pyridin-2-yl)-5,7-diazaspiro[3.4]octan-6-one
5-(cyclopropylmethyl)-2-(dimethylamino)-7-((3-fluorooxetan-3-yl)methyl)-2-(3-fluorophenyl)-5,7-diazaspiro[3.4]octan-6-one
5-(cyclopropylmethyl)-7-(6-cyclopropylpyridin-3-yl)-2-(dimethylamino)-2-phenyl-5,7-diazaspiro[3.4]octan-6-one
7-(6-cyclopropyl-4-methylpyridin-3-yl)-5-(cyclopropylmethyl)-2-(dimethylamino)-2-phenyl-5,7-diazaspiro[3.4]octan-6-one
7-(6-cyclopropyl-4-methylpyridin-3-yl)-2-(dimethylamino)-5-((3-fluorooxetan-3-yl)methyl)-2-phenyl-5,7-diazaspiro[3.4]octan-6-one
5-(cyclopropylmethyl)-2-(dimethylamino)-2-(3-fluorophenyl)-7-(2-methoxy-2-methylpropyl)-5,7-diazaspiro[3.4]octan-6-one
2-(dimethylamino)-2-phenyl-7-(2-pyridin-4-ylpyrimidin-5-yl)-5,7-diazaspiro[3.4]octan-6-one
5-(cyclopropylmethyl)-2-(dimethylamino)-2-phenyl-7-[5-(trifluoromethyl)pyridin-3-yl]-5,7-diazaspiro[3.4]octan-6-one
5-[5-(cyclopropylmethyl)-2-(dimethylamino)-6-oxo-2-phenyl-5,7-diazaspiro[3.4]octan-7-yl]-3-(trifluoromethyl)pyridine-2-carbonitrile
2-(dimethylamino)-2-(3-fluorophenyl)-7-(4-morpholinobenzyl)-5,7-diazaspiro[3.4]octan-6-one
5-(cyclopropylmethyl)-2-(dimethylamino)-2-(3-fluorophenyl)-7-[(1-hydroxycyclobutyl)methyl]-5,7-diazaspiro[3.4]octan-6-one
5-(cyclopropylmethyl)-2-(dimethylamino)-2-phenyl-7-(2-pyridin-4-ylpyrimidin-5-yl)-5,7-diazaspiro[3.4]octan-6-one
3-(5-(cyclopropylmethyl)-2-(dimethylamino)-2-(3-fluorophenyl)-6-oxo-5,7-diazaspiro[3.4]octan-7-yl)propane nitrile
3-[5-(cyclopropylmethyl)-2-(dimethylamino)-6-oxo-2-phenyl-5,7-diazaspiro[3.4]octan-7-yl]-propanenitrile
5-(cyclopropylmethyl)-2-(dimethylamino)-7-[(1-hydroxycyclobutyl)methyl]-2-phenyl-5,7-diazaspiro[3.4]octan-6-one
5-(cyclopropylmethyl)-2-(dimethylamino)-2-(3-fluorophenyl)-7-[2-(oxetan-3-yl)ethyl]-5,7-diazaspiro[3.4]octan-6-one and the physiologically acceptable salts thereof.

According to the invention, unless expressly stated otherwise, "—$C_1$-$C_4$-alkyl", "—$C_1$-$C_6$-alkyl" and any other alkyl residues can be linear or branched, saturated or unsaturated. Linear saturated alkyl includes methyl, ethyl, n-propyl, n-butyl, n-pentyl and n-hexyl. Examples of branched saturated alkyl include but are not limited to iso-propyl, sec-butyl, and tert-butyl. Examples of linear unsaturated alkyl include but are not limited to vinyl, propenyl, allyl, and propargyl.

According to the invention, unless expressly stated otherwise, "—$C_1$-$C_4$-alkyl", "—$C_1$-$C_6$-alkyl" and any other alkyl residues can be unsubstituted, mono- or polysubstituted. Examples of substituted alkyl include but are not limited to —$CH_2CH_2OH$, —$CH_2CH_2OCH_3$, —$CH_2CH_2CH_2OCH_3$, —$CH_2CH_2S(=O)_2CH_3$, —$CH_2C(=O)NH_2$, —$C(CH_3)_2C(=O)NH_2$, —$CH_2C(CH_3)_2C(=O)NH_2$, and —$CH_2CH_2C(=O)N(CH_3)_2$.

According to the invention, unless expressly stated otherwise, "—$C_1$-$C_6$-alkylene-", "—$C_1$-$C_4$-alkylene" and any other alkylene residue can be unsubstituted, mono- or polysubstituted. Examples of saturated alkylene include but are not limited to —$CH_2$—, —$CH(CH_3)$—, —$C(CH_3)_2$—, —$CH_2CH_2$—, —$CH(CH_3)CH_2$—, —$CH_2CH(CH_3)$—, —$CH(CH_3)$—$CH(CH_3)$—, —$C(CH_3)_2CH_2$—, —$CH_2C(CH_3)_2$—, —$CH(CH_3)C(CH_3)_2$—, —$C(CH_3)_2CH(CH_3)$—, $C(CH_3)_2C(CH_3)_2$—, —$CH_2CH_2CH_2$—, and —$C(CH_3)_2CH_2CH_2$—. Examples of unsaturated alkylene include but are not limited to —CH=CH—, —C≡C—, —$C(CH_3)$=CH—, —CH=$C(CH_3)$—, —$C(CH_3)$=$C(CH_3)$—, —$CH_2CH$=CH—, —CH=$CHCH_2$—, —CH=CH—CH=CH—, and —CH=CH—C≡C—.

According to the invention, unless expressly stated otherwise, "—$C_1$-$C_6$-alkylene-", "—$C_1$-$C_4$-alkylene" and any other alkylene residue can be unsubstituted, mono- or polysubstituted. Examples of substituted —$C_1$-$C_6$-alkylene- include but are not limited to —CHF—, —$CF_2$—, —CHOH— and —C(=O)—.

According to the invention, moieties may be connected through —$C_1$-$C_6$-alkylene-, i.e. the moieties may not be directly bound to the core structure of compound according to general formula (I), but may be connected to the core structure of compound according to general formula (I) or its periphery through a —$C_1$-$C_6$-alkylene-linker.

According to the invention, "3-12-membered cycloalkyl moiety" means a non-aromatic, monocyclic, bicyclic or tricyclic moiety comprising 3 to 12 ring carbon atoms but no heteroatoms in the ring. Examples of preferred saturated 3-12-membered cycloalkyl moieties according to the invention include but are not limited to cyclopropane, cyclobutane, cyclopentane, cyclohexane, cycloheptane, cyclooctane, hydrindane, and decaline. Examples of preferred unsaturated 3-12-membered cycloalkyl moiety moieties according to the invention include but are not limited to cyclopropene, cyclobutene, cyclopentene, cyclopentadiene, cyclohexene, 1,3-cyclohexadiene, and 1,4-cyclohexadiene. The 3-12-membered cycloalkyl moiety, which is bonded to the compound according to the invention, in its periphery may optionally be condensed with a 3-12-membered heterocycloalkyl moiety, saturated or unsaturated, unsubstituted, mono- or polysubstituted; and/or with a 6-14-membered aryl moiety, unsubstituted, mono- or polysubstituted; and/or with a 5-14-membered heteroaryl moiety, unsubstituted, mono- or polysubstituted. Under these circumstances, the ring atoms of the condensed moieties are not included in the 3 to 12 ring atoms of the 3-12-membered cycloalkyl moiety. Examples of 3-12-membered cycloalkyl moieties condensed with 3-12-membered heterocycloalkyl moieties include but are not limited to octahydro-1H-indol, decahydroquinoline, decahydroisoquinoline, octahydro-2H-benzo[b][1,4]oxazin, and decahydroquinoxalin, which in each case are connected through the 3-12-membered cycloalkyl moiety. Examples of 3-12-membered cycloalkyl moieties condensed with 6-14-membered aryl moieties include but are not limited to 2,3-dihydro-1H-indene and tetraline, which in each case are connected through the 3-12-membered cycloalkyl moiety. Examples of 3-12-membered cycloalkyl moieties condensed with 5-14-membered heteroaryl moieties include but are not limited to 5,6,7,8-tetrahydroquinoline and 5,6,7,8-tetrahydroquinazoline, which in each case are connected through the 3-12-membered cycloalkyl moiety.

According to the invention, the 3-12-membered cycloalkyl moiety may optionally be connected through —$C_1$-$C_6$-alkylene-, i.e. the 3-12-membered cycloalkyl moiety may not be directly bound to the compound according to general formula (I) but may be connected thereto through a —$C_1$-$C_6$-alkylene- linker. Examples include but are not limited to —$CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, and —$CH_2CH_2$-cyclohexyl.

According to the invention, unless expressly stated otherwise, the 3-12-membered cycloalkyl moiety can be unsubstituted, mono- or polysubstituted. Examples of substituted 3-12-membered cycloalkyl moieties include but are not limited to —$CH_2$-1-hydroxy-cyclobutyl.

According to the invention, "3-12-membered heterocycloalkyl moiety" means a non-aromatic, monocyclic, bicyclic or tricyclic moiety comprising 3 to 12 ring atoms, wherein each cycle comprises independently of one another 1, 2, 3, 4 or more heteroatoms independently of one another selected from the group consisting of nitrogen, oxygen and sulfur, whereas sulfur may be oxidized (S(=O) or (S(=O)$_2$), whereas the remaining ring atoms are carbon atoms, and whereas bicyclic or tricyclic systems may share common heteroatom(s). Examples of preferred saturated 3-12-membered heterocycloalkyl moieties according to the invention include but are not limited to aziridin, azetidine, pyrrolidine, imidazolidine, pyrazolidine, piperidine, piperazine, triazolidine, tetrazolidine, oxiran, oxetane, tetrahydrofurane, tetrahydropyrane, thiirane, thietane, tetrahydrothiophene, diazepane, oxazolidine, isoxazolidine, thiazolidine, isothiazolidine, thiadiazolidine, morpholine, thiomorpholine. Examples of preferred unsaturated 3-12-membered heterocycloalkyl moiety moieties according to the invention include but are not limited to oxazoline, pyrazoline, imidazoline, isoxazoline, thiazoline, isothiazoline, and dihydropyran. The 3-12-membered heterocycloalkyl moiety, which is bonded to the compound according to the invention, in its periphery may optionally be condensed with a 3-12-membered cycloalkyl moiety, saturated or unsaturated, unsubstituted, mono- or polysubstituted; and/or with a 6-14-membered aryl moiety, unsubstituted, mono- or polysubstituted; and/or with a 5-14-membered heteroaryl moiety, unsubstituted, mono- or polysubstituted. Under these circumstances, the ring atoms of the condensed moieties are not included in the 3 to 12 ring atoms of the 3-12-membered heterocycloalkyl moieties. Examples of 3-12-membered heterocycloalkyl moieties condensed with 3-12-membered cycloalkyl moieties include but are not limited to octahydro-1H-indol, decahydroquinoline, decahydroisoquinoline, octahydro-2H-benzo[b][1,4]-oxazin, and decahydroquinoxalin, which in each case are connected through the 3-12-membered heterocycloalkyl moiety. An examples of a 3-12-membered heterocycloalkyl moiety condensed with a 6-14-membered aryl moiety includes but is not limited to 1,2,3,4-tetrahydroquinoline, which is connected through the 3-12-membered heterocycloalkyl moiety. An example of a 3-12-membered heterocycloalkyl moiety condensed with a 5-14-membered heteroaryl moieties includes but is not limited to 5,6,7,8-tetrahydro-[1,2,4]triazolo[1,5-a]pyrazine, which is connected through the 3-12-membered heterocycloalkyl moiety.

According to the invention, the 3-12-membered heterocycloalkyl moiety may optionally be connected through —$C_1$-$C_6$-alkylene-, i.e. the 3-12-membered heterocycloalkyl moiety may not be directly bound to the compound according to general formula (I) but may be connected thereto through a —$C_1$-$C_6$-alkylene- linker. Said linker may be connected to a carbon ring atom or to a hetero ring atom of the 3-12-membered heterocycloalkyl moiety. Examples include but are not limited to —$CH_2$-oxetane, —$CH_2$-pyrrolidine, —$CH_2$-piperidine, —$CH_2$-morpholine, —$CH_2CH_2$-oxetane, —$CH_2CH_2$-pyrrolidine, —$CH_2CH_2$-piperidine, and —$CH_2CH_2$-morpholine.

According to the invention, unless expressly stated otherwise, the 3-12-membered heterocycloalkyl moiety can be unsubstituted, mono- or polysubstituted. Examples of substituted 3-12-membered heterocycloalkyl moieties include but are not limited to 2-carboxamido-N-pyrrolidinyl-, 3,4-dihydroxy-N-pyrrolidinyl, 3-hydroxy-N-pyrimidinyl, 3,4-dihydroxy-N-pyrimidinyl, 3-oxo-N-piperazinyl, -tetrahydro-2H-thiopyranyl dioxide and thiomorpholinyl dioxide.

According to the invention, "6-14-membered aryl moiety" means an aromatic, monocyclic, bicyclic or tricyclic moiety comprising 6 to 14 ring carbon atoms but no heteroatoms in the ring. Examples of preferred 6-14-membered aryl moieties according to the invention include but are not limited to benzene, naphthalene, anthracen, and phenanthren. The 6-14-membered aryl moiety, which is bonded to the compound according to the invention, in its periphery may optionally be condensed with a 3-12-membered cycloalkyl moiety, saturated or unsaturated, unsubstituted, mono- or polysubstituted; and/or with a 3-12-membered heterocycloalkyl moiety, saturated or unsaturated, unsubstituted, mono- or polysubstituted; and/or with a 5-14-membered heteroaryl moiety, unsubstituted, mono- or polysubstituted. Under these circumstances, the ring atoms of the condensed moieties are not included in the 6 to 14 ring carbon atoms of the 6-14-membered heterocycloalkyl moieties. Examples of 6-14-membered aryl moieties condensed with 3-12-membered cycloalkyl moieties include but are not limited to 2,3-dihydro-1H-indene and tetraline, which in each case are connected through the 6-14-membered aryl moiety. An example of a 6-14-membered aryl moiety condensed with a 3-12-membered heterocycloalkyl moiety includes but is not limited to 1,2,3,4-tetrahydroquinoline, which is connected through the 6-14-membered aryl moiety. Examples of 6-14-membered aryl moieties condensed with 5-14-membered heteroaryl moieties include but are not limited to quinoline, isoquinoline, phenazine and phenoxacine, which in each case are connected through the 6-14-membered aryl moiety.

According to the invention, the 6-14-membered aryl moiety may optionally be connected through —$C_1$-$C_6$-alkylene-, i.e. the 6-14-membered aryl moiety may not be directly bound to the compound according to general formula (I) but may be connected thereto through a —$C_1$-$C_6$-alkylene- linker. Said linker may be connected to a carbon ring atom or to a hetero ring atom of the 6-14-membered aryl moiety. Examples include but are not limited to —CH₂—C₆H₅, —CH₂CH₂—C₆H₅ and —CH═CH—C₆H₅.

According to the invention, unless expressly stated otherwise, the 6-14-membered aryl moiety can be unsubstituted, mono- or polysubstituted. Examples of substituted 6-14-membered aryl moieties include but are not limited to 2-fluorophenyl, 3-fluorophenyl, 2-methoxyphenyl and 3-methoxyphenyl.

According to the invention, "5-14-membered heteroaryl moiety" means an aromatic, monocyclic, bicyclic or tricyclic moiety comprising 6 to 14 ring atoms, wherein each cycle comprises independently of one another 1, 2, 3, 4 or more heteroatoms independently of one another selected from the group consisting of nitrogen, oxygen and sulfur, whereas the remaining ring atoms are carbon atoms, and whereas bicyclic or tricyclic systems may share common heteroatom(s). Examples of preferred 5-14-membered heteroaryl moieties according to the invention include but are not limited to pyrrole, pyrazole, imidazole, triazole, tetrazole, furane, thiophene, oxazole, isoxazole, thiazole, isothiazole, pyridine, pyridazine, pyrimidine, pyrazine, indolicine, 9H-chinolicine, 1,8-naphthyridine, purine, imidazo[1,2-a]pyrazine, and pteridine. The 5-14-membered heteroaryl moiety, which is bonded to the compound according to the invention, in its periphery may optionally be condensed with a 3-12-membered cycloalkyl moiety, saturated or unsaturated, unsubstituted, mono- or polysubstituted; and/or with a 3-12-membered heterocycloalkyl moiety, saturated or unsaturated, unsubstituted, mono- or polysubstituted; and/or with a 6-14-membered aryl moiety, unsubstituted, mono- or polysubstituted. Under these circumstances, the ring atoms of the condensed moieties are not included in the 6 to 14 ring carbon atoms of the 6-14-membered heterocycloalkyl moieties. Examples of 5-14-membered heteroaryl moieties condensed with 3-12-membered cycloalkyl moieties include but are not limited to 5,6,7,8-tetrahydroquinoline and 5,6,7,8-tetrahydroquinazoline, which in each case are connected through the 5-14-membered heteroaryl moiety. An examples of a 5-14-membered heteroaryl moiety condensed with a 3-12-membered heterocycloalkyl moiety includes but is not limited to 5,6,7,8-tetrahydro-[1,2,4]triazolo[1,5-a]pyrazine, which is connected through the 5-14-membered heteroaryl moiety. Examples of 5-14-membered heteroaryl moieties condensed with 6-14-membered aryl moieties include but are not limited to quinoline, isoquinoline, phenazine and phenoxacine, which in each case are connected through the 5-14-membered heteroaryl moiety.

According to the invention, the 5-14-membered heteroaryl moiety may optionally be connected through —C₁-C₆-alkylene-, i.e. the 5-14-membered heteroaryl moiety may not be directly bound to the compound according to general formula (I) but may be connected thereto through a —C₁-C₆-alkylene- linker. Said linker may be connected to a carbon ring atom or to a hetero ring atom of the 5-14-membered heteroaryl moiety. Examples include but are not limited to —CH₂-oxazole, —CH₂-isoxazole, —CH₂-imidazole, —CH₂-pyridine, —CH₂-pyrimidine, —CH₂-pyridazine, —CH₂CH₂-oxazole, —CH₂CH₂-isoxazole, —CH₂CH₂-imidazole, —CH₂CH₂-pyridine, —CH₂CH₂-pyrimidine, and —CH₂CH₂-pyridazine.

According to the invention, unless expressly stated otherwise, the 5-14-membered heteroaryl moiety can be unsubstituted, mono- or polysubstituted. Examples of 5-14-membered heteroaryl moieties include but are not limited to 2-methoxy-4-pyridinyl, 2-methoxy-5-pyridinyl, 3-methoxy-4-pyridinyl, 3-methoxy-6-pyridinyl, 4-methoxy-2-pyridinyl, 2-methylsulfonyl-5-pyridinyl, 3-methylsulfonyl-6-pyridinyl, 3-methoxy-6-pyridazinyl, 2-nitrilo-5-pyrimidinyl, 4-hydroxy-2-pyrimidinyl, 4-methoxy-pyrimidinyl, 4-methoxy-pyrimidinyl-2-carbonitrile, and 2-methoxy-6-pyrazinyl.

Preferably, the compounds according to the invention have a structure according to general formula (I') or (I")

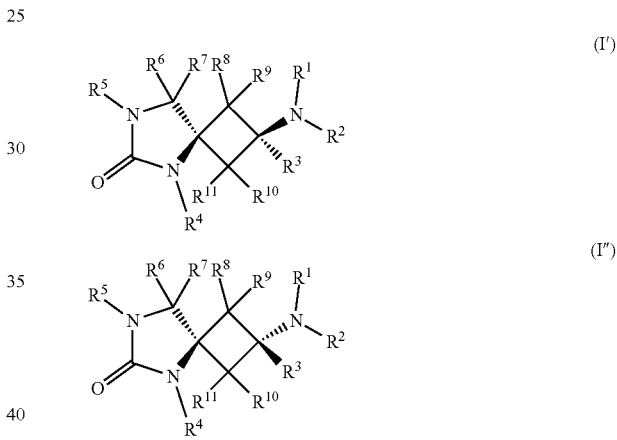

wherein $R^1$ to $R^{11}$ are defined as above, or a physiologically acceptable salt thereof.

In one preferred embodiment, the excess of the cis-isomer so designated is at least 50% de, more preferably at least 75% de, yet more preferably at least 90% de, most preferably at least 95% de and in particular at least 99% de.

Preferred compounds according to the invention are selected from the group consisting of:

cis-2-(2-(dimethylamino)-6-oxo-2-phenyl-5,7-diazaspiro[3.4]octan-7-yl)acetamide
cis-2-(dimethylamino)-7-(2-(1,1-dioxidothiomorpholino)-2-oxoethyl)-2-phenyl-5,7-diazaspiro[3.4]octan-6-one
cis-5-(2-(dimethylamino)-6-oxo-2-phenyl-5,7-diazaspiro[3.4]octan-7-yl)-4-methoxypyrimidine-2-carbonitrile
trans-2-(dimethylamino)-7-(2-(1,1-dioxidothiomorpholino)-2-oxoethyl)-2-phenyl-5,7-diazaspiro[3.4]octan-6-one
trans-5-(2-(dimethylamino)-6-oxo-2-phenyl-5,7-diazaspiro[3.4]octan-7-yl)-4-methoxypyrimidine-2-carbonitrile
cis-5-(cyclobutylmethyl)-2-(dimethylamino)-7-(2-(1,1-dioxidothiomorpholino)-2-oxoethyl)-2-phenyl-5,7-diazaspiro[3.4]octan-6-one
trans-5-(cyclobutylmethyl)-2-(dimethylamino)-7-(2-(1,1-dioxidothiomorpholino)-2-oxoethyl)-2-phenyl-5,7-diazaspiro[3.4]octan-6-one
cis-2-(5-(cyclobutylmethyl)-2-(dimethylamino)-6-oxo-2-phenyl-5,7-diazaspiro[3.4]octan-7-yl-)acetamide
trans-2-(5-(cyclobutylmethyl)-2-(dimethylamino)-6-oxo-2-phenyl-5,7-diazaspiro[3.4]octan-7-yl)-acetamide cis-5-(5-(cyclobutylmethyl)-2-(dimethylamino)-6-oxo-2-phenyl-5,7-diazaspiro[3.4]octan-7-yl)-4-methoxypyrimidine-2-carbonitrile
trans-5-(5-(cyclobutylmethyl)-2-(dimethylamino)-6-oxo-2-phenyl-5,7-diazaspiro[3.4]octan-7-yl)-4-methoxypyrimidine-2-carbonitrile
cis-2-(dimethylamino)-7-(4-methyl-2-morpholin-4-ylpyrimidin-5-yl)-2-phenyl-5,7-diazaspiro-[3.4]octan-6-one
cis-7-(6-(azetidin-1-yl)-4-methylpyridin-3-yl)-2-(dimethylamino)-2-phenyl-5,7-diazaspiro[3.4]octan-6-one
cis-5-(2-(dimethylamino)-2-(3-fluorophenyl)-6-oxo-5,7-diazaspiro[3.4]octan-7-yl)-4-methyl-picolinonitrile
cis-5-(5-(cyclopropylmethyl)-2-(dimethylamino)-2-(3-fluorophenyl)-6-oxo-5,7-diazaspiro[3.4]octan-7-yl)-4-methylpicolinonitrile
cis-6-(5-(cyclopropylmethyl)-2-(dimethylamino)-2-(3-fluorophenyl)-6-oxo-5,7-diazaspiro[3.4]octan-7-yl)-5-methylnicotinonitrile
cis-2-(dimethylamino)-2-(3-fluorophenyl)-7-(5-(trifluoromethoxy)pyridin-2-yl)-5,7-diazaspiro[3.4]-octan-6-one
cis-5-(cyclopropylmethyl)-2-(dimetliylamino)-2-(3-fluorophenyl)-7-(5-(trifluoromethoxy)pyridin-2-yl)-5,7-diazaspiro[3.4]octan-6-one
cis-2-(dimethylamino)-7-(4-methyl-6-morpholinopyridin-3-yl)-2-phenyl-5,7-diazaspiro[3.4]octan-6-one
cis-2-(dimethylamino)-7-(6-(2-hydroxypropan-2-yl)-4-methylpyridin-3-yl)-2-phenyl-5,7-diazaspiro-[3.4]octan-6-one
cis-2-(dimethylamino)-7-(4-(2-hydroxypropan-2-yl)-2-methylphenyl)-2-phenyl-5,7-diazaspiro-[3.4]octan-6-one
cis-7-(6-(difluoromethyl)-4-methylpyridin-3-yl)-2-(dimethylamino)-2-(3-fluorophenyl)-5,7-diaza-spiro[3.4]octan-6-one
cis-2-(dimethylamino)-5-((3-fluorooxetan-3-yl)methyl)-2-(3-fluorophenyl)-7-(5-(trifluoromethoxy)-pyridin-2-yl)-5,7-diazaspiro[3.4]octan-6-one
cis-5-(cyclopropylmethyl)-7-(6-(difluoromethyl)-4-methylpyridin-3-yl)-2-(dimethylamino)-2-(3-fluorophenyl)-5,7-diazaspiro[3.4]octan-6-one
cis-2-(dimethylamino)-7-(2-morpholinopyrimidin-5-yl)-2-phenyl-5,7-diazaspiro[3.4]octan-6-one
cis-2-(dimethylamino)-5-((1-fluorocyclopropyl)methyl)-2-(3-fluorophenyl)-7-(5-(trifluoromethoxy)-pyridin-2-yl)-5,7-diazaspiro[3.4]octan-6-one
cis-2-(dimethylamino)-2-(3-fluorophenyl)-5-((1-hydroxycyclobutyl)methyl)-7-(5-(trifluoromethoxy)-pyridin-2-yl)-5,7-diazaspiro[3.4]octan-6-one
cis-5-(cyclopropylmethyl)-2-(dimethylamino)-2-(3-fluorophenyl)-7-(4-(2-hydroxypropan-2-yl)-phenyl)-5,7-diazaspiro[3.4]octan-6-one
cis-2-(dimethylamino)-5-((3-fluorooxetan-3-yl)methyl)-2-phenyl-7-(5-(trifluoromethoxy)pyridin-2-yl)-5,7-diazaspiro[3.4]octan-6-one
cis-5-(cyclopropylmethyl)-2-(dimethylamino)-2-(3-fluorophenyl)-7-((6-(trifluoromethyl)pyridin-3-yl)methyl)-5,7-diazaspiro[3.4]octan-6-one
cis-5-(cyclopropylmethyl)-2-(dimethylamino)-2-(3-fluorophenyl)-7-(2-(methylsulfonyl)ethyl)-5,7-diazaspiro[3.4]octan-6-one
cis-5-(cyclopropylmethyl)-2-(dimethylamino)-2-phenyl-7-(5-(trifluoromethoxy)pyridin-2-yl)-5,7-diazaspiro[3.4]octan-6-one
cis-5-(cyclopropylmethyl)-2-(dimethylamino)-7-((3-fluorooxetan-3-yl)methyl)-2-(3-fluorophenyl)-5,7-diazaspiro[3.4]octan-6-one
cis-5-(cyclopropylmethyl)-7-(6-cyclopropylpyridin-3-yl)-2-(dimethylamino)-2-phenyl-5,7-diaza-spiro[3.4]octan-6-one
cis-7-(6-cyclopropyl-4-methylpyridin-3-yl)-5-(cyclopropylmethyl)-2-(dimethylamino)-2-phenyl-5,7-diazaspiro[3.4]octan-6-one
cis-7-(6-cyclopropyl-4-methylpyridin-3-yl)-2-(dimethylamino)-5-((3-fluorooxetan-3-yl)methyl)-2-phenyl-5,7-diazaspiro[3.4]octan-6-one
cis-5-(cyclopropylmethyl)-2-(dimethylamino)-2-(3-fluorophenyl)-7-(2-methoxy-2-methylpropyl)-5,7-diazaspiro[3.4]octan-6-one
cis-2-(dimethylamino)-2-phenyl-7-(2-pyridin-4-ylpyrimidin-5-yl)-5,7-diazaspiro[3.4]octan-6-one
cis-5-(cyclopropylmethyl)-2-(dimethylamino)-2-phenyl-7-[5-(trifluoromethyl)pyridin-3-yl]-5,7-diazaspiro[3.4]octan-6-one
cis-5-[5-(cyclopropylmethyl)-2-(dimethylamino)-6-oxo-2-phenyl-5,7-diazaspiro[3.4]octan-7-yl]-3-(trifluoromethyl)pyridine-2-carbonitrile
cis-2-(dimethylamino)-2-(3-fluorophenyl)-7-(4-morpholinobenzyl)-5,7-diazaspiro[3.4]octan-6-one
cis-5-(cyclopropylmethyl)-2-(dimethylamino)-2-(3-fluorophenyl)-7-[(1-hydroxycyclobutyl)methyl]-5,7-diazaspiro[3.4]octan-6-one
cis-5-(cyclopropylmethyl)-2-(dimethylamino)-2-phenyl-7-(2-pyridin-4-ylpyrimidin-5-yl)-5,7-diazaspiro[3.4]octan-6-one
cis-3-(5-(cyclopropylmethyl)-2-(dimethylamino)-2-(3-fluorophenyl)-6-oxo-5,7-diazaspiro[3.4]octan-7-yl)propanenitrile
cis-3-[5-(cyclopropylmethyl)-2-(dimethylamino)-6-oxo-2-phenyl-5,7-diazaspiro[3.4]octan-7-yl]-propanenitrile
cis-5-(cyclopropylmethyl)-2-(dimethylamino)-7-[(1-hydroxycyclobutyl)methyl]-2-phenyl-5,7-diaza-spiro[3.4]octan-6-one
cis-5-(cyclopropylmethyl)-2-(dimethylamino)-2-(3-fluorophenyl)-7-[2-(oxetan-3-yl)ethyl]-5,7-diaza-spiro[3.4]octan-6-one and the physiologically acceptable salts thereof.

In a preferred embodiment, the compounds according to the invention are in the form of the free bases.

In another preferred embodiment, the compounds according to the invention are in the form of the physiologically acceptable salts.

For the purposes of the description, a "salt" is to be understood as being any form of the compound in which it assumes an ionic form or is charged and is coupled with a counter-ion (a cation or anion) or is in solution. The term is also to be understood as meaning complexes of the compound with other molecules and ions, in particular complexes which are associated via ionic interactions. Preferred salts are physiologically acceptable, in particular physiologically acceptable salts with anions or acids or also a salt formed with a physiologically acceptable acid.

Physiologically acceptable salts with anions or acids are salts of the particular compound in question with inorganic or organic acids which are physiologically acceptable, in particular when used in humans and/or mammals. Examples of physiologically acceptable salts of particular acids include but are not limited to salts of hydrochloric acid, sulfuric acid, and acetic acid.

The invention also includes isotopic isomers of a compound according to the invention, wherein at least one atom of the compound is replaced by an isotope of the respective atom which is different from the naturally predominantly occurring isotope, as well as any mixtures of isotopic isomers of such a compound. Preferred isotopes are $^2$H (deuterium), $^3$H (tritium), $^{13}$C and $^{14}$C.

Certain compounds according to the invention are useful for modulating a pharmacodynamic response from one or more opioid receptors (mu, delta, kappa, NOP/ORL-1) either centrally or peripherally, or both. The pharmacodynamic response may be attributed to the compound either stimulating (agonizing) or inhibiting (antagonizing) the one or more receptors. Certain compounds according to the invention may antagonize one opioid receptor, while also agonizing one or more other receptors. Compounds according to the invention having agonist activity may be either full agonists or partial agonists.

As used herein, compounds that bind to receptors and mimic the regulatory effects of endogenous ligands are defined as "agonists". Compounds that bind to a receptor but produce no regulatory effect, but rather block the binding of ligands to the receptor, are defined as "antagonists".

In certain embodiments, the compounds according to the invention are agonists at the mu opioid (MOP) and/or kappa opioid (KOP) and/or delta opioid (DOP) and/or nociceptin opioid (NOP/ORL-1) receptors.

The compounds according to the invention potently bind to the MOP and/or KOP and/or DOP and/or NOP receptors.

The compounds according to the invention can be modulators at the MOP and/or KOP and/or DOP and/or NOP receptors, and therefore the compounds according to the invention can be used/administered to treat, ameliorate, or prevent pain.

In some embodiments, the compounds according to the invention are agonists of one or more opioid receptors. In some embodiments, the compounds according to the invention are agonists of the MOP and/or KOP and/or DOP and/or NOP receptors.

In some embodiments, the compounds according to the invention are antagonists of one or more opioid receptors. In some embodiments, the compounds according to the invention are antagonists of the MOP and/or KOP and/or DOP and/or NOP receptors.

In some embodiments, the compounds according to the invention have both, (i) agonist activity at the NOP receptor; and (ii) agonist activity at one or more of the MOP, KOP, and DOP receptors.

In some embodiments, the compounds according to the invention have both, (i) agonist activity at the NOP receptor; and (ii) antagonist activity at one or more of the MOP, KOP, and DOP receptors.

In some embodiments, the compounds according to the invention have both, (i) antagonist activity at the NOP receptor; and (ii) agonist activity at one or more of the MOP, KOP, and DOP receptors.

In some embodiments, the compounds according to the invention have both, (i) antagonist activity at the NOP receptor; and (ii) antagonist activity at one or more of the MOP, KOP, and DOP receptors.

In some embodiments, preferably with respect to receptors of the peripheral nervous system, the compounds according to the invention have selective agonist activity at the NOP receptor. In some embodiments, preferably with respect to receptors of the peripheral nervous system, the compounds according to the invention

- have agonist activity at the NOP receptor, but no significant activity at the MOP receptor;
- have agonist activity at the NOP receptor, but no significant activity at the KOP receptor;
- have agonist activity at the NOP receptor, but no significant activity at the DOP receptor;
- have agonist activity at the NOP receptor, but no significant activity at the MOP receptor as well as no significant activity at the KOP receptor;
- have agonist activity at the NOP receptor, but no significant activity at the MOP receptor as well as no significant activity at the DOP receptor; or
- have agonist activity at the NOP receptor, but no significant activity at the MOP receptor as well as no significant activity at the KOP receptor as well as no significant activity at the DOP receptor.

In some embodiments, preferably with respect to receptors of the peripheral nervous system, the compounds according to the invention have balanced agonist activity at the NOP receptor as well as at the MOP receptor. In some embodiments, preferably with respect to receptors of the peripheral nervous system, the compounds according to the invention

- have agonist activity at the NOP receptor as well as agonist activity at the MOP receptor;
- have agonist activity at the NOP receptor as well as agonist activity at the MOP receptor as well as agonist activity at the KOP receptor;
- have agonist activity at the NOP receptor as well as agonist activity at the MOP receptor as well as agonist activity at the DOP receptor;
- can be regarded as opioid pan agonists, i.e. have agonist activity at the NOP receptor as well as agonist activity at the MOP receptor as well as agonist activity at the KOP receptor as well as agonist activity at the DOP receptor;
- have agonist activity at the NOP receptor as well as agonist activity at the MOP receptor, but no significant activity at the KOP receptor;
- have agonist activity at the NOP receptor as well as agonist activity at the MOP receptor, but no significant activity at the DOP receptor; or
- have agonist activity at the NOP receptor as well as agonist activity at the MOP receptor, but no significant activity at the KOP receptor as well as no significant activity at the DOP receptor.

In some embodiments, preferably with respect to receptors of the peripheral nervous system, the compounds according to the invention have balanced agonist activity at the NOP receptor as well as at the KOP receptor. In some embodiments, preferably with respect to receptors of the peripheral nervous system, the compounds according to the invention
- have agonist activity at the NOP receptor as well as agonist activity at the KOP receptor;
- have agonist activity at the NOP receptor as well as agonist activity at the KOP receptor as well as agonist activity at the MOP receptor;
- have agonist activity at the NOP receptor as well as agonist activity at the KOP receptor as well as agonist activity at the DOP receptor;
- have agonist activity at the NOP receptor as well as agonist activity at the KOP receptor, but no significant activity at the MOP receptor;
- have agonist activity at the NOP receptor as well as agonist activity at the KOP receptor, but no significant activity at the DOP receptor; or
- have agonist activity at the NOP receptor as well as agonist activity at the KOP receptor, but no significant activity at the MOP receptor as well as no significant activity at the DOP receptor.

In some embodiments, preferably with respect to receptors of the peripheral nervous system, the compounds according to the invention have balanced agonist activity at the NOP receptor as well as at the DOP receptor. In some embodiments, preferably with respect to receptors of the peripheral nervous system, the compounds according to the invention
- have agonist activity at the NOP receptor as well as agonist activity at the DOP receptor;
- have agonist activity at the NOP receptor as well as agonist activity at the DOP receptor, but no significant activity at the MOP receptor;
- have agonist activity at the NOP receptor as well as agonist activity at the DOP receptor, but no significant activity at the KOP receptor; or
- have agonist activity at the NOP receptor as well as agonist activity at the DOP receptor, but no significant activity at the MOP receptor as well as no significant activity at the KOP receptor.

In some embodiments, preferably with respect to receptors of the peripheral nervous system, the compounds according to the invention have selective agonist activity at the KOP receptor. In some embodiments, preferably with respect to receptors of the peripheral nervous system, the compounds according to the invention
- have agonist activity at the KOP receptor, but no significant activity at the MOP receptor;
- have agonist activity at the KOP receptor, but no significant activity at the NOP receptor;
- have agonist activity at the KOP receptor, but no significant activity at the DOP receptor;
- have agonist activity at the KOP receptor, but no significant activity at the MOP receptor as well as no significant activity at the NOP receptor;
- have agonist activity at the KOP receptor, but no significant activity at the MOP receptor as well as no significant activity at the DOP receptor; or
- have agonist activity at the KOP receptor, but no significant activity at the MOP receptor as well as no significant activity at the NOP receptor as well as no significant activity at the DOP receptor.

In some embodiments, preferably with respect to receptors of the peripheral nervous system, the compounds according to the invention have agonist activity at the MOP receptor, agonist activity at the KOP receptor, and antagonist activity at the DOP receptor. In some embodiments, preferably with respect to receptors of the peripheral nervous system, the compounds according to the invention
- have agonist activity at the MOP receptor as well as agonist activity at the KOP receptor as well as antagonist activity at the DOP receptor;
- have agonist activity at the MOP receptor as well as agonist activity at the KOP receptor as well as antagonist activity at the DOP receptor as well as agonist activity at the NOP receptor;
- have agonist activity at the MOP receptor as well as agonist activity at the KOP receptor as well as antagonist activity at the DOP receptor as well as antagonist activity at the NOP receptor; or
- have agonist activity at the MOP receptor as well as agonist activity at the KOP receptor as well as antagonist activity at the DOP receptor, no significant activity at the NOP receptor.

In some embodiments, preferably with respect to receptors of the central nervous system, the compounds according to the invention have selective agonist activity at the NOP receptor. In some embodiments, preferably with respect to receptors of the central nervous system, the compounds according to the invention
- have agonist activity at the NOP receptor, but no significant activity at the MOP receptor;
- have agonist activity at the NOP receptor, but no significant activity at the KOP receptor;
- have agonist activity at the NOP receptor, but no significant activity at the DOP receptor;
- have agonist activity at the NOP receptor, but no significant activity at the MOP receptor as well as no significant activity at the KOP receptor;
- have agonist activity at the NOP receptor, but no significant activity at the MOP receptor as well as no significant activity at the DOP receptor; or
- have agonist activity at the NOP receptor, but no significant activity at the MOP receptor as well as no significant activity at the KOP receptor as well as no significant activity at the DOP receptor.

In some embodiments, preferably with respect to receptors of the central nervous system, the compounds according to the invention have selective antagonist activity at the NOP receptor. In some embodiments, preferably with respect to receptors of the central nervous system, the compounds according to the invention
- have antagonist activity at the NOP receptor, but no significant activity at the MOP receptor;
- have antagonist activity at the NOP receptor, but no significant activity at the KOP receptor;
- have antagonist activity at the NOP receptor, but no significant activity at the DOP receptor;
- have antagonist activity at the NOP receptor, but no significant activity at the MOP receptor as well as no significant activity at the KOP receptor;
- have antagonist activity at the NOP receptor, but no significant activity at the MOP receptor as well as no significant activity at the DOP receptor; or
- have antagonist activity at the NOP receptor, but no significant activity at the MOP receptor as well as no significant activity at the KOP receptor as well as no significant activity at the DOP receptor.

In some embodiments, preferably with respect to receptors of the central nervous system, the compounds according to the invention have antagonist activity at the NOP receptor as well as agonist activity at the DOP receptor. In some embodiments, preferably with respect to receptors of the central nervous system, the compounds according to the invention
- have antagonist activity at the NOP receptor as well as agonist activity at the DOP receptor;
- have antagonist activity at the NOP receptor as well as agonist activity at the DOP receptor, but no significant activity at the MOP receptor;
- have antagonist activity at the NOP receptor as well as agonist activity at the DOP receptor, but no significant activity at the KOP receptor; or
- have antagonist activity at the NOP receptor as well as agonist activity at the DOP receptor, but no significant activity at the MOP receptor as well as no significant activity at the KOP receptor.

For the purpose of the specification, "no significant activity" means that the activity (agonist/antagonist) of the given compound at this receptor is lower by a factor of 1000 or more compared to its activity (agonist/antagonist) at one or more of the other opioid receptors.

A further aspect of the invention relates to the compounds according to the invention as medicaments.

A further aspect of the invention relates to the compounds according to the invention for use in the treatment of pain. A further aspect of the invention relates to a method of treating pain comprising the administration of a pain alleviating amount of a compound according to the invention to a subject in need GRA4090-US thereof, preferably to a human. The pain is preferably acute or chronic. The pain is preferably nociceptive or neuropathic.

A further aspect of the invention relates to the compounds according to the invention for use in the treatment of neurodegenerative disorders, neuroinflammatory disorders, neuropsychiatric disorders, and substance abuse/dependence. A further aspect of the invention relates to a method of treating any one of the aforementioned disorders, diseases or conditions comprising the administration of a therapeutically effective amount of a compound according to the invention to a subject in need thereof, preferably to a human.

Another aspect of the invention relates to a pharmaceutical composition which contains a physiologically acceptable carrier and at least one compound according to the invention.

Preferably, the composition according to the invention is solid, liquid or pasty; and/or contains the compound according to the invention in an amount of from 0.001 to 99 wt. %, preferably from 1.0 to 70 wt. %, based on the total weight of the composition.

The pharmaceutical composition according to the invention can optionally contain suitable additives and/or auxiliary substances and/or optionally further active ingredients.

Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik and angrenzende Gebiete, Editio Cantor Aulendoff).

The pharmaceutical composition according to the invention contains the compound according to the invention in an amount of preferably from 0.001 to 99 wt. %, more preferably from 0.1 to 90 wt. %, yet more preferably from 0.5 to 80 wt. %, most preferably from 1.0 to 70 wt. % and in particular from 2.5 to 60 wt. %, based on the total weight of the pharmaceutical composition.

The pharmaceutical composition according to the invention is preferably for systemic, topical or local administration, preferably for oral administration.

Another aspect of the invention relates to a pharmaceutical dosage form which contains the pharmaceutical composition according to the invention.

In one preferred embodiment, the pharmaceutical dosage form according to the invention is produced for administration twice daily, for administration once daily or for administration less frequently than once daily.

Administration is preferably systemic, in particular oral.

The pharmaceutical dosage form according to the invention can be administered, for example, as a liquid dosage form in the form of injection solutions, drops or juices, or as a semi-solid dosage form in the form of granules, tablets, pellets, patches, capsules, plasters/spray-on plasters or aerosols. The choice of auxiliary substances etc. and the amounts thereof to be used depend on whether the form of administration is to be administered orally, perorally, parenterally, intravenously, intraperitoneally, intradermally, intramuscularly, intranasally, buccally, rectally or locally, for example to the skin, the mucosa or into the eyes.

Pharmaceutical dosage forms in the form of tablets, dragees, capsules, granules, drops, juices and syrups are suitable for oral administration, and solutions, suspensions, readily reconstitutable dry preparations and also sprays are suitable for parenteral, topical and inhalatory administration. Compounds according to the invention in a depot, in dissolved form or in a plaster, optionally with the addition of agents promoting penetration through the skin, are suitable percutaneous administration preparations.

The amount of the compounds according to the invention to be administered to the patient varies in dependence on the weight of the patient, on the type of administration, on the indication and on the severity of the disease. Usually, from 0.00005 mg/kg to 50 mg/kg, preferably from 0.001 mg/kg to 10 mg/kg, of at least one compound according to the invention is administered.

Another aspect of the invention relates to a process for the preparation of the compounds according to the invention. Suitable processes for the synthesis of the compounds according to the invention are known in principle to the person skilled in the art.

EXAMPLES

The following examples further illustrate the invention but are not to be construed as limiting its scope.

"RT" means room temperature (23±7° C.), "M" are indications of concentration in mol/l, "aq." means aqueous, "sat." means saturated, "sol." means solution, "conc." means concentrated.

Further Abbreviations brine saturated aqueous sodium chloride solution
Boc$_2$O di-tert-butyl dicarbonate
Bu butyl
DCM dichloromethane
DIPEA N,N-diisopropylethylamine
DMSO dimethylsulfoxide
DMF N,N-dimethylformamide
Pd$_2$(dba)$_3$ tris(dibenzylideneacetone)dipalladium(0)
Et ethyl
ether diethyl ether
EtOAc ethyl acetate
EtOH ethanol
h hour(s)
HATU O-(7-aza-benzotriazol-1-yl)-N,N,N',N'-tetramethyluroniumhexafluorophosphate LDA lithium diisoproylamide
Me methyl
m/z mass-to-charge ratio
MeOH methanol
MeCN acetonitrile
min minutes
MS mass spectrometry
NBS N-bromosuccinimide
NIS N-iodosuccinimide
NEt₃ triethylamine
TFA trifluoroacetic acid
T3P 2,4,6-tripropyl- 1,3,5,2,4,6-trioxatriphosphorinane-2,4,6-trioxide
THF tetrahydrofurane
v/v volume to volume
w/w weight to weight
Xantphos 4,5-bis(diphenylphosphino)-9,9-dimethylxanthene The yields of the compounds prepared were not optimised. All temperatures are uncorrected.

All starting materials, which are not explicitly described, were either commercially available (the details of suppliers such as for example Acros, Aldrich, Bachem, Butt park, Enamine, Fluka, Lancaster, Maybridge, Merck, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The mixing ratios of solvents or eluents for chromatography are specified in v/v.

All the intermediate products and exemplary compounds were analytically characterised by mass spectrometry (MS, m/z for [M+H]⁺). In addition ¹H-NMR and ¹³C spectroscopy was carried out for all the exemplary compounds and selected intermediate products.

Synthetic Procedures for the Preparation of Intermediates

General Scheme for the Synthesis of INT-7 and INT-8

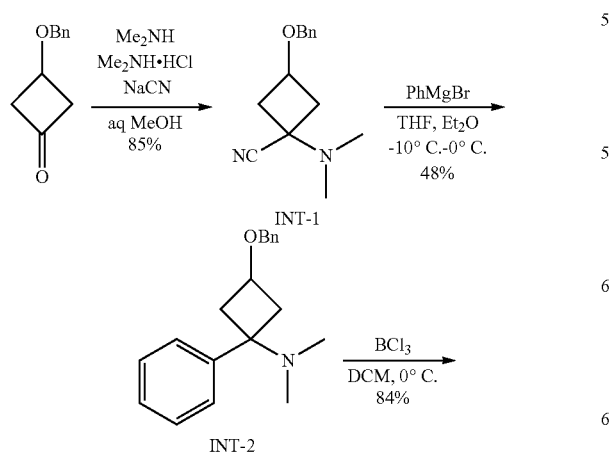

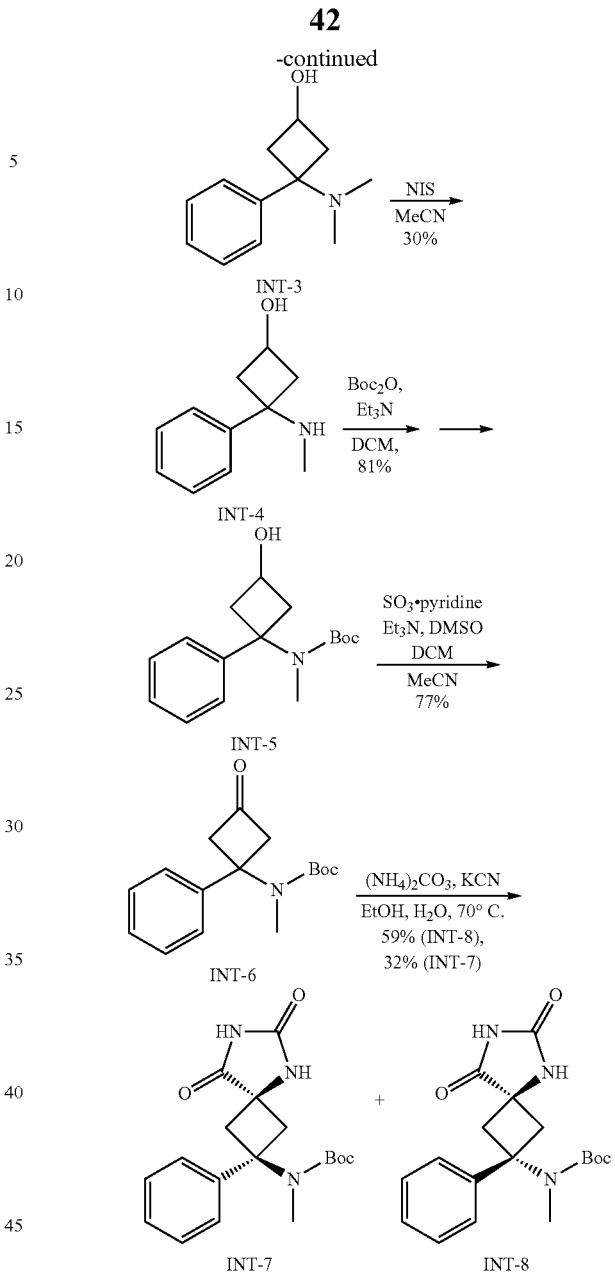

3-(Benzyloxy)-1-(dimethylamino)cyclobutanecarbonitrile (INT-1)

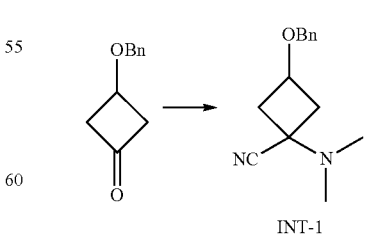

This reaction was carried out under N₂ in a 5 L 3-neck round bottom flask. To 3-(benzyloxy)cyclobutan-1-one (88 g, 499 mmol) was added MeOH (88 mL), followed by Me₂NH·HCl (116 g, 1423 mmol). After stirring at RT for 10 min, 40% aqueous Me₂NH (626 mL, 4939 mmol) was added followed by NaCN (26.9 g, 549 mmol). The reaction mixture was stirred at RT overnight. The reaction mixture was diluted with sat aq NaHCO₃ (400 mL) and water (400 mL) and extracted with EtOAc (4×800 mL). The combined organic extracts were dried over Na₂SO₄, filtered, and the filtrate was concentrated under reduced pressure. The residue was co-evaporated twice with THF affording 3-(benzyloxy)-1-(dimethylamino)cyclobutanecarbonitrile (INT-1) (122.9 g (80% pure), 427 mmol, 85%) as a brown oil which was used in the next step without further purification. LCMS: calculated for [M+H]⁺=231.2, found 231.1.

3-(Benzyloxy)-N,N-dimethyl-1-phenylcyclobutanamine (INT-2)

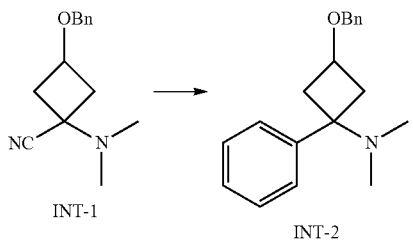

This reaction was carried out under N₂. The reaction flask was dried (heat-gun) before use. 3 M PhMgBr in Et₂O (1.423 L, 4269 mmol) was cooled to −10° C. A solution of 3-(benzyloxy)-1-(dimethylamino)cyclobutanecarbonitrile (INT-1) (122.9 g (80% pure), 427 mmol) in dry THF (1.0 L) was added dropwise over ca. 70 min at −10° C. and stirring at −10° C. to 0° C. was continued for 3 h after complete addition of the starting material. Upon cooling on ice bath, the reaction mixture was carefully quenched by the dropwise addition of a solution of 660 g of NH₄Cl (12.3 mol) in H₂O (2.6 L). After complete addition, EtOAc (1.7 L) was added, the mixture was stirred for 30 min and the layers were separated. EtOAc (1.7 L) was added to the aqueous phase and the mixture was stirred for 30 min and left standing overnight. Layers were separated. EtOAc (1.7 L) was added to the aqueous phase, the mixture was stirred for 30 min and the layers were separated. EtOAc (1.7 L) was added to the aqueous phase and the mixture was stirred for 30 min and the layers were separated. All organic layers were combined and evaporated under reduced pressure. The product was purified by column chromatography (1.2 kg silica, heptane/EtOAc, 9:1-1:1-1:2-0:1), to give 58.15 g (207 mmol, 48.4%) of 3-(benzyloxy)-N,N-dimethyl-1-phenylcyclobutanamine (INT-2). LCMS: calculated for [M+H]⁺=282.2, found 282.2.

3-(Dimethylamino)-3-phenylcyclobutanol (INT-3)

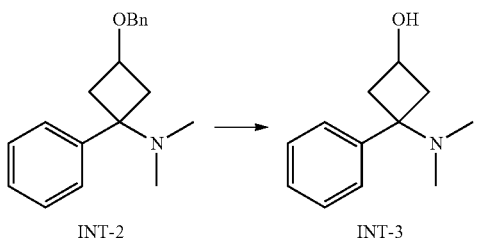

This reaction was carried out under N₂. At 0 OC, 1 M BCl₃ in DCM (349 mL, 349 mmol) was added dropwise over ca. 45 min to a solution of 3-(benzyloxy)-N,N-dimethyl-1-phenylcyclobutanamine (INT-2) (65.39 g, 232 mmol) in DCM (650 mL). Stirring at 0° C. was continued for 30 min. More 1 M BCl₃ in DCM (349 mL, 349 mmol) was added dropwise over 45 min and stirring was continued at 0° C. for 1 h. MeOH (ca. 200 mL) was added dropwise at 0° C. and the solvent was removed under reduced pressure at 30° C. The crude product was concentrated again from MeOH (3×). The crude product was dissolved in DCM (200 mL) and MeOH (200 mL).

Silica (200 g) was added and the solvent was removed under reduced pressure. The product was purified by column chromatography (silica, DCM/(7M NH₃ in MeOH), 1:0-98:2-95:5-93:7-9:1), to obtain 3-(dimethylamino)-3-phenylcyclobutanol (INT-3) (37.53 g, 196 mmol, 84%). LCMS: calculated for [M+H]⁺=192.1, found 192.2.

3-(Methylamino)-3-phenylcyclobutanol (INT-4)

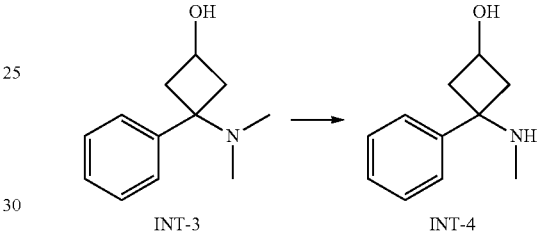

To 3-(dimethylamino)-3-phenylcyclobutanol (INT-3) (44.44 g, 232 mmol) was added dry MeCN (2.25 L) and the resulting suspension was stirred at RT overnight to dissolve most of the starting material. N-iodosuccinimide (57.5 g, 256 mmol) was added portionwise over ca. 10 min and the reaction mixture was stirred at RT for 2 t More N-iodosuccinimide (15.68 g, 69.7 mmol) was added portionwise over ca. 5 min and stirring at RT was continued for 2.5 h. The solvent was removed under reduced pressure. The crude product was purified by column chromatography (silica, DCM/(7M NH₃ in MeOH), 1:0-98:2-95:5-9:1) to give a reasonably pure batch of 3-(methylamino)-3-phenylcyclobutanol (INT-4) (8.19 g (73% pure), 33.7 mmol, 14.5%) and a very impure batch of INT-4 (78 g (ca. 9% pure)). The very impure batch was purified further by column chromatography (silica, DCM/MeOH/Et₃N, 90:9:1) to give another batch of INT-4 (27.7 g (23% pure), 35.9 mmol, 15.5%). Total yield: 30%. LCMS: calculated for [M+H]⁺=178.1, found 178.2.

Tert-butyl (3-hydroxy-1-phenylcyclobutyl)(methyl)carbamate (INT-5)

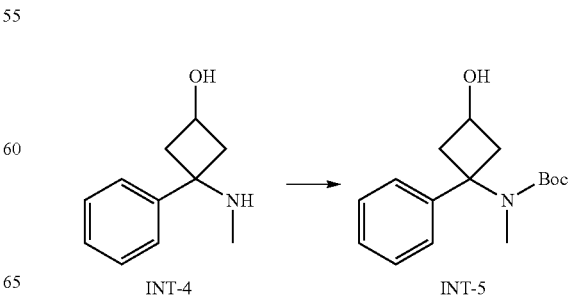

To a solution of 3-(methylamino)-3-phenylcyclobutanol (INT-4) (8.15 g (73% pure), 33.6 mmol) and Et₃N (23.39 mL, 168 mmol) in DCM (50 mL) was added Boc₂O (8.06 g, 36.9 mmol) and the reaction mixture was stirred at RT overnight. More Boc₂O (8.06 g, 36.9 mmol) was added and stirring at RT was continued for 6 h. The solvent was removed under reduced pressure. The product was purified by column chromatography (1 kg silica, DCM/MeOH, 1:0-98:2), to afford a pure batch of tert-butyl (3-hydroxy-1-phenylcyclobutyl)(methyl)carbamate (INT-5) (5.89 g, 21.2 mmol, 63.3%) and an impure batch of INT-5 (2.36 g (71% pure), 6.04 mmol, 18.0%). Total yield: 81%. LCMS: calculated for [M+H-$^t$Bu]$^+$=222.1, found 222.1.

Tert-butyl methyl(3-oxo-1-phenylcyclobutyl)carbamate (INT-6)

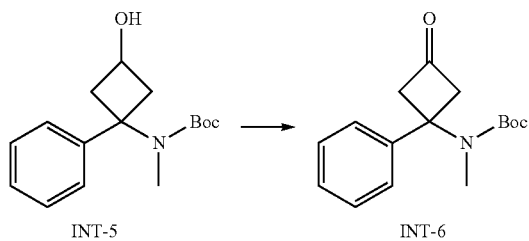

To a solution of tert-butyl (3-hydroxy-1-phenylcyclobutyl)(methyl)carbamate (INT-5) (5.89 g, 21.24 mmol) in DCM (90 mL) was added Et₃N (17.76 mL, 127 mmol) and DMSO (12.06 mL, 170 mmol) followed by pyridine SO₃ (10.14 g, 63.7 mmol). The reaction mixture was stirred at RT overnight. Sat. aq. NH₄Cl (50 mL) and water (50 mL) was added. Layers were separated and the aqueous layer was extracted with DCM (60 mL). Organic layers were combined, washed with sat. aq. NaHCO₃ (100 mL), dried over Na₂SO₄ and evaporated under reduced pressure. The crude product was purified by flash chromatography (120 g silica, gradient heptane/EtOAc, 95:5-3:2). The resulting product was concentrated from EtOH to afford tert-butyl methyl(3-oxo-1-phenylcyclobutyl)carbamate (INT-6) (4.50 g, 16.34 mmol, 77%). LCMS: calculated for [M+H-$^t$Bu]$^+$=220.1, found 220.1.

Tert-butyl cis-(6,8-dioxo-2-phenyl-5,7-diazaspiro [3.4]octan-2-yl)(methyl)carba-mate (INT-7) and tert-butyl trans-(6,8-dioxo-2-phenyl-5,7-diazaspiro [3.4]octan-2-yl)(methyl)carbamate (INT-8)

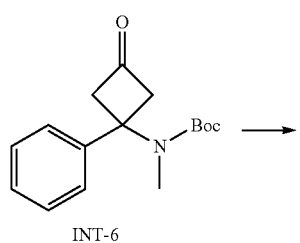

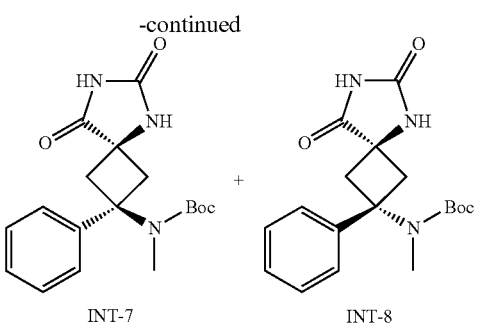

This reaction was carried out in a closed system (500 mL glass Parr system). To a mixture of (NH₄)₂CO₃ (13.09 g, 136 mmol) and KCN (1.774 g, 27.2 mmol) was added a solution of tert-butyl methyl(3-oxo-1-phenylcyclobutyl)carbamate (INT-6) (7.5 g, 27.2 mmol) in EtOH (60 mL). H₂O (60 mL) was added and the reaction mixture was stirred at 70° C. overnight. The white suspension was allowed to cool to RT. Crushed ice (~60 mL) was added and the obtained mixture was filtered over a sintered glass filter (P3). The flask was rinsed with a mixture of EtOH/H₂O (50 mL, 1/1, v/v), which was also filtered. To the combined filtrate was added aq. sat. NaHCO₃ (300 mL) and the mixture was extracted with DCM (3×300 mL). The combined organic layers were dried (Na₂SO₄) and concentrated. Purification by flash chromatography (220 g silica, gradient heptane/EtOAc, 3:2→0:1) followed by co-evaporation with Et₂O (2×30 mL) afforded tert-butyl trans-(6,8-dioxo-2-phenyl-5,7-diazaspiro[3.4]octan-2-yl)(methyl)carbamate (INT-8) (5.53 g, 16.01 mmol, 59%). LCMS: calculated for [M−H]$^-$=344.2, found 344.2. The residue on the glass filter was washed with a mixture of EtOH/H₂O (120 mL, 1/1, v/v) and was dried on the filter by vacuum under a N₂ stream to yield tert-butyl cis-(6,8-dioxo-2-phenyl-5,7-diazaspiro[3.4]octan-2-yl)(methyl)carbamate (INT-7) (3.05 g, 8.83 mmol, 32%). LCMS: calculated for [M−H]$^-$=344.2, found 344.2.

General Scheme for the Synthesis of INT-13

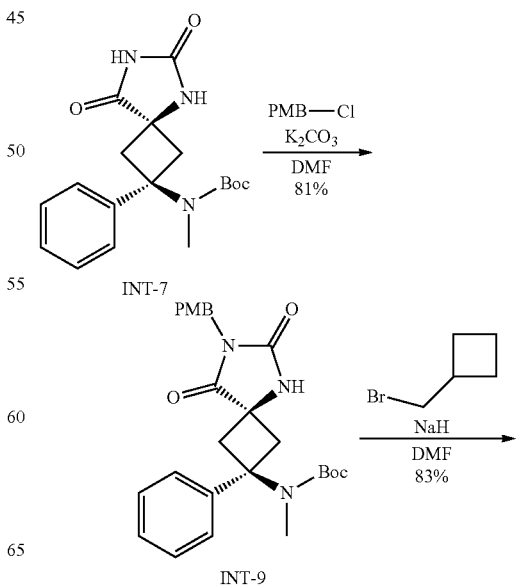

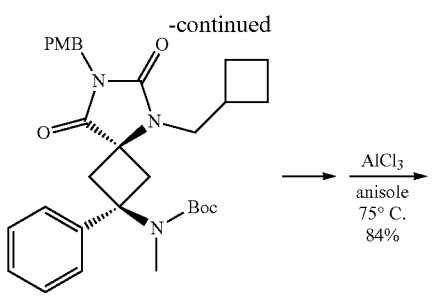

INT-10

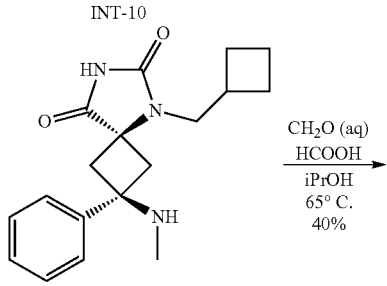

INT-11

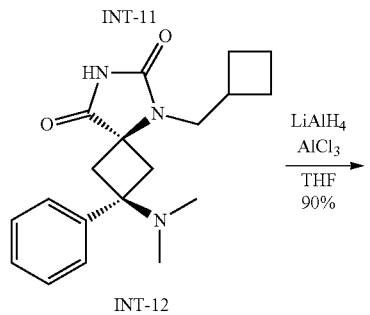

INT-12

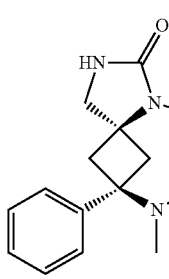

INT-13

Tert-butyl cis-(7-(4-methoxybenzyl)-6,8-dioxo-2-phenyl-5,7-diazaspiro [3.4]-octan-2-yl)(methyl)-carbamate (INT-9)

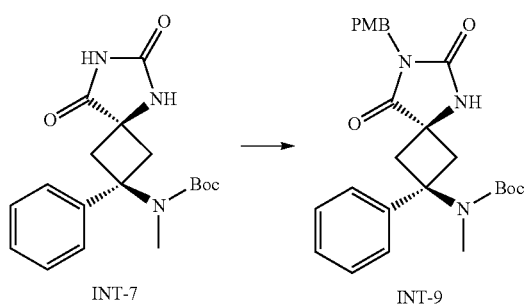

aspiro[3.4]octan-2-yl)(methyl)carbamate (INT-7) (0.3 g, 0.869 mmol) and 4-methoxybenzyl chloride (0.124 mL, 0.912 mmol) in anhydrous DMF (15 mL) was added $K_2CO_3$ (0.126 g, 0.912 mmol) and the mixture was stirred at RT overnight. Additional $K_2CO_3$ (0.012 g, 0.087 mmol) and 4-methoxybenzyl chloride (0.012 mL, 0.087 mmol) were added and the mixture was stirred at RT for another 4 h. The reaction mixture was partitioned between brine (200 mL) and EtOAc (100 mL). The water layer was extracted with EtOAc (3×100 mL). Combined organic layers were washed with brine (3×100 mL) and dried over $Na_2SO_4(s)$. In vacuo concentration gave a colourless oil as crude product. This experiment was repeated in the same way using 1.62 g (4.68 mmol) of tert-butyl cis-(6,8-dioxo-2-phenyl-5,7-diazaspiro [3.4]octan-2-yl)(methyl)carbamate (INT-7). The obtained crude products were combined for purification by flash chromatography (120 g silica, gradient heptane/EtOAc, 20:1-3:7) and afforded tert-butyl cis-(7-(4-methoxybenzyl)-6,8-dioxo-2-phenyl-5,7-diazaspiro[3.4]-octan-2-yl)(methyl) carbamate (INT-9) (2.09 g, 4.489 mmol, 81%). LCMS: calculated for $[M+H]^+$=466.5, found 466.3.

Tert-butyl cis-(5-(cyclobutylmethyl)-7-(4-methoxy-benzyl)-6,8-dioxo-2-phenyl-5,7-diaza-spiro[3.4] octan-2-yl)(methyl)carbamate (INT-10)

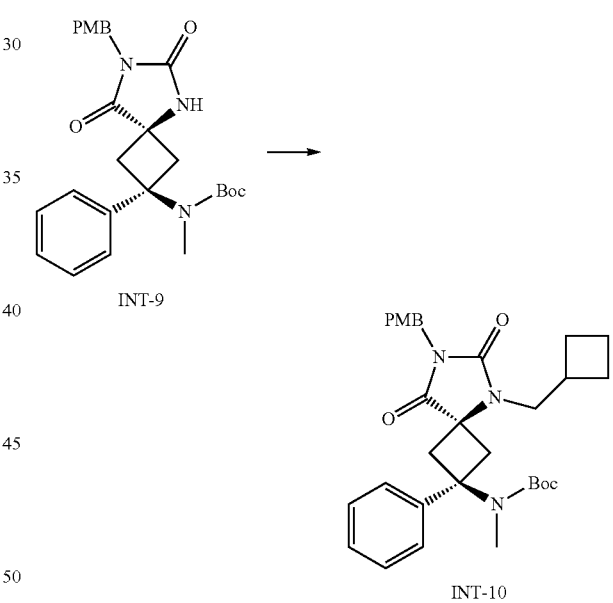

Dry glassware and argon atmosphere were used. To a solution of tert-butyl cis-(7-(4-methoxybenzyl)-6,8-dioxo-2-phenyl-5,7-diazaspiro[3.4]-octan-2-yl)(methyl)carbamate (INT-9) (200 mg, 0.430 mmol) in anhydrous DMF (8 mL) was added 60% NaH in mineral oil (34.4 mg, 0.859 mmol) and the mixture was stirred at RT until gas evolution ceased. Then, (bromomethyl)cyclobutane (0.191 mL, 1.718 mmol) was added and stirring was continued at RT for 4 h. The reaction mixture was cooled in an ice-bath and carefully quenched with water (2 mL) and diluted with brine (100 mL) and EtOAc (20 mL). Layers were partitioned and the water layer was extracted with EtOAc (3×20 mL). Combined organic layers were washed with brine and dried over $Na_2SO_4(s)$. Filtration followed by in vacuo filtrate concentration gave a colorless oil as crude product. This experiment Dry glassware and argon atmosphere were used. To a suspension of tert-butyl cis-(6,8-dioxo-2-phenyl-5,7-diazwas repeated in the same way using 1.81 g (3.89 mmol) of tert-butyl cis-(7-(4-methoxybenzyl)-6,8-dioxo-2-phenyl-5,7-diazaspiro[3.4]-octan-2-yl)(methyl)carba-mate (INT-9). However, quenching was performed with MeOH (1 mL) instead of water. The obtained crude products were combined for purification by flash chromatography (120 g silica, gradient heptane/EtOAc, 9:1-1:1), which afforded tert-butyl cis-(5-(cyclobutylmethyl)-7-(4-methoxybenzyl)-6,8-dioxo-2-phenyl-5,7-diazaspiro[3.4]octan-2-yl)(methyl)carbamate (INT-10) (1.92 g, 3.587 mmol, 83%) as a white foamy solid. LCMS: calculated for [M+H]⁺=534.7, found 534.4.

Cis-5-(cyclobutylmethyl)-2-(methylamino)-2-phenyl-5,7-diazaspiro[3.4]octane-6,8-dione (INT-11)

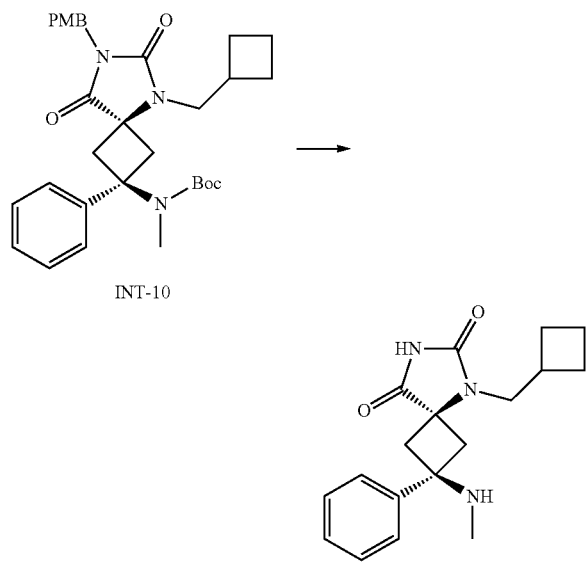

Dry glassware and an inert atmosphere (Ar(g)) were used. To a solution of tert-butyl cis-(5-(cyclobutylmethyl)-7-(4-methoxybenzyl)-6,8-dioxo-2-phenyl-5,7-diazaspiro[3.4]octan-2-yl)(methyl)carbamate (INT-10) (2.022 g, 3.79 mmol) in extra dry anisole (60 mL) was added AlCl₃ (2.53 g, 18.94 mmol) and the resulting colourless solution was stirred at 75° C. for 1.5 h. Then after cooling down to RT, additional AlCl₃ (2.53 g, 18.94 mmol) was added and stirring at 75° C. was continued overnight. The reaction mixture was cooled down to RT and quenched by adding the reaction mixture to sat. aq. Na₂CO₃ (400 mL). Brine (150 mL) and EtOAc (400 mL) were added and the layers were separated. The aqueous phase was extracted with EtOAc (3×100 mL). The combined organic layers were washed with brine (200 mL) and dried over Na₂SO₄(s). Filtration followed by in vacuo filtrate concentration gave a brown oil as crude product. The obtained crude product was loaded onto silica and purified by flash chromatography (120 g silica, gradient heptane/EtOAc, 3:1→3:7) which afforded cis-5-(cyclobutylmethyl)-2-(methylamino)-2-phenyl-5,7-diazaspiro[3.4]octane-6,8-dione (INT-11) (998 mg, 3.185 mmol, 84%) as a yellowish solid. LCMS: calculated for [M+H]⁺=314.4, found 314.2. ¹H-NMR (400 MHz, CDCl₃) δ 7.62 (bs, 1H), 7.36 (t, J=7.5 Hz, 2H), 7.30-7.19 (m, 3H), 3.80 (d, J=7.4 Hz, 2H), 3.07 (d, J=14.2 Hz, 2H), 2.85 (m, 1H), 2.56 (d, J=14.2 Hz, 2H), 2.07 (m, 5H), 1.89 (m, 4H).

Cis-5-(cyclobutylmethyl)-2-(dimethylamino)-2-phenyl-5,7-diazaspiro[3.4]-octane-6,8-dione (INT-12)

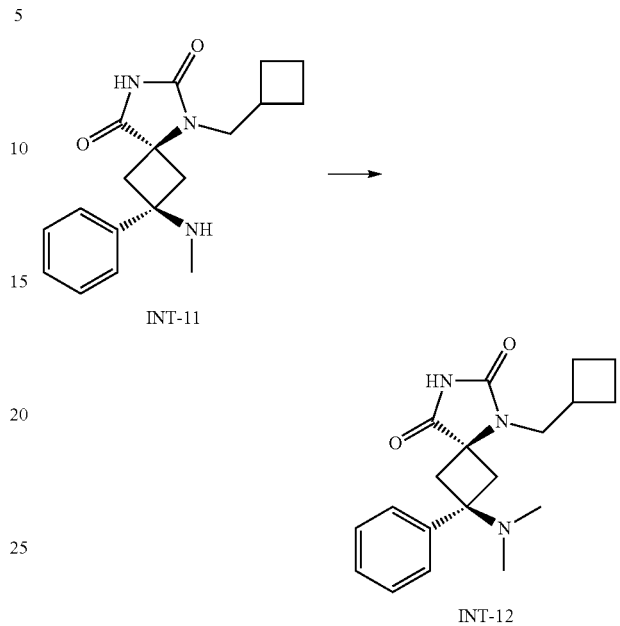

To a solution of cis-5-(cyclobutylmethyl)-2-(methylamino)-2-phenyl-5,7-diazaspiro[3.4]octane-6,8-dione (INT-11) (200 mg, 0.638 mmol) in 2-propanol (10 mL) was added slowly formic acid (0.240 mL, 6.38 mmol) and the mixture was stirred at 65° C. At the same temperature, 37% aqueous formaldehyde (0.480 mL, 6.38 mmol) was added at once and stirring was continued at the same temperature overnight. The reaction mixture was cooled down to RT and the reaction was carefully quenched with sat. aq. NaHCO₃. The mixture was then diluted with brine and DCM. Layers were separated using a phase separator and the aqueous phase was extracted with DCM (2×15 mL). The combined organic layers were concentrated under reduced pressure to afford the crude product as a brownish sticky oil. The crude product was subjected to a purification by flash column chromatography (12 g silica, gradient DCM/MeOH, 199:1→97:3) affording a more pure product.

Subsequently, this material was subjected to a second purification by preparative HPLC (HPLC instrument type: Agilent Technologies 1200 preparative LC; column: Waters XSelect CSH (C18, 150×25 mm, 10); flow: 43 mL/min; column temp: RT; eluent A: 99% acetonitrile+1% 10 mM ammonium bicarbonate in water pH=9.0, eluent B: 10 mM ammonium bicarbonate in water pH=9.0; lin. gradient: t=0 min 20% A, t=2.5 min 20% A, t=11 min 60% A, t=13 min 100% A, t=17 min 100% A; detection: DAD (210 nm)) to obtain cis-5-(cyclobutylmethyl)-2-(dimethylamino)-2-phenyl-5,7-diazaspiro[3.4]-octane-6,8-dione (INT-12) as a white solid (98 mg, 0.30 mmol, 47%). LCMS: calculated for [M+H]⁺=328.4, found 328.2. ¹H-NMR (400 MHz, CDCl₃) 7.35 (m, 3H), 7.28 (m, 1H), 7.05-7.03 (m, 2H), 3.71 (d, J=7.4 Hz, 2H), 3.02 (d, J=14.0 Hz, 2H), 2.86-2.78 (m, 1H), 2.71 (d, J=14.0 Hz, 2H), 2.12-2.06 (m, 2H), 1.94 (s, 6H), 1.94-1.77 (m, 4H).

Cis-5-(cyclobutylmethyl)-2-(dimethylamino)-2-phenyl-5,7-diazaspiro[3.4]-octan-6-one (INT-13)

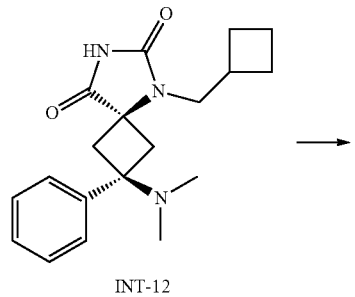

INT-12

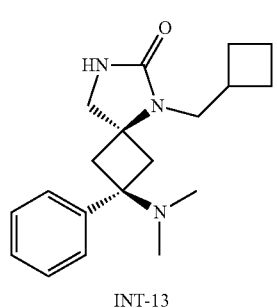

INT-13

Oven dried glassware and an inert atmosphere were used. To an ice-bath cooled solution of AlCl$_3$ (586 mg, 4.40 mmol) in dry THF (8 mL) was carefully and dropwise added 2.4 M LiAlH$_4$ in THF (1.374 mL, 3.30 mmol) and the reaction mixture was stirred at RT for 30 min. Then, the mixture was re-cooled in an ice-bath and a solution of cis-5-(cyclobutylmethyl)-2-(dimethylamino)-2-phenyl-5,7-diazaspiro[3.4]-octane-6,8-dione (INT-12) (360 mg, 1.099 mmol) in dry THF (14 mL) was added dropwise. The mixture was stirred at the same temperature for 1 h and at RT for 3 h. The reaction mixture was cooled in an ice bath and the reaction was carefully quenched by the dropwise addition of water (20 mL). Aqueous 1 M NaOH (30 mL) and DCM (25 mL) were added and the layers were separated using a phase separator. The water layer was extracted with DCM (4×10 mL). In vacuo concentration of the combined organic layers gave the crude product as a white solid. The obtained crude product was purified by flash chromatography (40 g silica, gradient DCM/MeOH, 199:1-93:7) and afforded cis-5-(cyclobutylmethyl)-2-(dimethylamino)-2-phenyl-5,7-diazaspiro[3.4]-octan-6-one (INT-13) (311 mg, 0.992 mmol, 90%). LCMS: calculated for [M+H]$^+$=314.4, found 314.3. $^1$H NMR (400 MHz, CDCl$_3$) δ: 7.37 (m, 2H), 7.33-7.27 (m, 1H), 7.25-7.18 (m, 2H), 4.12 (s, 1H), 3.29 (d, J=7.3 Hz, 2H), 2.85 (d, J=1.2 Hz, 2H), 2.72-2.59 (m, 3H), 2.58-2.49 (m, 2H), 2.03 (m, 2H), 1.94 (s, 6H), 1.90-1.76 (m, 4H).

Cis-2-(dimethylamino)-2-phenyl-5,7-diazaspiro[3.4] octan-6-one (INT-14)

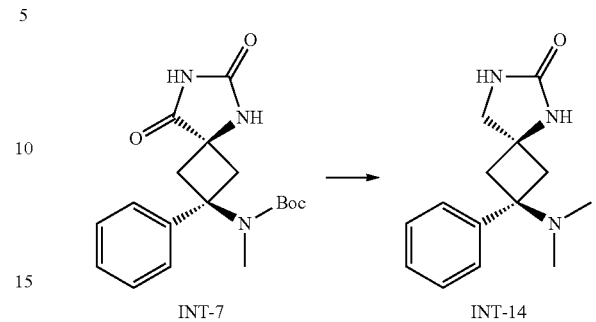

To a cooled (0° C.) suspension of tert-butyl cis-(6,8-dioxo-2-phenyl-5,7-diazaspiro[3.4]octan-2-yl)(methyl)carbamate (INT-7) (250 mg, 0.724 mmol) in dry THF (2.5 mL) was dropwise added 2.4 M LiAlH$_4$ in THF (1.206 mL, 2.90 mmol). The mixture was stirred under reflux for 2 d. After cooling to RT, the mixture was diluted with THF (5 mL) and carefully quenched with Na$_2$SO$_4$.10H$_2$O. The mixture was diluted further with THF (15 mL) and stirred at RT for ca. 1 h. The mixture was filtered over a layer of Na$_2$SO$_4$ and rinsed with THF (10 mL) and DCM (25 mL). The combined filtrate was concentrated to dryness. The residue of the filtration was then stirred in MeOH/THF (1:1, v/v, 40 mL), filtered and the filtrate was combined with the first batch of crude product and concentrated to dryness. The product was triturated with hot DMSO. After filtration, the residue was washed with a small amount of Et$_2$O and dried under reduced pressure with a flow of N$_2$ to give cis-2-(dimethylamino)-2-phenyl-5,7-diazaspiro[3.4]octan-6-one (INT-14) (94.2 mg, 0.384 mmol, 53%). LCMS: calculated for [2M+Na]$^+$=513, found 513.3. $^1$H NMR (400 MHz, DMSO-d$_6$) δ 7.38 (m, 2H), 7.28 (m, 3H), 6.70 (s, 1H), 5.98 (s, 1H), 2.77-2.65 (m, 4H), 2.33 (d, J=11.4 Hz, 2H), 1.81 (s, 6H).

Tert-butyl cis-2-(2-(dimethylamino)-6-oxo-2-phenyl-5,7-diazaspiro[3.4]octan-7-yl)acetate (INT-15)

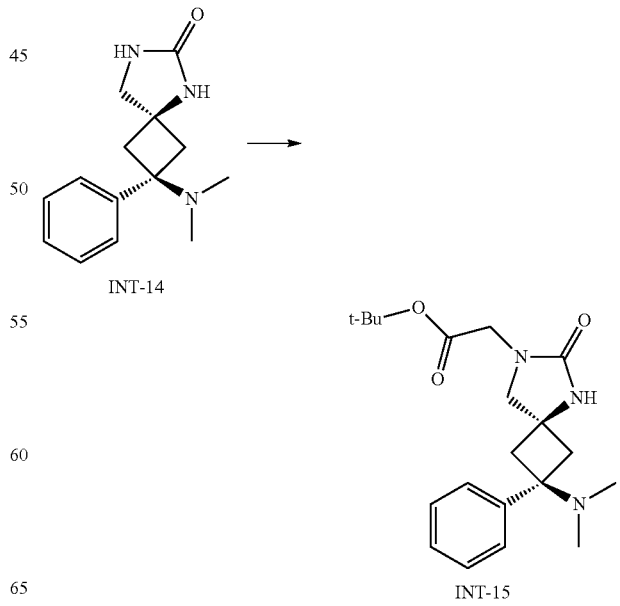

To a suspension of cis-2-(dimethylamino)-2-phenyl-5,7-diazaspiro[3.4]octan-6-one (INT-14) (260 mg, 1.06 mmol) in dry DMF (26 mL), a solution of 1.65 M solution of KOtBu in THF (0.642 mL, 1.06 mmol) was added dropwise under a N₂ atmosphere. After ~10 min a solution of tert-butyl bromoacetate (0.188 mL, 1.27 mmol) in DMF (5 mL) was added dropwise and the solution was stirred at RT for 30 min. Solid NH₄Cl (193 mg, 3.60 mmol) was added and after ~20 min the suspension was filtered. The residue was rinsed with MeCN (30 mL) and the combined filtrates were concentrated. The residue was loaded on silica using MeOH/DCM. Purification by flash chromatography (40 g silica, gradient DCM/(7 M NH₃ in MeOH), 99:1 to 9:1) afforded tert-butyl cis-2-(2-(dimethylamino)-6-oxo-2-phenyl-5,7-diazaspiro[3.4]octan-7-yl)acetate (INT-15) (142 mg, 0.40 mmol, 37%). LCMS: calculated for [M+H]⁺=360.5, found 360.3.

Cis-2-(2-(dimethylamino)-6-oxo-2-phenyl-5,7-diazaspiro[3.4]octan-7-yl)acetic Acid (INT-16)

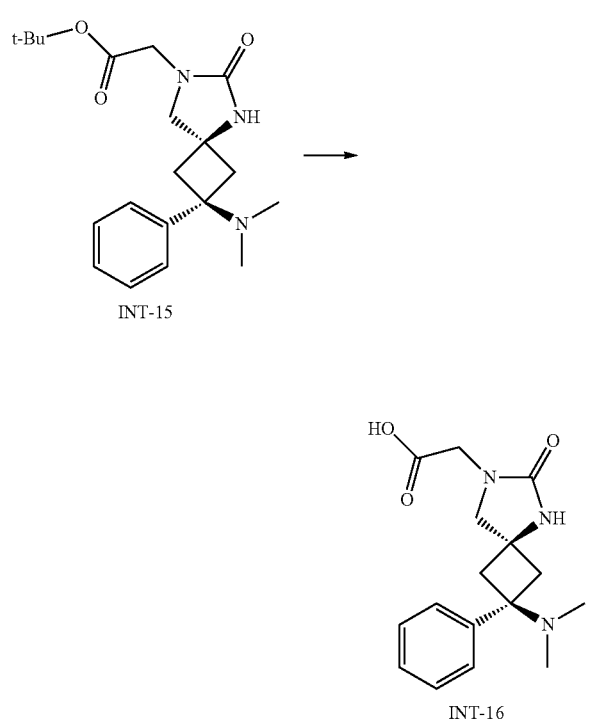

INT-15

INT-16

To a solution of tert-butyl cis-2-(2-(dimethylamino)-6-oxo-2-phenyl-5,7-diazaspiro[3.4]octan-7-yl)acetate (INT-15) (141 mg, 0.392 mmol) in DCM (3 mL) was added TFA (3.02 mL, 39.2 mmol) and the mixture was stirred at RT. After 2 h the mixture was concentrated and the crude product was concentrated again from DCM solution (2×, 10 mL each) to yield crude cis-2-(2-(dimethylamino)-6-oxo-2-phenyl-5,7-diazaspiro[3.4]octan-7-yl)acetic acid (INT-16) (240 mg) which was used in the next step without further purification. LCMS: calculated for [M+H]+=304.2, found 304.2.

Tert-butyl cis-2-(5-(cyclobutylmethyl)-2-(dimethylamino)-6-oxo-2-phenyl-5,7-diazaspiro-[3.4]octan-7-yl)acetate (INT-25)

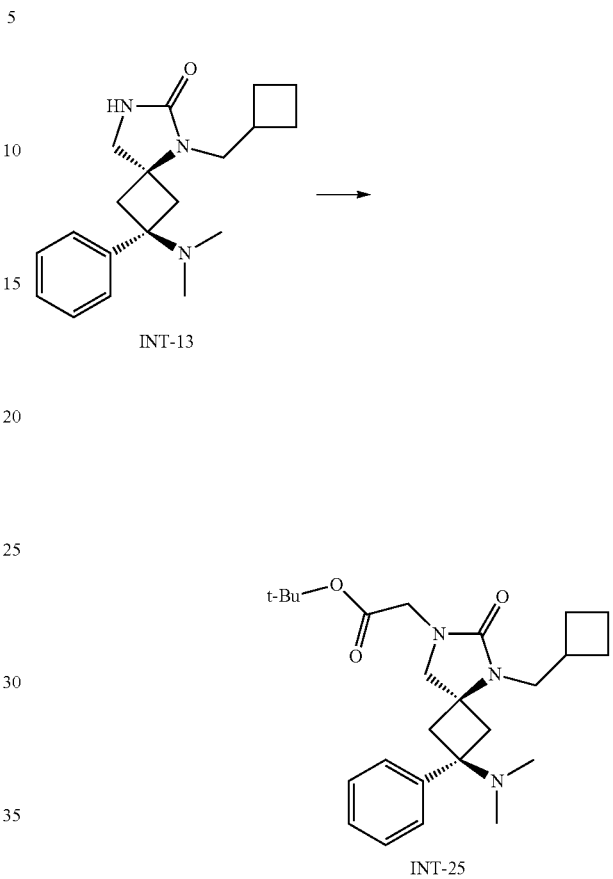

INT-13

INT-25

Oven dried glassware and an inert atmosphere Ar(g) were used. To a solution of cis-5-(cyclobutylmethyl)-2-(dimethylamino)-2-phenyl-5,7-diazaspiro[3.4]-octan-6-one (INT-13) (20 mg, 0.064 mmol) in a mixture of dry DMF (1 mL)/dry THF (1 mL) at RT was added 60% NaH in mineral oil (3.32 mg, 0.083 mmol). After 15 min gas evolution had ceased and a solution of tert-butyl bromoacetate (0.014 mL, 0.096 mmol) in dry DMF (1 mL) was added dropwise and the mixture was stirred at RT for 4 h. The reaction was quenched carefully by adding a mixture of brine/water (10 mL, 1/1, v/v). Then, the mixture was diluted with EtOAc (4 mL). The layers were separated and the water layer was extracted with EtOAc (3×4 mL). Combined organic layers were concentrated in vacuo (bath temperature 40° C.) to afford the crude product as a colorless sticky oil. This experiment was repeated in the same way on larger scale: cis-5-(cyclobutylmethyl)-2-(dimethylamino)-2-phenyl-5,7-diazaspiro[3.4]-octan-6-one (INT-13) (100 mg, 0.319 mmol). The crude products were combined and subjected to flash chromatography (12 g silica, gradient DCM/MeOH, 199:1-193:7) to afford tert-butyl cis-2-(5-(cyclobutylmethyl)-2-(dimethylamino)-6-oxo-2-phenyl-5,7-diazaspiro-[3.4]octan-7-yl)acetate (INT-25) as a white solid (135 mg (94% pure), 0.297 mmol, 78%). LCMS: calculated for [M+H]=428.6, found 428.3.

General Scheme for the Synthesis of INT-34

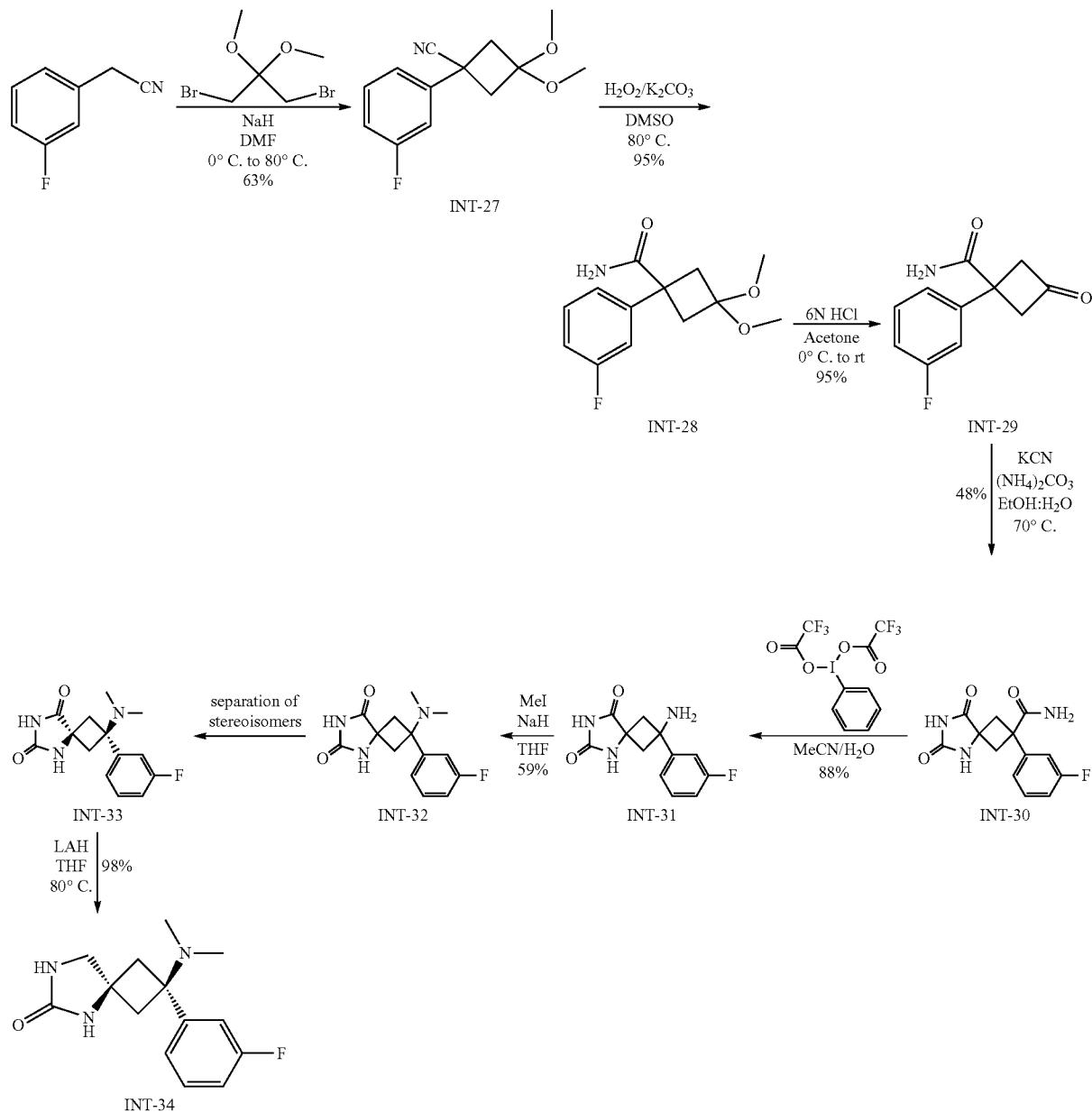

1-(3-fluorophenyl)-3,3-dimethoxycyclobutanecarbonitrile (INT-27)

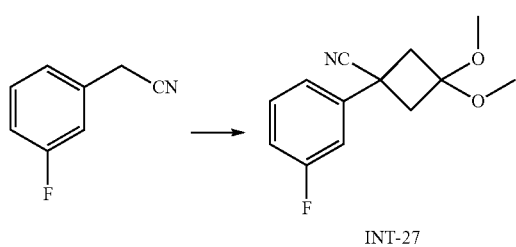

A suspension of NaH (110 g, 4580.1 mmol) in DMF (1.6 Lit) was cooled to 0° C., prior to the dropwise addition of 2-(3-fluorophenyl)acetonitrile (206 g, 1526.7 mmol) over 2 h. Reaction mixture was brought to rt and stirred for 45 min. To this mixture was added 1,3-dibromo-2,2-dimethoxypropane (200 g, 763.3 mmol) in one portion at RT and stirring was continued at RT for 16 h, before heating at 80° C. for 3 h. The reaction mixture was cooled to 0° C. and quenched with crushed ice water (500 mL) and diluted with water (2.5 L), extracted with ethyl acetate (2×2 L). The combined organic layer was washed with brine solution (3×3 L), dried over $Na_2SO_4$, filtered and the filtrate was concentrated. The crude compound was purified by silica gel column chromatography (100-200 mesh), eluting with 2-3% ethyl acetate in pet-ether to afford 114 g (63%) of 1-(3-fluorophenyl)-3,3-dimethoxycyclobutanecarbonitrile (INT-27) as a colorless liquid (TLC system: 15% ethyl acetate in pet ether; Rf: 0.4).

1-(3-fluorophenyl)-3,3-dimethoxycyclobutanecarboxamide (INT-28)

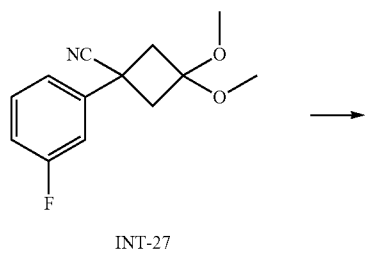

INT-27

30% H$_2$O$_2$ solution (109.9 mL, 970.2 mmol) was added drop wise to a mixture of K$_2$CO$_3$ (20 g, 145.5 mmol) and 1-(3-fluorophenyl)-3,3-dimethoxycyclobutanecarbonitrile (INT-27) (114 g, 485.1 mmol) in DMSO (1.14 L) at 40° C. and the reaction mixture was heated at 80° C. for 3 h. The reaction completion was monitored by TLC. The reaction mass was quenched with ice cold water (1 L) and), extracted with ethyl acetate (3×2 L), washed with brine solution (3×3 L), dried over Na$_2$SO$_4$, filtered and the filtrate was concentrated to afford 117 g of 1-(3-fluorophenyl)-3,3-dimethoxycyclobutanecarboxamide (INT-28) (95%) as an off white solid. (TLC system: 70% ethyl acetate in pet ether; Rf: 0.6). LCMS: calculated for [M+H]+=254.12, found 254.1.

1-(3-fluorophenyl)-3-oxocyclobutanecarboxamide (INT-29)

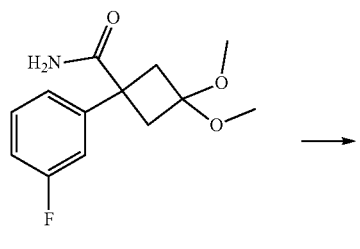

INT-28

To a solution of 1-(3-fluorophenyl)-3,3-dimethoxycyclobutanecarboxamide (INT-28) (1.8 g, 7.11 mmol) in acetone (18 mL) was added 6 N HCl (14 mL) at 0° C. and the resulting mixture was stirred at RT for 2 h. The reaction completion was monitored by TLC. The reaction mixture was neutralized with 20% NaOH solution up to pH 6 at 0-10° C., and extracted with ethyl acetate, dried over Na$_2$SO$_4$, filtered and the filtrate was concentrated to afford 1.4 g of 1-(3-fluorophenyl)-3-oxocyclobutanecarboxamide (INT-29) (95%) as a pink solid. (TLC system: 70% ethyl acetate in pet ether; Rf: 0.7). LCMS: calculated for [M+H]+=208.08, found 207.9.

2-(3-fluorophenyl)-6,8-dioxo-5,7-diazaspiro[3.4]octane-2-carboxamide (INT-30)

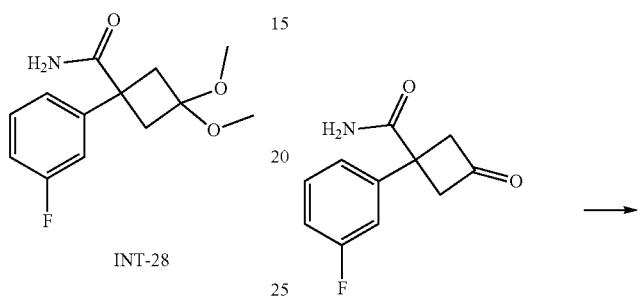

To a suspension of 1-(3-fluorophenyl)-3-oxocyclobutanecarboxamide (INT-29) (81 g, 391.30 mmol) in 1620 mL of EtOH:H$_2$O (1:1 v/v) were added KCN (35.6 g, 1533.9 mmol) and (NH$_4$)$_2$CO$_3$ (172 g, 1095.6 mmol) at room temperature. The reaction mixture was heated at 70° C. for 16 h. The reaction mixture was cooled to RT, diluted with water (810 mL), neutralized with 6 N HCl up to pH 6 and solid thus precipitated was filtered and dried to afford 52 g (47.9%) of 2-(3-fluorophenyl)-6,8-dioxo-5,7-diazaspiro[3.4]octane-2-carboxamide (INT-30) as an off-white solid (3:1 mixture of stereoisomers) (TLC: 10% methanol in dichloromethane; Rf: 0.25-0.40). LCMS: calculated for [M+H]+=278.1, found 277.9.

2-amino-2-(3-fluorophenyl)-5,7-diazaspiro[3.4]octane-6,8-dione (INT-31)

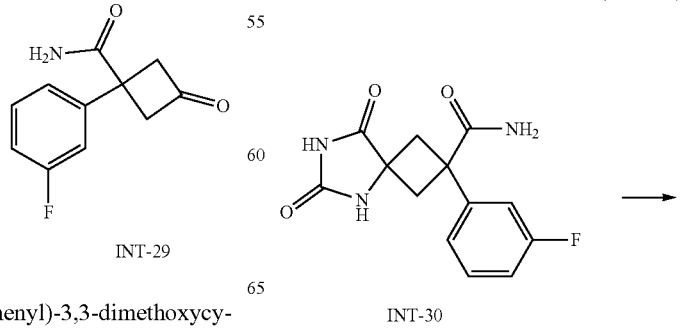

INT-30

Cis-2-(dimethylamino)-2-(3-fluorophenyl)-5,7-diazaspiro[3.4]octane-6,8-dione (INT-33)

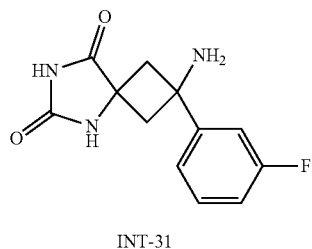

INT-31

Bis(trifluoroacetoxy)iodo]benzene (93 g, 217.39 mmol) was added to a solution of 2-(3-fluorophenyl)-6,8-dioxo-5,7-diazaspiro[3.4]octane-2-carboxamide (INT-30) (50 g, 181.15 mmol) in a mixture of acetonitrile and water (3:1, 2.0 L) at RT. The reaction mixture was stirred at RT for 16 h. The reaction completion was monitored by TLC. Reaction mixture was neutralized with aq NaHCO$_3$ solution till pH 6, extracted with ethyl acetate, dried over Na$_2$SO$_4$, filtered and the filtrate was concentrated to afford 40 g of 2-amino-2-(3-fluorophenyl)-5,7-diazaspiro[3.4]octane-6,8-dione (INT-31) (88%) as an off-white solid (~1:1 mixture of stereoisomers). (TLC:10% methanol in dichloromethane; Rf: 0.30-035). LCMS: calculated for [M+H]+=250.1, found 250.0.

2-(dimethylamino)-2-(3-fluorophenyl)-5,7-diazaspiro[3.4]octane-6,8-dione (INT-32)

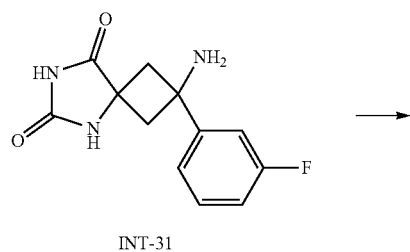

INT-31

To a solution of 2-amino-2-(3-fluorophenyl)-5,7-diazaspiro[3.4]octane-6,8-dione (INT-31)(18 g, 72.28 mmol) in THF (540 L) under argon were added DIPEA (25 mL, 144.57 mmol), MeI (18 mL, 289.15 mmol) and the reaction mixture was stirred at RT for 16 h. The reaction completion was monitored by LC-MS. The reaction mixture was concentrated under vacuum and triturated with water (200 mL) and the resulting solid was filtered to afford 12 g (59%) of 2-(dimethylamino)-2-(3-fluorophenyl)-5,7-diazaspiro[3.4]octane-6,8-dione (INT-32) as an off-white solid (~3:5 mixture of stereoisomers). LCMS: calculated for [M+H]+= 278.13, found 278.0.

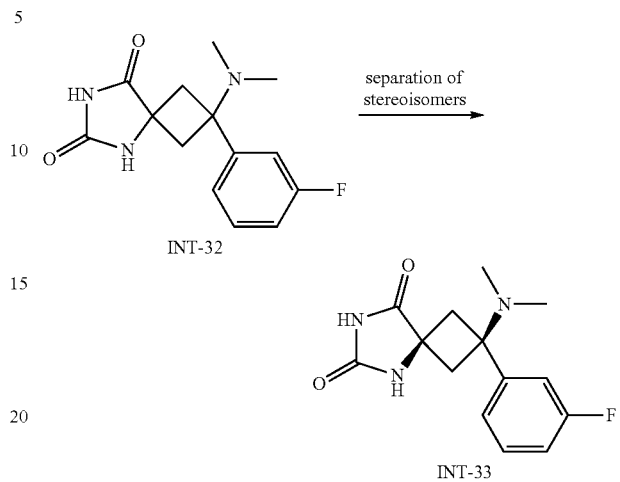

2-(Dimethylamino)-2-(3-fluorophenyl)-5,7-diazaspiro[3.4]octane-6,8-dione (INT-32) (12 µg) was purified by chiral SFC to get 6.2 g of cis-2-(dimethylamino)-2-(3-fluorophenyl)-5,7-diazaspiro[3.4]octane-6,8-dione (INT-33) as an off-white solid (LC-MS peak-2). Preparative SFC Conditions: column: Chiralpak IG (30×250 mm), 5p; % co-solvent: 30.0% (100% Methanol); % CO$_2$: 70.0%; total flow: 90.0 g/min; back pressure: 90.0 bar; UV: 214 nm; stack time: 10.3 min; load/inj: 103.0 mg; injection solvent: methanol+acetonitrile+THF (2:2:1); No. of injections: 140; instrument details:Make/Model: SFC-200-002. $^1$H NMR (400 MHz, DMSO-d$_6$) δ 10.50 (s, 1H), 8.32 (s, 1H), 7.42-7.33 (m, 1H), 7.12-7.08 (m, 1H), 6.97-6.89 (m, 2H), 2.86 (d, 2H), 2.51 (d, 2H), 1.88 (s, 6H).

Cis-2-(dimethylamino)-2-(3-fluorophenyl)-5,7-diazaspiro[3.4]octan-6-one (INT-34)

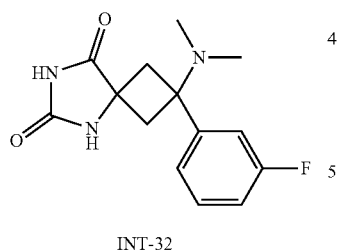

INT-32

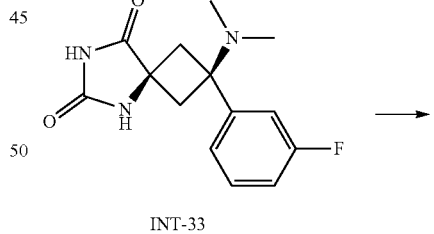

INT-33

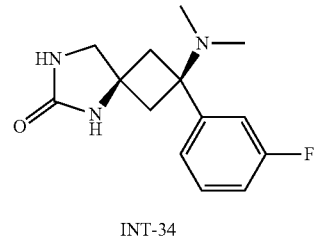

INT-34

LiAlH$_4$ (1 M in THF) (82 mL, 82.31 mmol) was added to a solution of cis-2-(dimethylamino)-2-(3-fluorophenyl)-5,7-diazaspiro[3.4]octane-6,8-dione (INT-33) (5.7 g, 20.57 mmol) in THF (228 mL) at 0° C. under argon. The reaction mixture was stirred at 80° C. for 16 h. The reaction completion was monitored by TLC. The reaction mixture was cooled to 0° C., quenched with saturated Na₂SO₄ solution and diluted with 10% methanol in DCM and filtered through celite bed. The filtrate was washed with 10% methanol in DCM and the filtrate was concentrated under reduced pressure to afford crude compound. The crude compound was triturated with methanol and diethyl ether successively to get 6 g (LC-MS 82%) of desired compound, which was in turn triturated with ethyl acetate to furnish 5.7 g (LC-MS 94%) of compound. Another trituration with methanol gave 5.4 g (98%, LC-MS 97%) of cis-2-(dimethylamino)-2-(3-fluorophenyl)-5,7-diazaspiro [3.4]octan-6-one (INT-34) as an off-white solid. (TLC system: 10% MeOH in DCM, Rf: 0.28). ¹H NMR (DMSO-d₆): δ 7.44-7.38 (m, 1H), 7.13-7.09 (m, 3H), 6.69 (s, 1H), 5.99 (s, 1H), 2.72-2.69 (m, 4H), 2.32 (dd, J=2.4 Hz, 9.6 Hz, 2H), 1.82 (s, 6H). LCMS: calculated for [M+H]+=264.15, found 264.15.

General Scheme for the Synthesis of INT-38 and INT-39

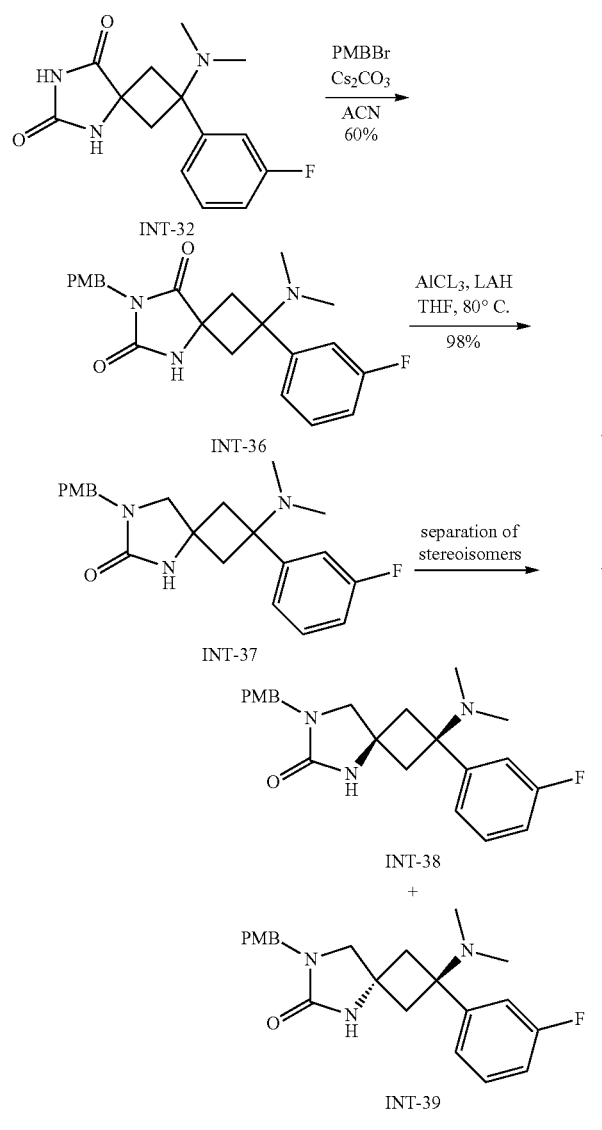

2-(Dimethylamino)-2-(3-fluorophenyl)-7-(4-methoxybenzyl)-5,7-diazaspiro[3.4]octane-6,8-dione (INT-36)

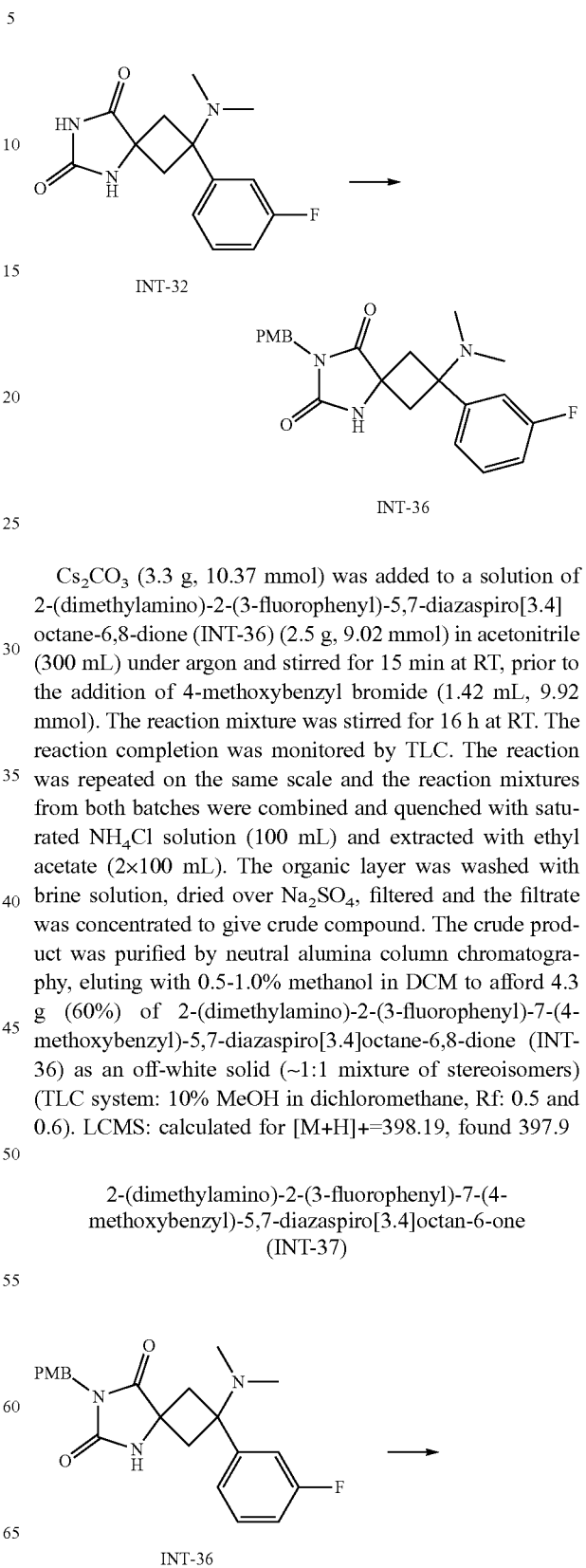

Cs₂CO₃ (3.3 g, 10.37 mmol) was added to a solution of 2-(dimethylamino)-2-(3-fluorophenyl)-5,7-diazaspiro[3.4] octane-6,8-dione (INT-36) (2.5 g, 9.02 mmol) in acetonitrile (300 mL) under argon and stirred for 15 min at RT, prior to the addition of 4-methoxybenzyl bromide (1.42 mL, 9.92 mmol). The reaction mixture was stirred for 16 h at RT. The reaction completion was monitored by TLC. The reaction was repeated on the same scale and the reaction mixtures from both batches were combined and quenched with saturated NH₄Cl solution (100 mL) and extracted with ethyl acetate (2×100 mL). The organic layer was washed with brine solution, dried over Na₂SO₄, filtered and the filtrate was concentrated to give crude compound. The crude product was purified by neutral alumina column chromatography, eluting with 0.5-1.0% methanol in DCM to afford 4.3 g (60%) of 2-(dimethylamino)-2-(3-fluorophenyl)-7-(4-methoxybenzyl)-5,7-diazaspiro[3.4]octane-6,8-dione (INT-36) as an off-white solid (~1:1 mixture of stereoisomers) (TLC system: 10% MeOH in dichloromethane, Rf: 0.5 and 0.6). LCMS: calculated for [M+H]+=398.19, found 397.9

2-(dimethylamino)-2-(3-fluorophenyl)-7-(4-methoxybenzyl)-5,7-diazaspiro[3.4]octan-6-one (INT-37)

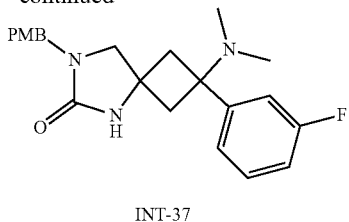

INT-37

AlCl₃ (5.6 g, 42.11 mmol) was dissolved in THF (300 mL) at 0° C. under argon, prior to the addition of LiAlH₄ (1 M in THF) (44 mL, 44.33 mmol) and the solution was stirred at RT for 1 h. To this mixture was dropwise added a solution 2-(dimethylamino)-2-(3-fluorophenyl)-7-(4-methoxybenzyl)-5,7-diazaspiro[3.4]octane-6,8-dione (INT-36) (4.4 g, 11.08 mmol) in THF (100 mL) at 0° C. under argon over 1 h. After addition, the reaction mixture was stirred at 80° C. for 16 h. The reaction completion was monitored by LC-MS. The reaction mixture was cooled to 0° C., quenched with sat. aq. NaHCO₃ and diluted with 10% methanol in DCM and filtered through celite bed. The filtrate was washed with 10% methanol in dichloromethane and the filtrate was concentrated under reduced pressure to afford crude compound. The crude compound was triturated with n-pentane to furnish 4.2 g (98%) of (2-(dimethylamino)-2-(3-fluorophenyl)-7-(4-methoxybenzyl)-5,7-diazaspiro[3.4]octan-6-one (INT-37) as an off-white solid (~1:1 mixture of stereoisomers). LCMS: calculated for [M+H]+=384.21, found 384.2.

Cis-2-(dimethylamino)-2-(3-fluorophenyl)-7-(4-methoxybenzyl)-5,7-diazaspiro[3.4]octan-6-one (INT-38) and trans-2-(dimethylamino)-2-(3-fluorophenyl)-7-(4-methoxybenzyl)-5,7-diazaspiro[3.4]octan-6-one (INT-39)

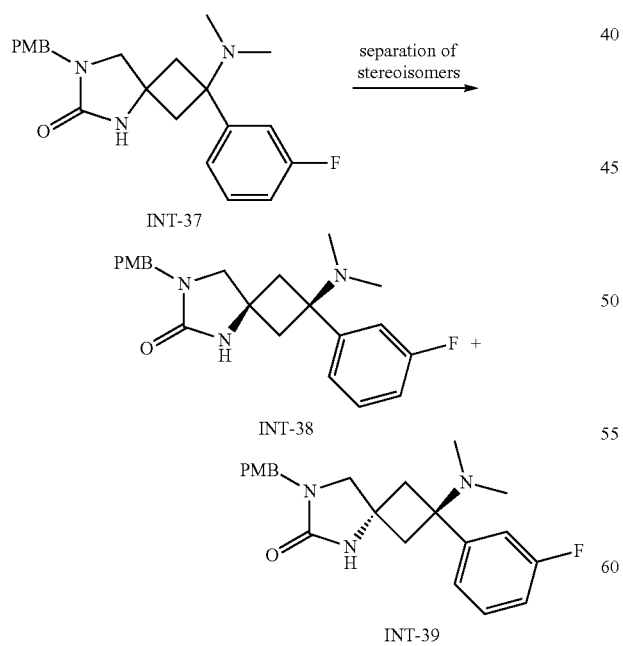

The diastereomeric mixture of (2-(dimethylamino)-2-(3-fluorophenyl)-7-(4-methoxybenzyl)-5,7-diazaspiro[3.4]octan-6-one (INT-37) (7.9 g) was separated by chiral SFC to afford 2.2 g of cis-2-(dimethylamino)-2-(3-fluorophenyl)-7-(4-methoxybenzyl)-5,7-diazaspiro[3.4]octan-6-one (INT-38) as an off-white solid (HPLC peak-1) and 2.4 g of trans-2-(dimethylamino)-2-(3-fluorophenyl)-7-(4-methoxybenzyl)-5,7-diazaspiro[3.4]octan-6-one (INT-39) as an off-white solid (HPLC peak-2). Preparative SFC Conditions: column: Chiralpak AD-H (30×250 mm), 5 t; % co-solvent: 30.0% (100% Methanol); % CO₂: 70.0%; total flow: 90.0 g/min; back pressure: 90.0 bar; UV: 214 nm; stack time: 6.3 min; load/inj: 74.0 mg; injection solvent: 200 mL methanol; No. of injections: 70; instrument details: Make/Model: SFC-200-003.

Cis-2-(dimethylamino)-2-(3-fluorophenyl)-7-(4-methoxybenzyl)-5,7-diazaspiro[3.4]octan-6-one (INT-38): ¹H NMR (DMSO-d₆): δ 7.38 (br s, 1H), 7.07 (br s, 2H), 7.01-6.97 (m, 3H), 6.83 (d, J=6.8 Hz, 2H), 4.04 (s, 2H), 3.70 (s, 3H), 2.66 (br s, 4H), 2.36 (br s, 2H), 1.82 (br s, 6H).

Trans-2-(dimethylamino)-2-(3-fluorophenyl)-7-(4-methoxybenzyl)-5,7-diazaspiro[3.4]octan-6-one (INT-39): ¹H NMR (DMSO-d₆): δ 7.37-7.34 (m, 1H), 7.16 (d, J=6.8 Hz, 2H), 7.08-7.05 (m, 1H), 6.91 (d, J=6.8 Hz, 2H), 6.83 (d, J=6.4 Hz, 2H), 6.77 (s, 1H), 4.16 (s, 2H), 3.74 (s, 3H), 3.34 (s, 2H), 2.56 (d, J=1.0 Hz, 2H), 2.26 (d, J=10.0 Hz, 2H), 1.88 (s, 6H).

General Scheme for the Synthesis of INT-43

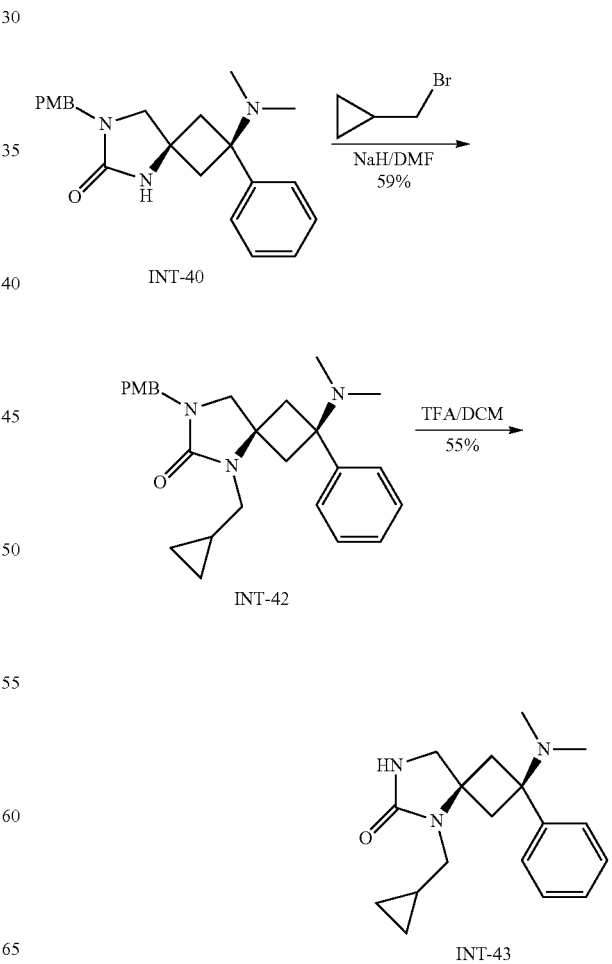

Cis-5-(cyclopropylmethyl)-2-(dimethylamino)-7-(4-methoxybenzyl)-2-phenyl-5,7-diazaspiro [3.4]octan-6-one (INT-42)

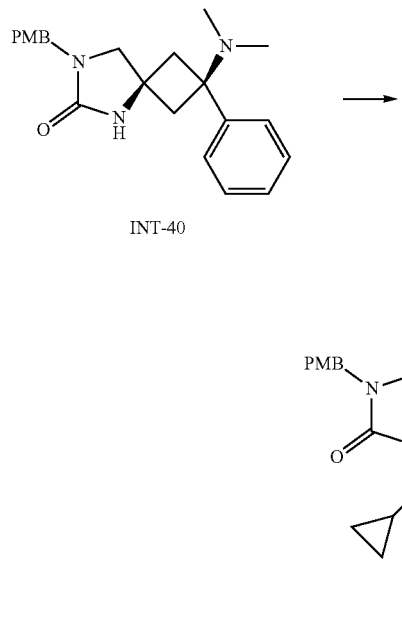

INT-40

INT-42

To a solution of cis-2-dimethylamino-7-(4-methoxy-benzyl)-2-phenyl-5,7-diaza-spiro[3.4]octan-6-one (INT-40) (3.0 g, 8.22 mmol, 1.0 eq.) in dry DMF (160 ml) was added 60% NaH (657 mg, 16.438 mmol, 2 eq.) at 0° C. and the resulting mixture was stirred for 30 min followed by addition of bromomethyl-cyclopropane (1.9 ml, 20.54 mmol, 2.5 eq.) at 0° C. The reaction mixture was stirred at RT for 16 h. The reaction mixture was quenched with ice-cold water (20 ml) and extracted with ethyl acetate (1 L). The organic layer was washed with ice-cold water (3×100 ml), brine (250 ml) and dried over sodium sulfate. Organic layer was concentrated under reduced pressure to get crude product which was purified by column chromatography (silica gel; 1.5% MeOH/DCM) to yield cis-5-cyclopropylmethyl-2-dimethylamino-7-(4-methoxy-benzyl)-2-phenyl-5,7-diaza-spiro[3.4]octan-6-one (INT-42) as colourless sticky liquid. LCMS: calculated for [M+H]+=420.4, found 420.1.

Cis-5-cyclopropylmethyl-2-dimethylamino-2-phenyl-5,7-diaza-spiro[3.4]octan-6-one (INT-43)

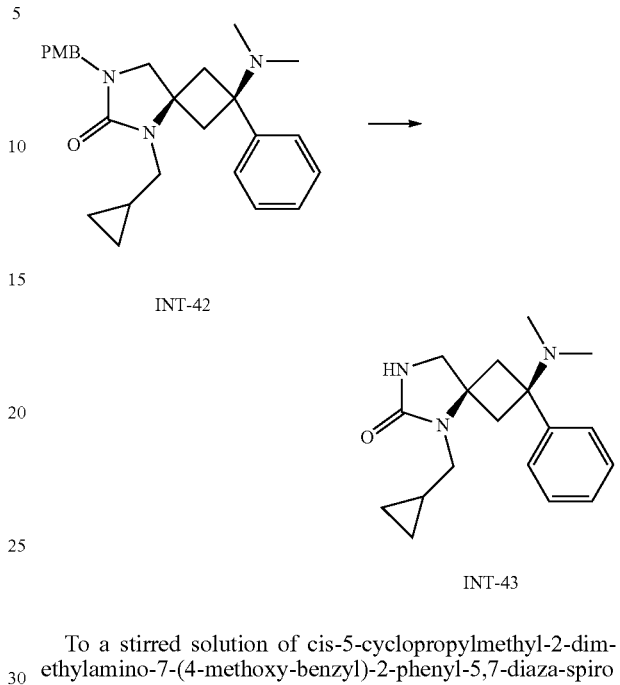

INT-42

INT-43

To a stirred solution of cis-5-cyclopropylmethyl-2-dimethylamino-7-(4-methoxy-benzyl)-2-phenyl-5,7-diaza-spiro [3.4]octan-6-one (INT-42) (2.0 g) in DCM (12 ml) was added TFA (12 ml) drop-wise at 0° C. The reaction mixture was stirred at RT for 16 h and then concentrated under reduced pressure to get crude product which was purified by column chromatography (silica gel neutralized by aqueous NH$_3$; 4% MeOH/DCM) to yield cis-5-cyclopropylmethyl-2-dimethylamino-2-phenyl-5,7-diaza-spiro[3.4]octan-6-one (INT-43) as a white solid. Note: This step was done with another 1.0 g and 2.0 g batches. Combined yield: 60% (2.15 g, 7.18 mmol). LCMS: calculated for [M+H]+=300.3, found 300.2.

For further intermediates the synthesis in analogy to previously described methods is given in the following table. The syntheses of the building blocks and intermediates have either been described previously within this application or can be performed in analogy to the herein described methods or by methods known to the person, skilled in the art. Such a person will also know which building blocks and intermediates need to be chosen for synthesis of each exemplary compound.

| Intermediate | Chemical Name | Chemical Structure | in analogy to method | m/z [M + H]+ |
|---|---|---|---|---|
| INT-17 | tert-butyl trans-(7-(4-methoxybenzyl)-6,8-dioxo-2-phenyl-5,7-diazaspiro[3.4]octan-2-yl)(methyl)carbamate | (structure shown) | INT-9 | 466.2 |

-continued

| Intermediate | Chemical Name | Chemical Structure | in analogy to method | m/z [M + H]+ |
|---|---|---|---|---|
| INT-18 | tert-butyl trans-(5-(cyclobutylmethyl)-7-(4-methoxybenzyl)-6,8-dioxo-2-phenyl-5,7-diazaspiro[3.4]octan-2-yl)(methyl)carbamate | 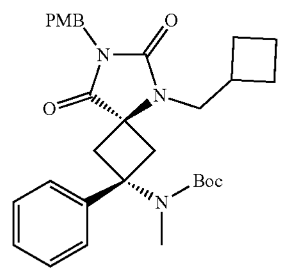 | INT-10 | 534.3 |
| INT-19 | trans-5-(cyclobutylmethyl)-2-(methylamino)-2-phenyl-5,7-diazaspiro[3.4]octane-6,8-dione | 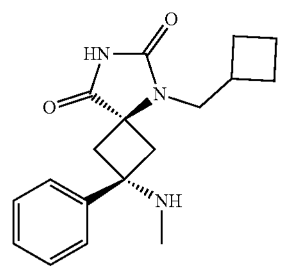 [SMILES: CN[C@]1(c2ccccc2)C[C@@]2(C1)C(=O)NC(=O)N2CC1CCC1] | INT-11 | 314.2 |
| INT-20 | trans-5-(cyclobutylmethyl)-2-(dimethylamino)-2-phenyl-5,7-diazaspiro[3.4]octane-6,8-dione | 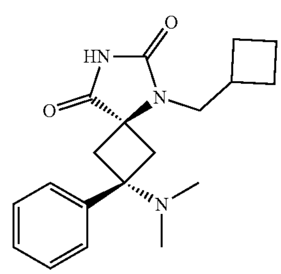 [SMILES: CN(C)[C@]1(c2ccccc2)C[C@@]2(C1)C(=O)NC(=O)N2CC1CCC1] | INT-12 | 328.2 |
| INT-21 | trans-5-(cyclobutylmethyl)-2-(dimethylamino)-2-phenyl-5,7-diazaspiro[3.4]octan-6-one | 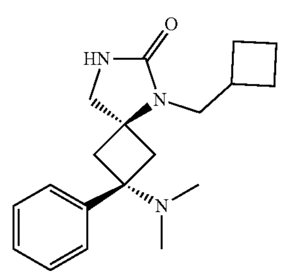 [SMILES: CN(C)[C@]1(c2ccccc2)C[C@]2(CNC(=O)N2CC2CCC2)C1] | INT-13 | 314.2 |
| INT-22 | trans-2-(dimethylamino)-2-phenyl-5,7-diazaspiro[3.4]octan-6-one | 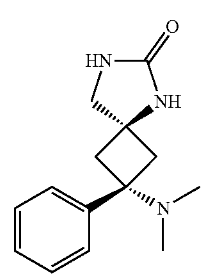 [SMILES: CN(C)[C@]1(c2ccccc2)C[C@]2(CNC(=O)N2)C1] | INT-14 | 246.2 |

-continued

| Intermediate | Chemical Name | Chemical Structure | in analogy to method | m/z [M + H]+ |
|---|---|---|---|---|
| INT-23 | trans-2-(2-(dimethylamino)-6-oxo-2-phenyl-5,7-diazaspiro[3.4]octan-7-yl)acetic acid tert-butyl ester | 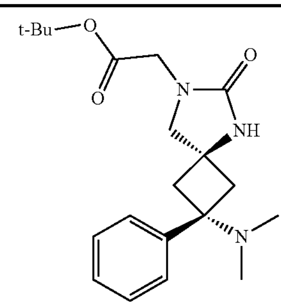 | INT-15 | 360.2 |
| INT-24 | trans-2-(2-(dimethylamino)-6-oxo-2-phenyl-5,7-diazaspiro[3.4]octan-7-yl)acetic acid | 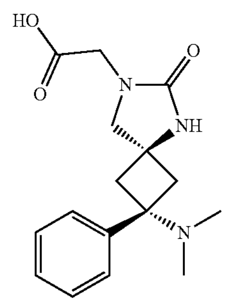 [SMILES: CN(C)[C@]1(c2ccccc2)C[C@]2(CN(CC(=O)O)C(=O)N2)C1] | INT-16 | 304.2 |
| INT-26 | cis-2-(5-(cyclobutylmethyl)-2-(dimethylamino)-6-oxo-2-phenyl-5,7-diazaspiro[3.4]octan-7-yl)acetic acid | 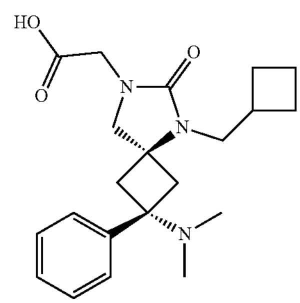 [SMILES: CN(C)[C@]1(c2ccccc2)C[C@]2(CN(CC(=O)O)C(=O)N2CC2CCC2)C1] | INT-16 | 372.2 |
| INT-35 | trans-2-(dimethylamino)-2-(3-fluorophenyl)-5,7-diazaspiro[3.4]octan-6-one | 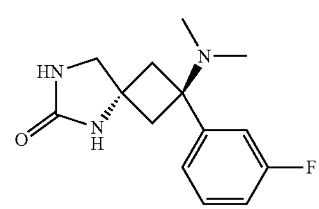 [SMILES: CN(C)[C@]1(c2cccc(F)c2)C[C@]2(CNC(=O)N2)C1] | INT-34 | 264.15 |
| INT-40 | Cis-2-(dimethylamino)-7-(4-methoxybenzyl)-2-phenyl-5,7-diazaspiro[3.4]octan-6-one | 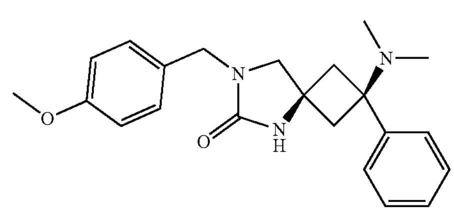 [SMILES: COc1ccc(CN2C[C@]3(C[C@](c4ccccc4)(N(C)C)C3)NC2=O)cc1] | INT-38 | 366.2 |
| INT-41 | Trans-2-(dimethylamino)-7-(4-methoxybenzyl)-2-phenyl-5,7-diazaspiro[3.4]octan-6-one | 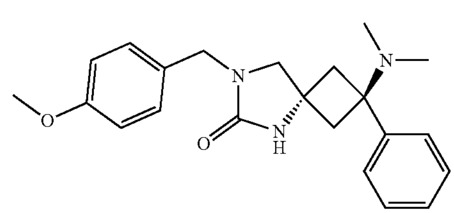 [SMILES: COc1ccc(CN2C[C@]3(C[C@@](c4ccccc4)(N(C)C)C3)NC2=O)cc1] | INT-39 | 366.2 |

| Intermediate | Chemical Name | Chemical Structure | in analogy to method | m/z [M + H]+ |
|---|---|---|---|---|
| INT-44 | Cis-5-(cyclopropylmethyl)-2-(dimethylamino)-2-(3-fluorophenyl)-7-(4-methoxybenzyl)-5,7-diazaspiro[3.4]octan-6-one | 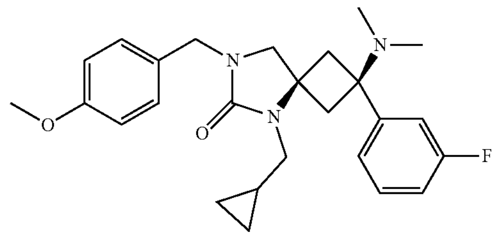 [SMILES: COc1ccc(CN2C[C@]3(C[C@](c4cccc(F)c4)(N(C)C)C3)N(CC3CC3)C2=O)cc1] | INT-42 | 438.3 |
| INT-45 | Cis--5-(cyclopropylmethyl)-2-(dimethylamino)-2-(3-fluorophenyl)-5,7-diazaspiro[3.4]octan-6-one | 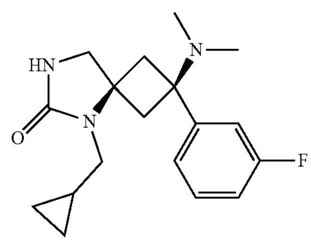 [SMILES: CN(C)[C@]1(c2cccc(F)c2)C[C@@]2(CNC(=O)N2CC2CC2)C1] | INT-43 | 318.2 |

Synthesis of Exemplary Compounds

Cis-2-(2-(dimethylamino)-6-oxo-2-phenyl-5,7-diazaspiro[3.4]octan-7-yl)acetamide (SC-1)

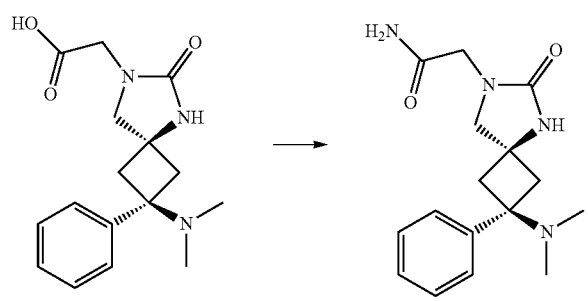

To a solution of crude cis-2-(2-(dimethylamino)-6-oxo-2-phenyl-5,7-diazaspiro[3.4]octan-7-yl)acetic acid (INT-16) (120 mg, max. 0.196 mmol) in DCM (3.5 mL) were added Et₃N (0.137 mL, 0.98 mmol) and NH₄Cl (41.9 mg, 0.784 mmol) under a N₂ atmosphere. HATU (112 mg, 0.294 mmol) was added and the mixture was stirred at RT overnight. The mixture was diluted with MeOH (5 mL) and filtered off. The residue was rinsed with MeOH (10 mL) and the combined filtrates were concentrated. The residue was purified by basic preparative LC (HPLC instrument type: Agilent Technologies 1200 preparative LC; column: Waters XSelect CSH (C18, 150×25 mm, 10t); flow: 43 mL/min; column temp: RT; eluent A: 99% acetonitrile+1% 10 mM ammonium bicarbonate in water pH=9.0, eluent B: 10 mM ammonium bicarbonate in water pH=9.0; lin. gradient: t=0 min 5% A, t=2.5 min 5% A, t=11 min 50% A, t=13 min 100% A, t=17 min 100% A; detection: DAD (210 nm)). The product-containing fractions were concentrated to dryness and co-evaporated with MeCN (2×, 5 mL each) and Et₂O (2×, 5 mL each) to yield cis-2-(2-(dimethylamino)-6-oxo-2-phenyl-5,7-diazaspiro[3.4]octan-7-yl)acetamide (SC-1) (42 mg, 0.139 mmol). LCMS: calculated for [M+H]⁺=303.2, found 303.2. ¹H NMR (400 MHz, DMSO-d₆) δ 7.43-7.34 (m, 2H), 7.33-7.17 (m, 4H), 6.98 (s, 1H), 6.89 (s, 1H), 3.45 (s, 2H), 2.85 (s, 2H), 2.75 (d, J=11.9 Hz, 2H), 2.36 (d, J=11.9 Hz, 2H), 1.81 (s, 6H).

Cis-2-(dimethylamino)-7-(2-(1,1-dioxidothiomorpholino)-2-oxoethyl)-2-phenyl-5,7-diazaspiro [3.4]octan-6-one (SC-2)

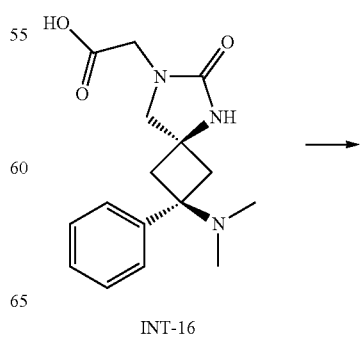

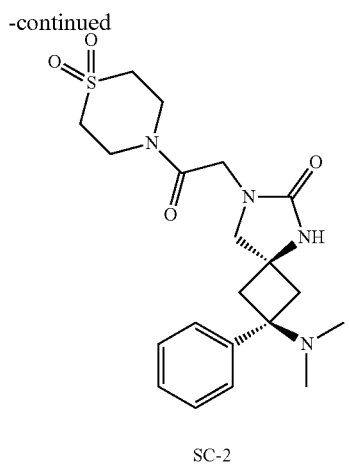

SC-2

To a solution of cis-2-(2-(dimethylamino)-6-oxo-2-phenyl-5,7-diazaspiro[3.4]octan-7-yl)acetic acid (INT-16) (120 mg, max. 0.196 mmol) in DCM (3.5 mL) were added Et₃N (0.109 mL, 0.784 mmol) and thiomorpholine 1,1-dioxide (106 mg, 0.784 mmol) under a N₂ atmosphere. HATU (112 mg, 0.294 mmol) was added and the mixture was stirred at RT overnight. The mixture was diluted with MeOH (5 mL) and filtered off. The residue was rinsed with MeOH (10 mL) and the combined filtrates were concentrated. The residue was purified by basic preparative LC (HPLC instrument type: Agilent Technologies 1200 preparative LC; column: Waters XSelect CSH (C18, 150×25 mm, 10t); flow: 43 mL/min; column temp: RT; eluent A: 99% acetonitrile+1% 10 mM ammonium bicarbonate in water pH=9.0, eluent B: 10 mM ammonium bicarbonate in water pH=9.0; lin. gradient: t=0 min 5% A, t=2.5 min 5% A, t=11 min 50% A, t=13 min 100% A, t=17 min 100% A; detection: DAD (210 nm)). The product-containing fractions were concentrated to dryness and co-evaporated with MeCN (2×, 5 mL each) and Et₂O (2×, 5 mL each) to yield cis-2-(dimethylamino)-7-(2-(1,1-dioxidothiomorpholino)-2-oxoethyl)-2-phenyl-5,7-diazaspiro[3.4]octan-6-one (SC-2) (52 mg, 0.124 mmol). LCMS: calculated for [M+H]⁺=421.2, found 421.2. ¹H NMR (400 MHz, DMSO-d₆) δ 7.38 (t, J=7.5 Hz, 2H), 7.32-7.22 (m, 3H), 6.99 (s, 1H), 3.86 (s, 2H), 3.79-3.66 (m, 4H), 3.18 (s, 2H), 3.02 (s, 2H), 2.88 (s, 2H), 2.76 (d, J=11.9 Hz, 2H), 2.37 (d, J=11.9 Hz, 2H), 1.80 (s, 6H).

Cis-5-(2-(dimethylamino)-6-oxo-2-phenyl-5,7-diazaspiro[3.4]octan-7-yl)-4-methoxypyrimidine-2-carbonitrile (SC-3)

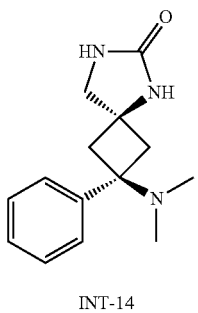

INT-14

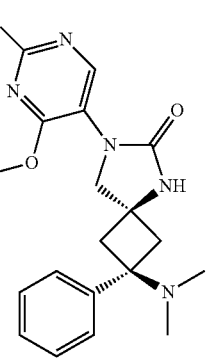

SC-3

This reaction was carried out under Ar. A mixture of cis-2-(dimethylamino)-2-phenyl-5,7-diazaspiro[3.4]octan-6-one (INT-14) (83 mg, 0.338 mmol), 5-bromo-4-methoxypyrimidine-2-carbonitrile (80 mg, 0.372 mmol), Cs₂CO₃ (331 mg, 1.015 mmol) and XantPhos (9.79 mg, 0.017 mmol) in dry 1,4-dioxane (8 mL) was flushed with Ar for 5 min. Pd₂(dba)₃ (31.0 mg, 0.034 mmol) was added and the reaction mixture was stirred at 110° C. overnight. The reaction mixture was combined with a reaction mixture obtained from another experiment which started from cis-2-(dimethylamino)-2-phenyl-5,7-diazaspiro[3.4]octan-6-one (INT-14) (41 mg, 0.167 mmol) using the described procedure. H₂O (10 mL) was added and the aqueous layer was extracted with DCM (3×10 mL) and DCM/7 M NH₃ in MeOH, 9:1 (3×10 mL). Organic layers were combined, dried (Na₂SO₄) and evaporated under reduced pressure. The product was subjected to flash chromatography (28 g silica, gradient DCM/(7 M NH₃ in MeOH), 1:0 to 95:5). TLC-impure fractions were combined and subjected to flash chromatography again (28 g silica, gradient DCM/(7 M NH₃ in MeOH), 97:3 to 95:5), to result in impure product which was triturated with MeOH (2×2 mL). This batch of product was combined with the TLC-pure batch of the first flash column. The resulting batch was triturated with MeOH (ca. 2 mL). The residue was dried in vacuo, to give cis-5-(2-(dimethylamino)-6-oxo-2-phenyl-5,7-diazaspiro[3.4]octan-7-yl)-4-methoxypyrimidine-2-carbonitrile (SC-3) (87 mg, 0.23 mmol, 46%). LCMS: calculated for [M+H]+=379.2, found 379.2. ¹H NMR (400 MHz, CDCl3) δ 8.88 (s, 1H), 7.37 (t, J=7.3 Hz, 2H), 7.30 (t, J=7.3 Hz, 1H), 7.09 (d, J=7.2 Hz, 2H), 6.01 (s, 1H), 4.00 (s, 3H), 3.76 (s, 2H), 2.71 (d, J=12.4 Hz, 2H), 2.63 (d, J=12.4 Hz, 2H), 2.05 (s, 6H).

Cis-5-(cyclobutylmethyl)-2-(dimethylamino)-7-(2-(1,1-dioxidothiomorpholino)-2-oxoethyl)-2-phenyl-5,7-diazaspiro[3.4]octan-6-one (SC-6)

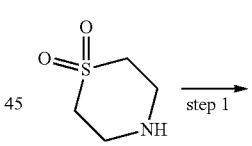

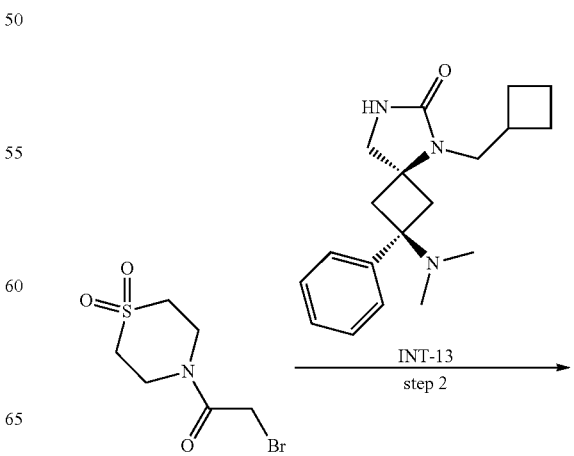

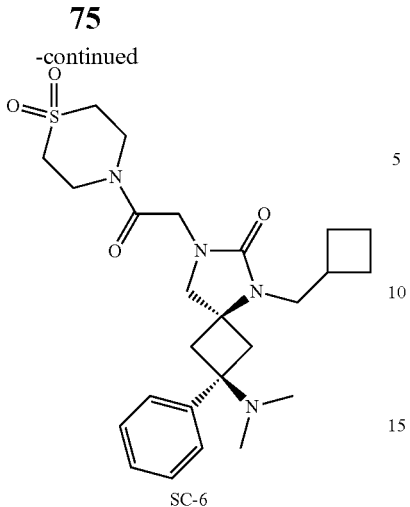

SC-6

Step 1: 2-bromo-1-(1,1-dioxidothiomorpholino)ethanone

A solution of thiomorpholine 1,1-dioxide (1.0 g, 7.40 mmol) in DCM (30 mL) was added dropwise over 20 min to a cooled (0° C.) and argon flushed mixture of 2-bromoacetyl bromide (970 µL, 11.10 mmol) and $K_3PO_4$ (3.93 g, 18.5 mmol) in DCM (20 mL) and the mixture was stirred at RT overnight. The reaction mixture was diluted with DCM (50 mL) and quenched with aq. 0.5 M HCl (10 mL). Water (50 mL) and brine (50 mL) were added and the layers were separated. The aqueous layer was extracted with DCM (50 mL) and the combined organic layers were washed with aq. 10% $KHCO_3$ (100 mL) and brine (50 mL), dried over $Na_2SO_4(s)$ and concentrated to dryness. The residue was triturated with $Et_2O$ (50 mL) for 30 min. The solid material was filtered off, washed with some $Et_2O$ and dried under reduced pressure to afford 2-bromo-1-(1,1-dioxidothiomorpholino)ethanone (1.20 g, 4.69 mmol, 63%). LCMS: calculated for $[M+H]^+$=256.1/258.1, found 256.0/258.0.

Step 2: cis-5-(cyclobutylmethyl)-2-(dimethylamino)-7-(2-(1,1-dioxidothiomorpholino)-2-oxoethyl)-2-phenyl-5,7-diazaspiro[3.4]octan-6-one (SC-6)

Oven dried glassware and an inert atmosphere (Ar(g)) were used. To a solution of cis-5-(cyclobutylmethyl)-2-(dimethylamino)-2-phenyl-5,7-diazaspiro[3.4]octan-6-one (INT-13) (40 mg, 0.128 mmol) in a mixture of dry DMF (2 mL) and dry THF (2 mL) was added 60% NaH in mineral oil (10.21 mg, 0.255 mmol) and the mixture was stirred at RT. After 15 min gas evolution had ceased and a solution of 2-bromo-1-(1,1-dioxidothiomorpholino)ethanone (49.0 mg, 0.191 mmol) in dry DMF (2 mL) was added dropwise. The mixture was stirred at RT for 1 h. A mixture of brine/water (10 mL, 1/1, v/v) was carefully added and the mixture was diluted with DCM (10 mL). The layers were separated using a phase separator. The water layer was extracted with DCM (4×5 mL). Organic layers were combined and concentrated n vacuo (bath temperature 55° C.). The residue was concentrated consequently from the solution in toluene, EtOAc and DCM to obtain a colourless sticky oil. The obtained crude product was purified by flash chromatography (4 g silica, gradient DCM/MeOH, 199:1 to 95:5) which afforded cis-5-(cyclobutylmethyl)-2-(dimethylamino)-7-(2-(1,1-dioxidothiomorpholino)-2-oxoethyl)-2-phenyl-5,7-diazaspiro [3.4]octan-6-one (SC-6) (47 mg, 0.096 mmol, 75%) as a white solid. LCMS: calculated for $[M+H]^+$=489.6, found 489.3. $^1H$ NMR (400 MHz, $CDCl_3$) 7.38 (t, J=7.4 Hz, 2H), 7.31 (d, J=7.2 Hz, 1H), 7.21 (d, J=7.2 Hz, 2H), 3.98 (broad d, 4H), 3.89 (s, 2H), 3.32 (d, J=7.3 Hz, 2H), 2.99 (broad s, 4H), 2.93 (s, 2H), 2.70-2.53 (m, 5H), 2.04 (m, 2H), 1.92 (s, 6H), 1.81 (m, 4H).

Trans-2-(5-(cyclobutylmethyl)-2-(dimethylamino)-6-oxo-2-phenyl-5,7-diazaspiro[3.4]octan-7-yl)acetamide (SC-9)

INT-21

SC-9

To an ice-bath cooled suspension of trans-5-(cyclobutylmethyl)-2-(dimethylamino)-2-phenyl-5,7-diazaspiro[3.4] octan-6-one (INT-21) (378 mg, 1.21 mmol) in dry DMF (10 mL) under an argon atmosphere was added dry THF (10 mL) to give a clear solution. 60% NaH in mineral oil (72.4 mg, 1.81 mmol) was added and the mixture was stirred at RT. After ~20 min a solution of 2-chloroacetamide (201 µL, 1.81 mmol) in dry THF (10 mL) was added dropwise and the mixture was stirred at RT overnight. More 60% NaH in mineral oil (193 mg, 4.82 mmol) was added and the mixture was stirred at RT for 1 h, then 2-chloroacetamide (201 µL, 1.81 mmol) was added. The mixture was stirred at RT for 3 h, quenched with water (50 mL) and extracted with EtOAc (2×75 mL). The combined organic layers were washed with brine (2×100 mL), dried over $Na_2SO_4(s)$ and concentrated to dryness. The crude material was purified by preparative LC (HPLC instrument type: Agilent Technologies 1200 preparative LC; column: Waters XSelect CSH (C18, 150×25 mm, 10); flow: 43 mL/min; column temp: RT; eluent A: 99% acetonitrile+1% 10 mM ammonium bicarbonate in water pH=9.0, eluent B: 10 mM ammonium bicarbonate in water pH=9.0; lin. gradient: t=0 min 20% A, t=2.5 min 20% A, t=11 min 60% A, t=13 min 100% A, t=17 min 100% A; detection: DAD (210 nm)). Product-containing fractions were pooled, concentrated to dryness. The resulting product was concentrated again from the solution in $Et_2O$ (2×5 mL)

to afford trans-2-(5-(cyclobutylmethyl)-2-(dimethylamino)-6-oxo-2-phenyl-5,7-diazaspiro[3.4]octan-7-yl)acetamide (SC-9) (89 mg, 0.241 mmol, 20%). LCMS: calculated for [M+H]+=371.50, found: 371.3. ¹H NMR (400 MHz, DMSO-d₆) δ 7.37 (t, J=7.5 Hz, 2H), 7.31 (s, 1H), 7.26 (t, J=7.2 Hz, 1H), 7.08 (d, J=7.6 Hz, 2H), 6.99 (s, 1H), 3.65 (s, 2H), 3.59 (s, 2H), 2.88 (d, J=7.2 Hz, 2H), 2.58-2.46 (m, 2H), 2.41 (d, J=12.8 Hz, 2H), 2.32 (dq, J=14.9, 7.4 Hz, 1H), 1.92 (s, 6H), 1.86-1.76 (m, 2H), 1.68 (tt, J=19.5, 10.3 Hz, 2H), 1.51 (p, J=8.4 Hz, 2H).

Cis-2-(Dimethylamino)-7-(4-methyl-2-morpholinopyrimidin-5-yl)-2-phenyl-5,7-diazaspiro [3.4]octan-6-one (SC-12)

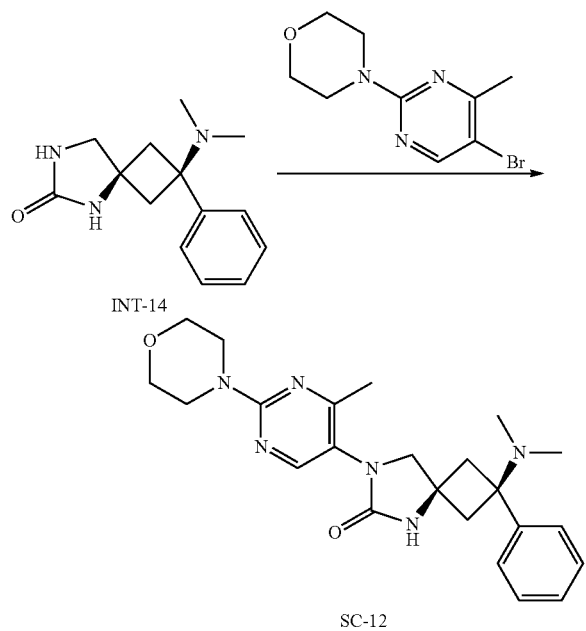

K₂CO₃ (338 mg, 2.448 mmol) was added to a solution of cis-2-(dimethylamino)-2-phenyl-5,7-diazaspiro[3.4]octan-6-one (INT-14) (200 mg, 0.816 mmol) and 4-(5-bromo-4-methylpyrimidin-2-yl)morpholine (314 mg, 1.224 mmol) in 1,4-dioxane (20 mL) at RT under argon atmosphere. To this reaction mixture, N,N-dimethylethylenediamine (71.8 mg, 0.816 mmol) followed by CuI (155 mg, 0.816 mmol) were added and degassed with argon for 15 minutes. The resulting reaction mixture was then maintained at 120° C. for 16 h. The reaction progress was checked by LC-MS.

Following the above condition, another 200 mg of (2s,4s)-2-(dimethylamino)-2-phenyl-5,7-diazaspiro [3.4]octan-6-one was treated with 4-(5-bromo-4-methylpyrimidin-2-yl) morpholine. Both these lots were mixed, quenched with water (30 mL) and extracted with ethyl acetate (2×30 mL). The combined organic layer was concentrated under reduced pressure. The crude product was purified by prep-HPLC to afford 37 mg (5%) of cis-2-(dimethylamino)-7-(4-methyl-2-morpholinopyrimidin-5-yl)-2-phenyl-5,7-diazaspiro[3.4] octan-6-one (SC-12) as an off-white solid (TLC system: 10% MeOH in dichloromethane; Rf: 0.5). ¹H NMR (400 MHz, DMSO-d₆): δ 8.04 (s, 1H), 7.38-7.26 (m, 6H), 3.65-3.60 (m, 8H), 3.10 (s, 2H), 2.86-2.82 (m, 2H), 2.46-2.41 (m, 2H), 2.10 (s, 3H), 1.83 (s, 6H). Mass: m/z 423.2 (M+H) ion present.

Cis-7-(6-(azetidin-1-yl)-4-methylpyridin-3-yl)-2-(dimethylamino)-2-phenyl-5,7-diazaspiro [3.4]octan-6-one (SC-13)

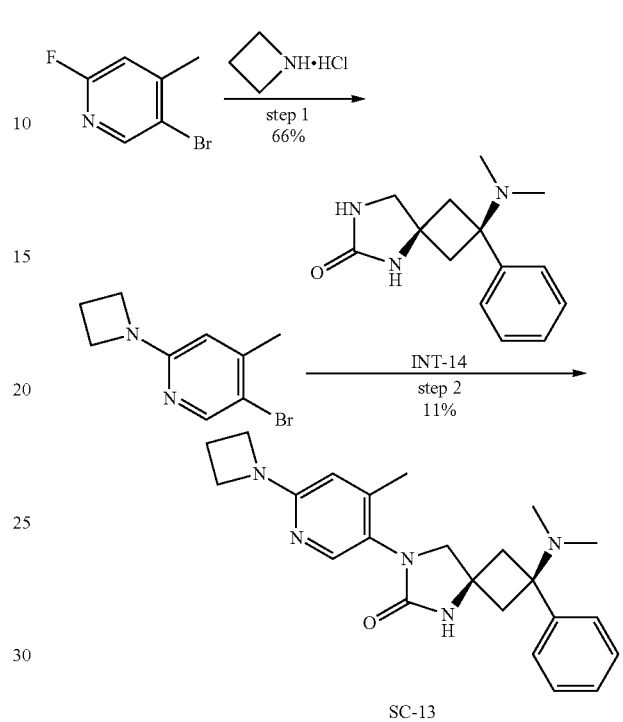

Step 1: 2-(Azetidin-1-yl)-5-bromo-4-methylpyridine

Cs₂CO₃ (3.4 g, 10.526 mmol) was added to a stirred solution of 2,5-dibromo-4-methylpyridine (1.0 g, 5.263 mmol) and azetidine hydrochloride (0.5 g, 5.263 mmol) in DMSO (10 mL) at RT. The resulting reaction mixture was heated to 90° C. and maintained under stirring for 20 h. The reaction completion was monitored by TLC To the reaction mixture, water (30 mL) was added and extracted with ethyl acetate (2×30 mL). The combined organic layer was dried over anhydrous Na₂SO₄ and concentrated under reduced pressure to afford 0.8 g (66%) of 2-(azetidin-1-yl)-5-bromo-4-methylpyridine as a pale yellow solid. (TLC system: 30% ethyl acetate in pet-ether; Rf: 0.7).

Step 2: Cis-7-(6-(azetidin-1-yl)-4-methylpyridin-3-yl)-2-(dimethylamino)-2-phenyl-5,7-diazaspiro [3.4] octan-6-one (SC-13)

In analogy to the method described for SC-12 cis-2-(dimethylamino)-2-phenyl-5,7-diazaspiro[3.4]octan-6-one (INT-14) (200 mg, 0.816 mmol) was reacted with 2-(azetidin-1-yl)-5-bromo-4-methylpyridine (278 mg, 1.224 mmol) to be converted into cis-7-(6-(azetidin-1-yl)-4-methylpyridin-3-yl)-2-(dimethylamino)-2-phenyl-5,7-diazaspiro[3.4] octan-6-one (SC-13) (35 mg, 11%). ¹H NMR (400 MHz, zDMSO-d₆): δ 7.69 (s, 1H), 7.38-7.33 (m, 2H), 7.31-7.23 (m, 3H), 7.14 (s, 1H), 6.14 (s, 1H), 3.86-3.81 (m, 4H), 3.05 (s, 2H), 2.86-2.82 (m, 2H), 2.45-2.41 (m, 2H), 2.29-2.21 (m, 2H), 1.98 (s, 3H), 1.83 (s, 6H). Mass: m/z 392.2 (M+H) ion present.

Cis-5-(5-(cyclopropylmethyl)-2-(dimethylamino)-2-(3-fluorophenyl)-6-oxo-5,7-diazaspiro [3.4]octan-7-yl)-4-methylpicolinonitrile (SC-15)

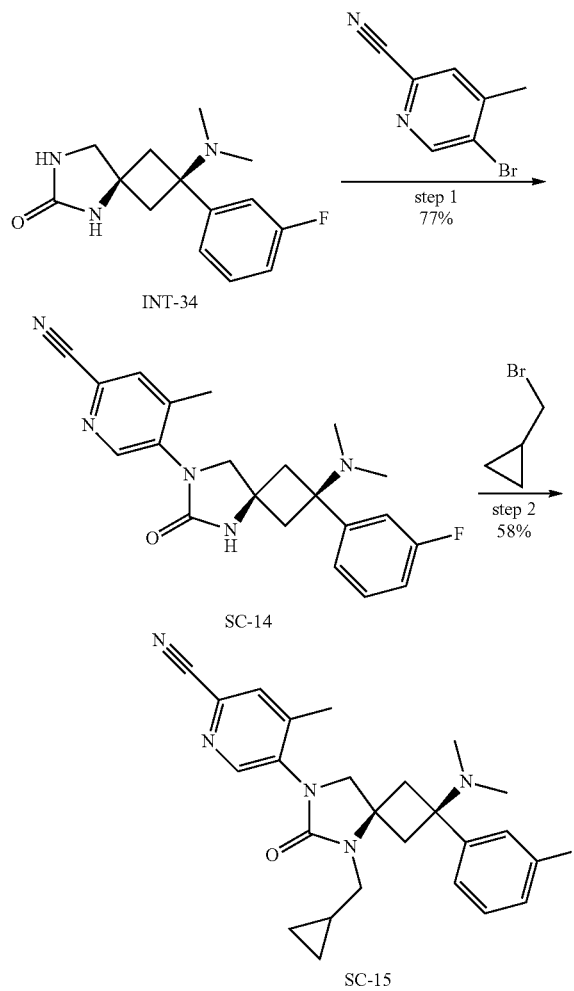

Step 1: cis-5-(2-(dimethylamino)-2-(3-fluorophenyl)-6-oxo-5,7-diazaspiro[3.4]octan-7-yl)-4-methylpicolinonitrile (SC-14)

In analogy to the method described for SC-3 cis-2-(dimethylamino)-2-(3-fluorophenyl)-5,7-diazaspiro[3.4]octan-6-one (INT-34) (120 mg, 0.456 mmol) was reacted with 5-bromo-4-methyl-pyridine-2-carbonitrile (197 mg, 0.592 mmol) to be converted into cis-5-(5-(cyclopropylmethyl)-2-(dimethylamino)-2-(3-fluorophenyl)-6-oxo-5,7-diazaspiro [3.4]octan-7-yl)-4-methylpicolinonitrile (SC-14) (133 mg, 77%). $^1$H NMR (600 MHz, DMSO-$d_6$): δ 8.46 (s, 1H), 7.89 (s, 1H), 7.66 (s, 1H), 7.41 (td, J=7.8, 6.0 Hz, 1H), 7.16-7.07 (m, 3H), 2.92-2.86 (m, 2H), 2.51-2.45 (m, 2H), 2.19 (s, 3H), 1.86 (s, 6H). Mass: m/z 380.2 (M+H) ion present.

Step 2: cis-5-(5-(cyclopropylmethyl)-2-(dimethylamino)-2-(3-fluorophenyl)-6-oxo-5,7-diazaspiro [3.4]octan-7-yl)-4-methylpicolinonitrile (SC-15)

To a solution of cis-5-(5-(cyclopropylmethyl)-2-(dimethylamino)-2-(3-fluorophenyl)-6-oxo-5,7-diazaspiro[3.4]octan-7-yl)-4-methylpicolinonitrile (SC-14) (60 mg, 0.158 mmol) in dry DMF (1.2 mL) under nitrogen atmosphere was added 60% NaH in mineral oil (9.5 mg, 0.237 mmol) and the mixture was stirred at RT. After ~5 min a solution of bromomethylcyclopropane (23 μL, 0.237 mmol) was added. The reaction mixture was stirred at RT for 1.5 h, quenched with sat. aq. NH$_4$Cl (5 mL) and extracted with DCM (2×10 mL). The combined organic layers were washed with brine, dried over Na$_2$SO$_4$(s) and concentrated to dryness. The crude material (75 mg) was purified by flash chromatography on silica gel (eluent DCM/MeOH gradient 0% to 6% methanol) to yield 40 mg (58%) cis-5-(5-(cyclopropylmethyl)-2-(dimethylamino)-2-(3-fluorophenyl)-6-oxo-5,7-diazaspiro[3.4]octan-7-yl)-4-methylpicolinonitrile (SC-15) as white solid. $^1$H NMR (600 MHz, DMSO-$d_6$): δ 8.47 (s, 1H), 7.90 (s, 1H), 7.42 (td, J=8.8, 8.3, 6.3 Hz, 1H), 7.16-7.08 (m, 3H), 3.43 (s, 2H), 3.23 (d, J=6.6 Hz, 2H), 2.85-2.79 (m, 2H), 2.71-2.65 (m, 2H), 2.18 (s, 3H), 1.88 (s, 6H), 1.13-1.03 (m, 1H), 0.56-0.47 (m, 2H), 0.39-0.31 (m, 2H). Mass: m/z 434.2 (M+H) ion present.

Cis-7-(6-(difluoromethyl)-4-methylpyridin-3-yl)-2-(dimethylamino)-2-(3-fluorophenyl)-5,7-diazaspiro [3.4]octan-6-one (SC-22)

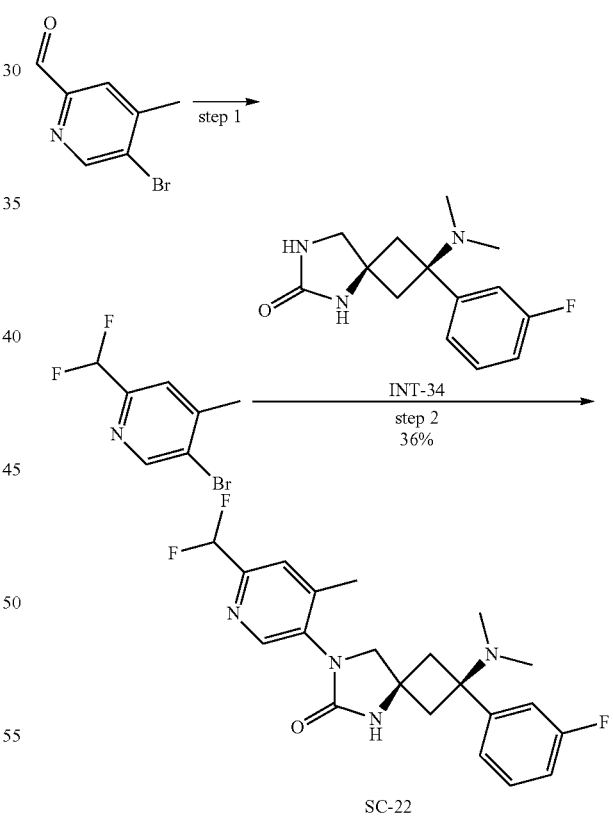

Step 1: 5-bromo-2-(difluoromethyl)-4-methylpyridine

To the solution of 5-bromo-4-methyl-pyridine-2-carbaldehyde (200 mg, 1.00 mmol) in DCM (7.7 mL) at −78° C. (diethylamino)sulfurtrifluoride (242 mg, 0.198 mL, 1.50 mmol) was added under nitrogen atmosphere. The reaction mixture was allowed to warm up to RT over 4h and stirred at RT overnight. The reaction mixture was quenched with 2 M aq. NaOH and extracted with DCM (3×). The combined organic layers were washed with brine, dried over Na₂SO₄ (s) and concentrated at 100 mbar. The resulting crude product (220 mg) was used directly in the next step.

Step 2: cis-7-(6-(difluoromethyl)-4-methylpyridin-3-yl)-2-(dimethylamino)-2-(3-fluorophenyl)-5,7-diazaspiro [3.4]octan-6-one (SC-22)

In analogy to the method described for SC-3 cis-2-(dimethylamino)-2-(3-fluorophenyl)-5,7-diazaspiro[3.4]octan-6-one (INT-34) (200 mg, 0.760 mmol) was reacted with 5-bromo-2-(difluoromethyl)-4-methylpyridine (219 mg, 0.987 mmol) to be converted into cis-7-(6-(difluoromethyl)-4-methylpyridin-3-yl)-2-(dimethylamino)-2-(3-fluorophenyl)-5,7-diazaspiro[3.4]octan-6-one (SC-22) (110 mg, 36%). ¹H NMR (600 MHz, DMSO-d₆): δ 8.38 (s, 1H), 7.54 (s, 1H), 7.51 (s, 1H), 7.41 (td, J=8.0, 6.1 Hz, 1H), 7.23-7.03 (m, 3H), 6.85 (t, J=55.0 Hz, 1H), 3.34 (s, 2H), 2.99-2.80 (m, 2H), 2.57-2.39 (m, 2H), 2.20 (s, 3H), 1.86 (s, 6H). Mass: m/z 405.2 (M+H) ion present.

Cis-5-(cyclopropylmethyl)-2-(dimethylamino)-2-(3-fluorophenyl)-7-(2-(methylsulfonyl)ethyl)-5,7-diazaspiro [3.4]octan-6-one (SC-31)

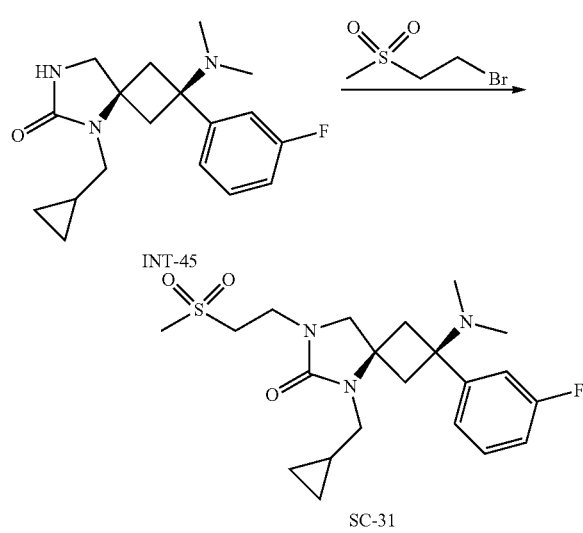

To the solution of cis-5-(cyclopropylmethyl)-2-(dimethylamino)-2-(3-fluorophenyl)-5,7-diazaspiro[3.4]octan-6-one (INT-45) (80 mg, 0.252 mmol) in THF (2.1 mL) was added 1M potassium tert-butylate in THF (0.378 mL, 0.378 mmol). The resulting mixture was stirred 0.5h at RT, cooled to 0° C. and the solution of 1-bromo-2-methylsulfonyl-ethane (71 mg, 0.378 mmol) in THF (1 mL) was added dropwise. The reaction mixture was stirred for 1h, quenched with water and extracted with ethyl acetate (3×). The combined organic layers were washed with brine, dried over Na₂SO₄(s) and concentrated to dryness. Crude product (108 mg) was further purified by column chromatography on silica gel (gradient 0 to 5% EtOH in DCM) to yield 53 mg of semi-pure product which was further purified by reversed phase HPLC to yield 28 mg (26%) of cis-5-(cyclopropyl-methyl)-2-(dimethylamino)-2-(3-fluorophenyl)-7-(2-(methylsulfonyl)ethyl)-5,7-diazaspiro[3.4]octan-6-one (SC-31) as a white solid. ¹H NMR (600 MHz, DMSO-d₆) δ 7.45 (td, J=8.0, 6.2 Hz, 1H), 7.18-7.08 (m, 3H), 3.39 (s, 2H), 3.19 (t, J=6.9 Hz, 2H), 3.10 (d, J=6.6 Hz, 2H), 2.94 (s, 2H), 2.91 (s, 3H), 2.68-2.62 (m, 2H), 2.60-2.54 (m, 2H), 1.85 (s, 6H), 1.06-0.93 (m, 1H), 0.51-0.43 (m, 2H), 0.34-0.26 (m, 2H). Mass: m/z 424.2 (M+H) ion present.

Cis-5-(cyclopropylmethyl)-2-(dimethylamino)-2-(3-fluorophenyl)-7-(2-methoxy-2-methylpropyl)-5,7-diazaspiro[3.4]octan-6-one (SC-37)

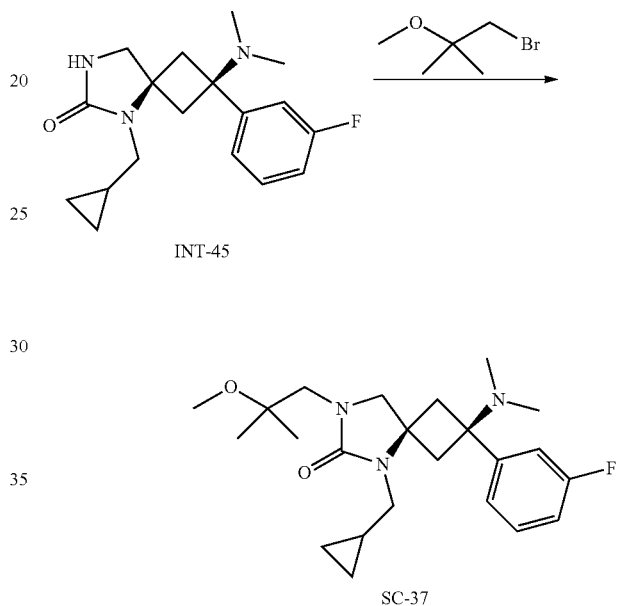

Anhydrous NaOH powder (50.4 mg, 1.26 mmol) was suspended in anhydrous DMSO (5.25 mL) under nitrogen atmosphere and the resulting mixture was stirred 40 min at RT. Cis-5-(cyclopropylmethyl)-2-(dimethylamino)-2-(3-fluorophenyl)-5,7-diazaspiro[3.4]octan-6-one (INT-45) (100 mg, 0.315 mmol) and 1-bromo-2-methoxy-2-methylpropane (79 mg, 0.473 mmol) were added. The resulting mixture was stirred 22h at 90° C. and a new portion of 1-bromo-2-methoxy-2-methylpropane (26.3 mg, 0.158 mmol) was added. The reaction mixture was stirred for 4h, quenched with brine (30 mL) and extracted with ethyl acetate (3×). The combined organic layers were dried over Na₂SO₄(s) and concentrated to dryness. Crude product (152 mg) was purified by column chromatography on silica gel (gradient 1 to 5% EtOH in DCM) to yield 78 mg (61%) of cis-5-(cyclopropylmethyl)-2-(dimethylamino)-2-(3-fluorophenyl)-7-(2-methoxy-2-methylpropyl)-5,7-diazaspiro[3.4]octan-6-one (SC-37). ¹H NMR (600 MHz, DMSO-d₆): δ 7.48-7.41 (m, 1H), 7.17-7.11 (m, 3H), 3.08 (d, J=6.5 Hz, 2H), 2.93 (s, 2H), 2.91 (s, 2H), 2.90 (s, 3H), 2.64-2.59 (m, 2H), 2.56-2.50 (m, 3H), 1.86 (s, 6H), 1.04-0.97 (m, 1H), 0.96 (s, 6H), 0.49-0.42 (m, 2H), 0.31-0.24 (m, 2H). Mass: m/z 404.3 (M+H) ion present.

Cis-2-(dimethylamino)-2-(3-fluorophenyl)-7-(4-morpholinobenzyl)-5,7-diazaspiro [3.4]octan-6-one (SC-41)

Cis-3-(5-(cyclopropylmethyl)-2-(dimethylamino)-2-(3-fluorophenyl)-6-oxo-5,7-diazaspiro [3.4]octan-7-yl)propanenitrile (SC-44)

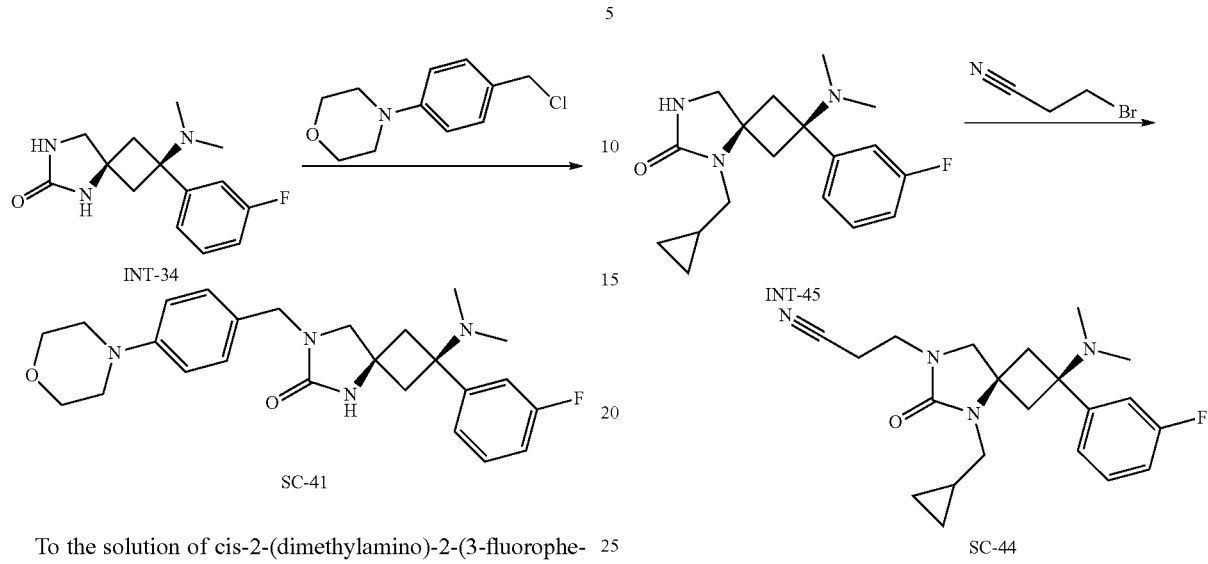

To the solution of cis-2-(dimethylamino)-2-(3-fluorophenyl)-5,7-diazaspiro[3.4]octan-6-one (INT-34) (100 mg, 0.380 mmol) in dioxane (15.2 mL) was added potassium tert-butylate (93.8 mg, 0.836 mmol) and the resulting mixture was stirred 10 min at RT. 4-[4-(Chloromethyl)phenyl] morpholine hydrochloride (104 mg, 0.418 mmol) was added and the reaction mixture was stirred at RT for 3h. A new portion of potassium tert-butylate (42.6 mg, 0.380 mmol) was added. The reaction mixture was stirred further 19h at RT and concentrated to dryness. The solid residue was taken up in water (10 mL)/ethyl acetate (20 mL), organic phase separated and aqueous phase extracted with ethyl acetate (20 mL). The combined organic layers were washed with brine, dried over $Na_2SO_4$(s) and concentrated to dryness. Crude product (158 mg) was further purified by column chromatography on silica gel (gradient 0 to 7% (0.5M $NH_3$ in MeOH) in DCM) to yield 46 mg of semi-pure product which was further purified by reversed phase HPLC to yield 27 mg (16%) of cis-2-(dimethylamino)-2-(3-fluorophenyl)-7-(4-morpholinobenzyl)-5,7-diazaspiro[3.4]octan-6-one (SC-41) as a white solid. $^1$H NMR (600 MHz, DMSO-$d_6$): δ 7.38 (td, J=7.6, 5.9 Hz, 1H), 7.12-7.03 (m, 3H), 6.95 (d, J=8.3 Hz, 3H), 6.87-6.81 (m, 2H), 4.02 (s, 2H), 3.74-3.69 (m, 4H), 3.08-3.03 (m, 4H), 2.70-2.65 (m, 4H), 2.39-2.33 (m, 2H), 1.81 (s, 6H). Mass: m/z 439.3 (M+H) ion present.

To the solution of cis-5-(cyclopropylmethyl)-2-(dimethylamino)-2-(3-fluorophenyl)-5,7-diazaspiro[3.4]octan-6-one (INT-45) (130 mg, 0.410 mmol) in DMSO (1.7 mL) was added potassium tert-butylate (68.9 mg, 0.614 mmol) at RT under nitrogen atmosphere. The resulting mixture was stirred 15 min at RT. 3-Bromopropionitrile (51 µL, 0.614 mmol) in DMSO (1.7 mL) was added dropwise and the reaction mixture was stirred at RT for 18h. A new portion of 3-bromopropionitrile (17 µL, 0.205 mmol) was added. The reaction mixture was stirred further 6h at RT, quenched with brine (30 mL) and extracted with ethyl acetate (3×). The combined organic layers were dried over $Na_2SO_4$(s) and concentrated to dryness. Crude product (208 mg) was further purified by column chromatography on silica gel (gradient 2 to 5% EtOH in DCM) to yield 105 mg (87%) of cis-3-(5-(cyclopropylmethyl)-2-(dimethylamino)-2-(3-fluorophenyl)-6-oxo-5,7-diazaspiro[3.4]octan-7-yl)propanenitrile (SC-44) as a white solid. $^1$H NMR (600 MHz, DMSO-$d_6$+TFA): δ 7.68-7.54 (m, 3H), 7.41 (td, J=8.5, 2.5 Hz, 1H), 3.24 (d, J=6.7 Hz, 2H), 3.21 (t, J=6.5 Hz, 2H), 3.07-3.02 (m, 2H), 3.01-2.96 (m, 2H), 2.85 (s, 2H), 2.56-2.52 (m, 8H), 1.12-0.99 (m, 1H), 0.47-0.39 (m, 2H), 0.38-0.30 (m, 2H). Mass: m/z 371.2 (M+H) ion present.

The following compounds were prepared in analogy and by combining previously described methods:

| Example | Chemical name | Chemical structure | Reactant I | Reactant II | in analogy to method | ¹H NMR data | m/z (M + H)⁺ |
|---|---|---|---|---|---|---|---|
| SC-4 | trans-2-(dimethylamino)-7-(2-(1,1-dioxidothiomorpholino)-2-oxoethyl)-2-phenyl-5,7-diazaspiro[3.4]octan-6-one | 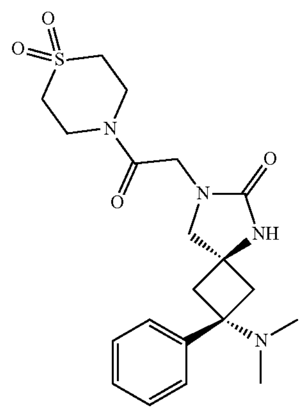 [SMILES: CN(C)[C@]1(c2ccccc2)C[C@]2(CN(CC(=O)N3CCS(=O)(=O)CC3)C(=O)N2)C1] | INT-24 | thiomorpholine 1,1-dioxide | SC-2 | ¹H NMR (400 MHz, DMSO-d6) δ 7.34 (t, J = 7.5 Hz, 2H), 7.24 (t, J = 7.3 Hz, 1H), 7.03 (d, J = 7.3 Hz, 2H), 6.77 (s, 1H), 4.01 (s, 2H), 3.90-3.77 (m, 4H), 3.63 (s, 2H), 3.28 (s, 2H), 3.11 (s, 2H), 2.65 (d, J = 12.3 Hz, 2H), 2.29 (d, J = 12.2 Hz, 2H), 1.93 (s, 6H). | 421.2 |
| SC-5 | trans-5-(2-(dimethylamino)-6-oxo-2-phenyl-5,7-diazaspiro[3.4]octan-7-yl)-4-methoxypyrimidine-2-carbonitrile | 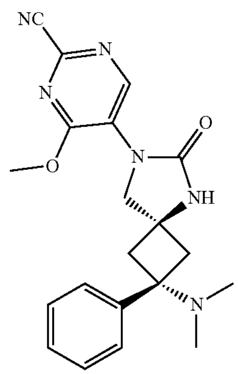 | INT-22 | 5-bromo-4-methoxypyrimidine-2-carbonitrile | SC-3 | ¹H NMR (400 MHz, DMSO-d6) δ 8.79 (s, 1H), 7.71 (s, 1H), 7.36 (t, J = 7.5 Hz, 2H), 7.26 (t, J = 7.3 Hz, 1H), 7.05 (d, J = 7.1 Hz, 2H), 4.13 (s, 2H), 4.06 (s, 3H), 2.75 (dd, J = 10.1, 2.6 Hz, 2H), 2.42-2.34 (m, 2H), 1.95 (s, 6H). | 379.2 |

| Example | Chemical name | Chemical structure | Reactant I | Reactant II | in analogy to method | $^1$H NMR data | m/z (M + H)$^+$ |
|---|---|---|---|---|---|---|---|
| SC-7 | trans-5-(cyclobutylmethyl)-2-(dimethylamino)-7-(2-(1,1-dioxidothiomorpholino)-2-oxoethyl)-2-phenyl-5,7-diazaspiro[3.4]octan-6-one | 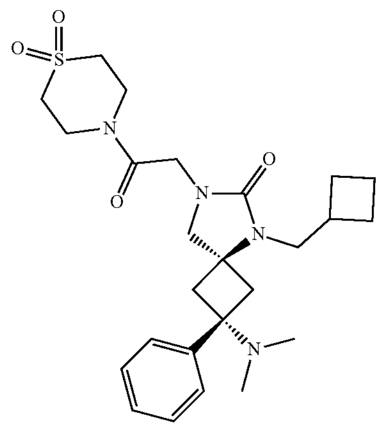 [SMILES: CN(C)[C@]1(c2ccccc2)C[C@]2(CN(CC(=O)N3CCS(=O)(=O)CC3)C(=O)N2CC2CCC2)C1] | INT-21 | 2-bromo-1-(1,1-dioxidothiomorpholino)etha-none | SC-6 | $^1$H NMR (400 MHz, DMSO-d$_6$) δ 7.37 (t, J = 7.5 Hz, 2H), 7.26 (t, J = 7.3 Hz, 1H), 7.08 (d, J = 7.3 Hz, 2H), 4.06 (s, 2H), 3.84 (s, 4H), 3.62 (s, 2H), 3.28 (m, 2H), 3.11 (m, 2H), 2.89 (d, J = 7.2 Hz, 2H), 2.55 (m, 2H), 2.41 (d, J = 12.8 Hz, 2H), 2.33 (m, 1H), 1.92 (s, 6H), 1.86-1.76 (m, 2H), 1.68 (m, 2H), 1.53 (m, 2H). | 489.3 |
| SC-8 | cis-2-(5-(cyclobutylmethyl)-2-(dimethylamino)-6-oxo-2-phenyl-5,7-diazaspiro[3.4]octan-7-yl)acetamide | 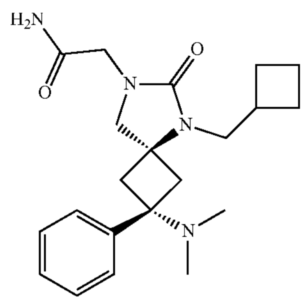 [SMILES: CN(C)[C@]1(c2ccccc2)C[C@]2(CN(CC(N)=O)C(=O)N2CC2CCC2)C1] | INT-26 | ammonium chloride | SC-1 | $^1$H-NMR (400 MHz, CDCl3) δ 7.38 (m, 2H), 7.35-7.29 (m, 1H), 7.23-7.17 (m, 2H), 6.25 (bs, 1H), 5.21 (bs, 1H), 3.64 (s, 2H), 3.33 (d, J = 7.3 Hz, 2H), 2.85 (s, 2H), 2.69-2.51 (m, 5H), 2.04 (m, 2H), 1.94 (s, 6H), 1.89-1.73 (m, 4H). | 371.3 |

-continued

| Example | Chemical structure | Chemical name | Reactant I | Reactant II | in analogy to method | ¹H NMR data | m/z (M + H)⁺ |
|---|---|---|---|---|---|---|---|
| SC-10 | 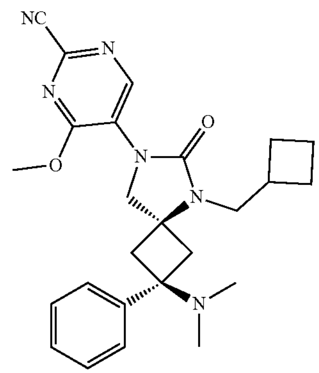 [SMILES: COc1nc(C#N)ncc1N1C[C@]2(C[C@](c3ccccc3)(N(C)C)C2)N(CC2CCC2)C1=O] | cis-5-(5-(cyclobutylmethyl)-2-(dimethylamino)-6-oxo-2-phenyl-5,7-diazaspiro[3.4]octan-7-yl)-4-methoxypyrimidine-2-carbonitrile | INT-13 | 5-bromo-4-methoxypyrimidine-2-carbonitrile | SC-3 | ¹H NMR (400 MHz, CDCl₃) δ 8.85 (s, 1H), 7.41 (m, 2H), 7.33 (t, J = 7.3 Hz, 1H), 7.24 (m, 2H), 3.85 (s, 3H), 3.42 (d, J = 7.3 Hz, 2H), 3.36 (s, 2H), 2.78-2.70 (m, 2H), 2.67 (m, 1H), 2.63-2.59 (m, 2H), 2.12-2.03 (m, 2H), 1.97 (s, 6H), 1.85 (m, 4H). | 447.3 |
| SC-11 | 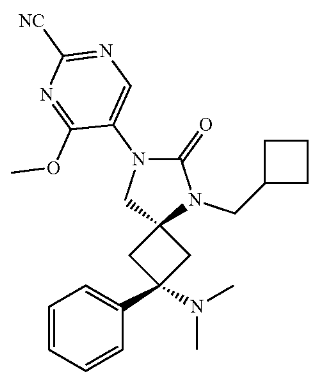 [SMILES: COc1nc(C#N)ncc1N1C[C@]2(C[C@@](c3ccccc3)(N(C)C)C2)N(CC2CCC2)C1=O] | trans-5-(5-(cyclobutylmethyl)-2-(dimethylamino)-6-oxo-2-phenyl-5,7-diazaspiro[3.4]octan-7-yl)-4-methoxypyrimidine-2-carbonitrile | INT-21 | 5-bromo-4-methoxypyrimidine-2-carbonitrile | SC-3 | ¹H NMR (400 MHz, CDCl₃) δ 8.87 (s, 1H), 7.39 (t, J = 7.4 Hz, 2H), 7.30 (t, J = 7.3 Hz, 1H), 7.11-7.00 (m, 2H), 4.16 (s, 2H), 4.10 (s, 3H), 3.07 (d, J = 7.2 Hz, 2H), 2.65-2.54 (m, 4H), 2.46 (m, 1H), 2.02 (s, 6H), 1.92 (ddt, J = 11.3, 8.2, 3.4 Hz, 2H), 1.76 (tdd, J = 14.6, 8.6, 2.7 Hz, 2H), 1.68-1.58 (m, 2H). | 447.3 |

-continued

| Example | Chemical structure | Chemical name | Reactant I | Reactant II | in analogy to method | ¹H NMR data | m/z (M + H)⁺ |
|---|---|---|---|---|---|---|---|
| SC-16 | 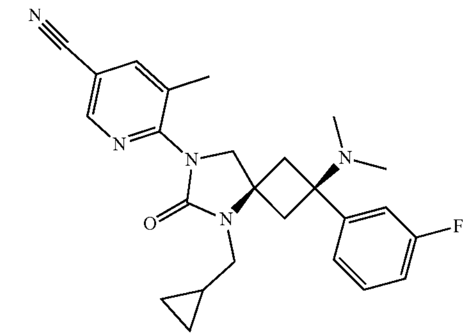 [SMILES: Cc1cc(C#N)cnc1N1C[C@]2(C[C@](c3cccc(F)c3)(N(C)C)C2)N(CC2CC2)C1=O] | Cis-6-(5-(cyclopropylmethyl)-2-(dimethylamino)-2-(3-fluorophenyl)-6-oxo-5,7-diazaspiro[3.4]octan-7-yl)-5-methylnicotinonitrile | INT-34 | 6-bromo-5-methyl-pyridine-3-carbonitrile (step 1); bromomethylcyclopropane (step 2) | SC-15 | ¹H NMR (600 MHz, DMSO-d6) δ 8.56 (d, J = 2.2 Hz, 1H), 8.13-8.09 (m, 1H), 7.44 (td, J = 8.0, 6.2 Hz, 1H), 7.14 (ddd, J = 16.1, 7.8, 2.7 Hz, 3H), 3.45 (s, 2H), 3.22 (d, J = 6.7 Hz, 2H), 2.89-2.83 (m, 2H), 2.69-2.62 (m, 2H), 2.24 (s, 3H), 1.88 (s, 6H), 1.10-1.03 (m, 1H), 0.54-0.46 (m, 2H), 0.38-0.29 (m, 2H). | 434.2 |
| SC-17 | 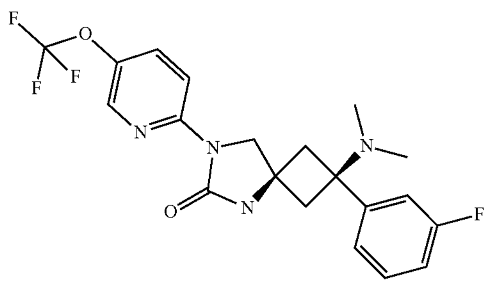 [SMILES: CN(C)[C@]1(c2cccc(F)c2)C[C@@]2(CN(c3ccc(OC(F)(F)F)cn3)C(=O)N2)C1] | Cis-2-(dimethylamino)-2-(3-fluorophenyl)-7-(5-(trifluoromethoxy)pyridin-2-yl)-5,7-diazaspiro[3.4]octan-6-one | INT-34 | 2-bromo-5-(trifluoromethoxy)pyridine | SC-3 | ¹H NMR (600 MHz, DMSO-d6) δ 8.25-8.18 (m, 2H), 7.93 (s, 1H), 7.76 (dd, J = 9.5, 3.0 Hz, 1H), 7.47 (td, J = 7.9, 6.2 Hz, 1H), 7.22-7.13 (m, 3H), 3.50 (s, 2H), 2.91-2.85 (m, 2H), 2.49-2.43 (m, 2H), 1.84 (s, 6H). | 425.2 |
| SC-18 | 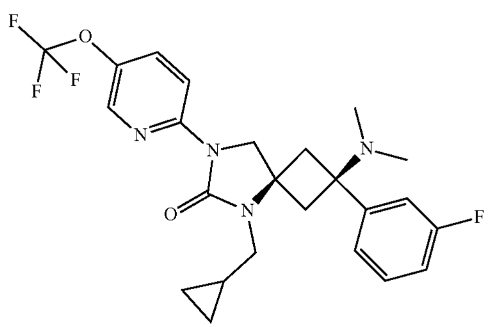 [SMILES: CN(C)[C@]1(c2cccc(F)c2)C[C@@]2(CN(c3ccc(OC(F)(F)F)cn3)C(=O)N2CC2CC2)C1] | Cis-5-(cyclopropylmethyl)-2-(dimethylamino)-2-(3-fluorophenyl)-7-(5-(trifluoromethoxy)pyridin-2-yl)-5,7-diazaspiro[3.4]octan-6-one | SC-17 | bromomethylcyclopropane | SC-15 (step 2) | ¹H NMR (600 MHz, DMSO-d6) δ 8.26-8.18 (m, 2H), 7.79 (ddd, J = 9.3, 2.9, 1.1 Hz, 1H), 7.48 (td, J = 8.0, 6.3 Hz, 1H), 7.23-7.14 (m, 3H), 3.54 (s, 2H), 3.25 (d, J = 6.6 Hz, 2H), 2.84-2.77 (m, 2H), 2.69-2.63 (m, 2H), 1.87 (s, 6H), 1.15-1.00 (m, 1H), 0.56-0.48 (m, 2H), 0.41-0.33 (m, 2H). | 479.2 |

-continued

| Example | Chemical name | Chemical structure | Reactant I | Reactant II | in analogy to method | ¹H NMR data | m/z (M + H)⁺ |
|---|---|---|---|---|---|---|---|
| SC-19 | Cis-2-(dimethylamino)-7-(4-methyl-6-morpholinopyridin-3-yl)-2-phenyl-5,7-diazaspiro[3.4]octan-6-one | 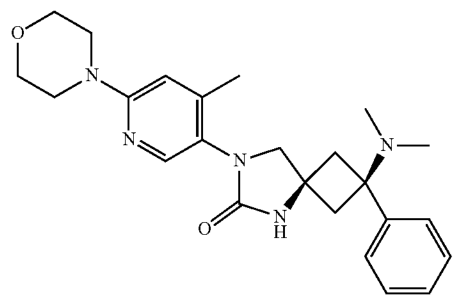 [SMILES: Cc1cc(N2CCOCC2)ncc1N1C[C@]2(C[C@](c3ccccc3)(N(C)C)C2)NC1=O] | INT-14 (step 2) | 5-bromo-2-fluoro-4-methylpyridine, morpholine (step 1) | SC-13 | ¹H NMR (DMSO-d6): δ 7.78 (s, 1H), 7.39-7.31 (m, 2H), 7.32-7.27 (m, 2H), 7.26-7.24 (m, 1H), 7.19 (s, 1H), 6.62 (s, 1H), 3.65-3.62 (m, 4H), 3.38-3.36 (m, 4H), 3.07 (s, 2H), 2.85-81 (m, 2H), 2.45-2.41 (m, 2H), 2.01 (s, 3H), 1.84 (s, 6H). | 422.3 |
| SC-20 | Cis-2-(dimethylamino)-7-(6-(2-hydroxypropan-2-yl)-4-methylpyridin-3-yl)-2-phenyl-5,7-diazaspiro[3.4]octan-6-one | 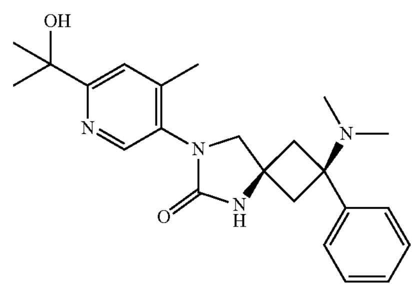 [SMILES: Cc1cc(C(C)(C)O)ncc1N1C[C@]2(C[C@](c3ccccc3)(N(C)C)C2)NC1=O] | INT-14 | 2-(5-bromo-4-methylpyridin-2-yl)propan-2-ol | SC-12 | ¹H NMR (DMSO-d₆): δ 8.13 (s, 1H), 7.44 (s, 1H), 7.37-7.24 (m, 6H), 5.13 (bs, 1H), 3.17 (s, 2H), 2.87 (d, 2H), 2.46 (d, 2H), 2.10 (s, 3H), 1.84 (s, 6H), 1.36 (s, 6H). | 395.3 |
| SC-21 | Cis-2-(dimethylamino)-7-(4-(2-hydroxypropan-2-yl)-2-methylphenyl)-2-phenyl-5,7-diazaspiro[3.4]octan-6-one | 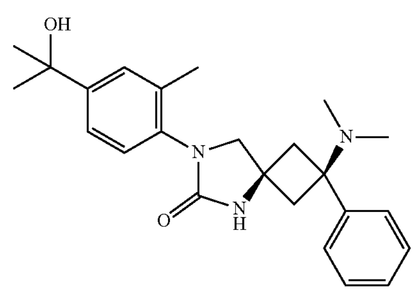 [SMILES: Cc1cc(C(C)(C)O)ccc1N1C[C@]2(C[C@](c3ccccc3)(N(C)C)C2)NC1=O] | INT-14 | 2-(4-bromo-3-methylphenyl)propan-2-ol | SC-12 | ¹H NMR (DMSO-d₆): δ 7.37-7.32 (m, 2H), 7.31-7.28 (m, 2H), 7.27-7.22 (m, 2H), 7.18-7.11 (m, 2H), 6.95-6.92 (m, 1H), 4.91 (s, 1H), 3.08 (s, 2H), 2.86-2.84 (m, 2H), 2.45-2.43 (m, 2H), 2.06 (s, 3H), 1.84 (s, 6H), 1.35 (s, 6H). | 394.2 |

| Example | Chemical name | Chemical structure | Reactant I | Reactant II | in analogy to method | ¹H NMR data | m/z (M + H)⁺ |
|---|---|---|---|---|---|---|---|
| SC-23 | Cis-2-(dimethylamino)-5-(((3-fluorooxetan-3-yl)methyl)-2-(3-fluorophenyl)-7-(5-(trifluoromethoxy)pyridin-2-yl)-5,7-diazaspiro[3.4]octan-6-one | 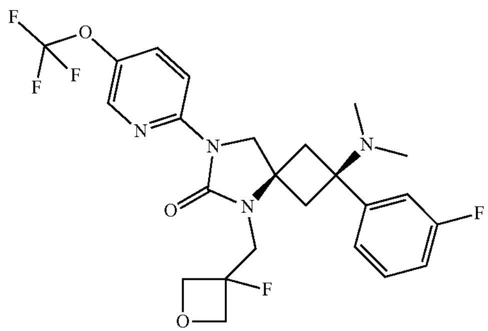 [SMILES: CN(C)[C@]1(c2cccc(F)c2)C[C@@]2(CN(c3ccc(OC(F)(F)F)cn3)C(=O)N2CC2(F)COC2)C1] | SC-17 | (3-fluorooxetan-3-yl)methyl 4-methylbenzenesulfonate | SC-15 (step 2) | ¹H NMR (600 MHz, DMSO-d₆) δ 8.26 (d, J = 2.9 Hz, 1H), 8.20 (d, J = 9.3 Hz, 1H), 7.87-7.77 (m, 1H), 7.47 (td, J = 7.8, 6.0 Hz, 1H), 7.24-7.12 (m, 3H), 4.86-4.74 (m, 2H), 4.64 (dd, J = 20.8, 8.1 Hz, 2H), 3.91 (d, J = 21.4 Hz, 2H), 3.54 (s, 2H), 2.84-2.75 (m, 2H), 2.63-2.51 (m, 2H), 1.84 (s, 6H). | 513.2 |
| SC-24 | Cis-5-(cyclopropylmethyl)-7-(6-(difluoromethyl)-4-methylpyridin-3-yl)-2-(dimethylamino)-2-(3-fluorophenyl)-5,7-diazaspiro[3.4]octan-6-one | 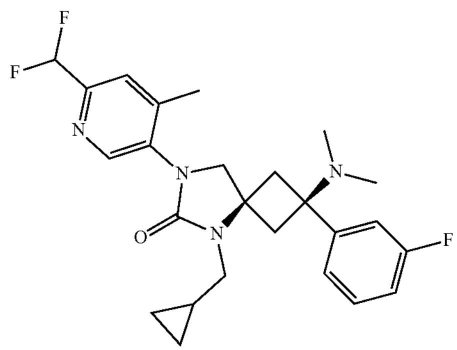 [SMILES: Cc1cc(C(F)F)ncc1N1C[C@]2(C[C@](c3cccc(F)c3)(N(C)C)C2)N(CC2CC2)C1=O] | SC-22 | bromomethylcyclopropane | SC-15 (step 2) | ¹H NMR (600 MHz, DMSO-d₆) δ 8.40 (s, 1H), 7.56 (s, 1H), 7.45-7.36 (m, 1H), 7.23-7.03 (m, 3H), 6.87 (t, J = 55.0 Hz, 1H), 3.22 (d, J = 6.6 Hz, 2H), 2.98-2.74 (m, 2H), 2.82-2.60 (m, 2H), 2.20 (s, 3H), 1.89 (s, 6H), 1.16-1.04 (m, 1H), 0.53 (dtd, J = 8.3, 4.1, 1.9 Hz, 2H), 0.34 (dd, J = 4.8, 1.7 Hz, 2H). | 459.2 |
| SC-25 | Cis-2-(dimethylamino)-7-(2-morpholinopyrimidin-5-yl)-2-phenyl-5,7-diazaspiro[3.4]octan-6-one | 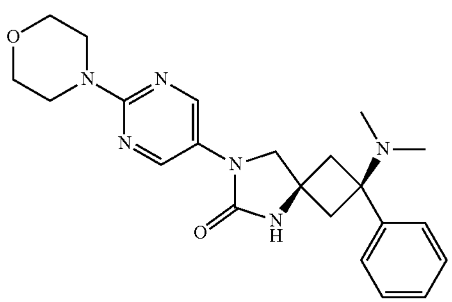 [SMILES: CN(C)[C@]1(c2ccccc2)C[C@@]2(CN(c3cnc(N4CCOCC4)nc3)C(=O)N2)C1] | INT-14 | 4-(5-bromopyrimidin-2-yl)morpholine | SC-12 | ¹H NMR (DMSO-d₆): δ 8.31 (s, 2H), 7.54 (s, 1H), 7.40-7.37 (m, 2H), 7.31-7.28 (m, 3H), 3.62-3.60 (m, 4H), 3.57-3.55 (m, 4H), 3.29 (s, 2H), 2.85-2.82 (m, 2H), 2.48-2.44 (m, 2H), 1.83 (s, 6H). | 409.3 |

-continued

| Example | Chemical name | Chemical structure | Reactant I | Reactant II | in analogy to method | ¹H NMR data | m/z (M + H)⁺ |
|---|---|---|---|---|---|---|---|
| SC-26 | Cis-2-(dimethylamino)-5-((1-fluorocyclopropyl)methyl)-2-(3-fluorophenyl)-7-(5-(trifluoromethoxy)pyridin-2-yl)-5,7-diazaspiro[3.4]octan-6-one | 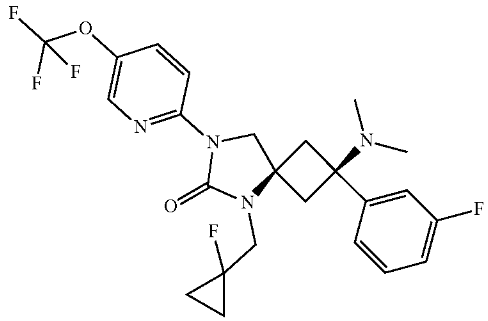 [SMILES: CN(C)[C@]1(c2cccc(F)c2)C[C@@]2(CN(c3ccc(OC(F)(F)F)cn3)C(=O)N2CC2(F)CC2)C1] | SC-17 | (1-fluorocyclopropyl)methyl 4-methylbenzenesulfonate | SC-15 (step 2) | ¹H NMR (600 MHz, DMSO-d₆): δ 8.26 (d, J = 2.9 Hz, 1H), 8.20 (d, J = 9.3 Hz, 1H), 7.81 (ddd, J = 9.3, 2.9, 1.1 Hz, 1H), 7.48 (td, J = 7.7, 6.0 Hz, 1H), 7.19 (dd, J = 9.9, 8.0 Hz, 3H), 3.79 (d, J = 20.6 Hz, 2H), 3.58 (s, 2H), 2.86-2.77 (m, 2H), 2.77-2.66 (m, 2H), 1.87 (s, 6H), 1.10-1.00 (m, 2H), 0.98-0.86 (m, 2H). | 497.2 |
| SC-27 | Cis-2-(dimethylamino)-2-(3-fluorophenyl)-5-((1-hydroxycyclobutyl)methyl)-7-(5-(trifluoromethoxy)pyridin-2-yl)-5,7-diazaspiro[3.4]octan-6-one | 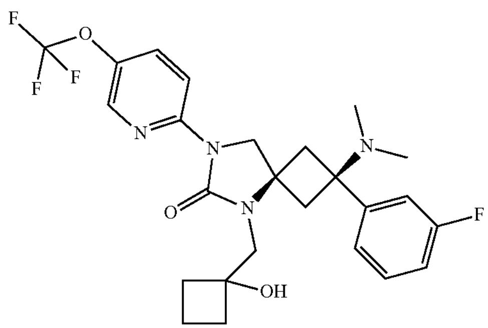 [SMILES: CN(C)[C@]1(c2cccc(F)c2)C[C@@]2(CN(c3ccc(OC(F)(F)F)cn3)C(=O)N2CC2(O)CCC2)C1] | SC-17 | [1-[tert-butyl(dimethyl)silyl]oxycyclobutyl]methyl 4-methylbenzenesulfonate | SC-15 (step 2) | ¹H NMR (600 MHz, DMSO-d₆): δ 8.25 (d, J = 2.9 Hz, 1H), 8.21 (d, J = 9.3 Hz, 1H), 7.82-7.76 (m, 1H), 7.47 (td, J = 8.0, 6.3 Hz, 1H), 7.17 (dddt, J = 10.5, 5.7, 4.3, 1.9 Hz, 3H), 3.50 (s, 2H), 3.44 (s, 2H), 2.79-2.69 (m, 4H), 2.16 (tt, J = 8.7, 3.1 Hz, 2H), 1.91 (qd, J = 9.4, 2.7 Hz, 2H), 1.84 (s, 6H), 1.72-1.62 (m, 1H), 1.60 -1.51 (m, 1H). | 509.2 |
| SC-28 | Cis-5-(cyclopropylmethyl)-2-(dimethylamino)-2-(3-fluorophenyl)-7-(4-(2-hydroxypropan-2-yl)phenyl)-5,7-diazaspiro[3.4]octan-6-one | 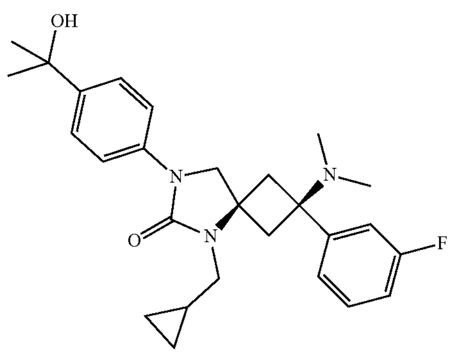 [SMILES: CN(C)[C@]1(c2cccc(F)c2)C[C@@]2(CN(c3ccc(C(C)(C)O)cc3)C(=O)N2CC2CC2)C1] | INT-34 | 2-(4-bromo-3-methylphenyl)propan-2-ol (step 1); bromomethylcyclopropane (step 2) | SC-15 | ¹H NMR (600 MHz, DMSO-d₆) δ 7.46 (td, J = 8.1, 6.2 Hz, 1H), 7.34-7.28 (m, 2H), 7.22-7.19 (m, 2H), 7.19-7.12 (m, 3H), 4.88 (d, J = 0.8 Hz, 1H), 3.56 (s, 2H), 3.22 (d, J = 6.6 Hz, 2H), 2.80-2.72 (m, 2H), 2.69-2.63 (m, 2H), 1.88 (s, 6H), 1.36 (s, 6H), 1.08 (ddt, J = 9.7, 8.0, 3.1 Hz, 1H), 0.54-0.46 (m, 2H), 0.38-0.30 (m, 2H). | 452.3 |

-continued

| Example | Chemical name | Chemical structure | Reactant I | Reactant II | in analogy to method | ¹H NMR data | m/z (M + H)⁺ |
|---|---|---|---|---|---|---|---|
| SC-29 | Cis-2-(dimethylamino)-5-((3-fluorooxetan-3-yl)methyl)-2-phenyl-7-(5-(trifluoromethoxy)pyridin-2-yl)-5,7-diazaspiro[3.4]octan-6-one | 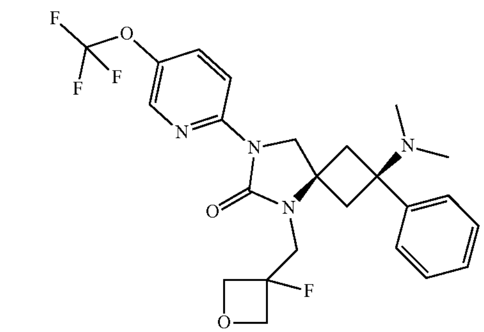 [SMILES: CN(C)[C@]1(c2ccccc2)C[C@@]2(CN(c3ccc(OC(F)(F)F)cn3)C(=O)N2CC2(F)COC2)C1] | INT-14 | 2-bromo-5-(trifluoromethoxy)pyridine (step 1); (3-fluorooxetan-3-yl)methyl 4-methylbenzenesulfonate (step 2) | SC-15 | ¹H NMR (600 MHz, DMSO-d₆) δ 8.25 (d, J = 2.9 Hz, 1H), 8.19 (d, J = 9.2 Hz, 1H), 7.82 (dd, J = 9.2, 2.9 Hz, 1H), 7.43 (t, J = 7.5 Hz, 2H), 7.40-7.29 (m, 3H), 4.80 (ddd, J = 21.7, 7.9, 1.3 Hz, 2H), 4.64 (dd, J = 20.8, 8.1 Hz, 2H), 3.91 (d, J = 21.3 Hz, 2H), 3.51 (s, 2H), 2.84-2.74 (m, 2H), 2.63-2.51 (m, 2H), 1.83 (s, 6H). | 495.2 |
| SC-30 | Cis-5-(cyclopropylmethyl)-2-(dimethylamino)-7-((6-fluorophenyl)-7-((6-(trifluoromethyl)pyridin-3-yl)methyl)-5,7-diazaspiro[3.4]octan-6-one | 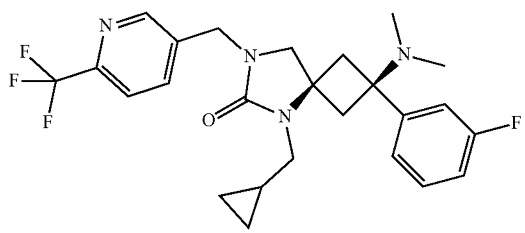 [SMILES: CN(C)[C@]1(c2cccc(F)c2)C[C@@]2(CN(Cc3ccc(C(F)(F)F)nc3)C(=O)N2CC2CC2)C1] | INT-45 | 5-(Chloromethyl)-2-(trifluoromethyl)pyridine | SC-15 (step 2) | ¹H NMR (400 MHz, DMSO-d₆): δ 8.53 (d, J = 1.9 Hz, 1H), 7.88-7.77 (m, 2H), 7.39 (q, J = 7.6, 7.1 Hz, 1H), 7.14-7.04 (m, 3H), 4.31 (s, 2H), 3.14 (d, J = 6.5 Hz, 2H), 2.82 (s, 2H), 2.67-2.54 (m, 4H), 1.83 (s, 6H), 1.10-0.99 (m, 1H), 0.54-0.43 (m, 2H), 0.37-0.26 (m, 2H). | 477.2 |
| SC-32 | Cis-5-(cyclopropylmethyl)-2-(dimethylamino)-2-phenyl-7-(5-(trifluoromethoxy)pyridin-2-yl)-5,7-diazaspiro[3.4]octan-6-one | 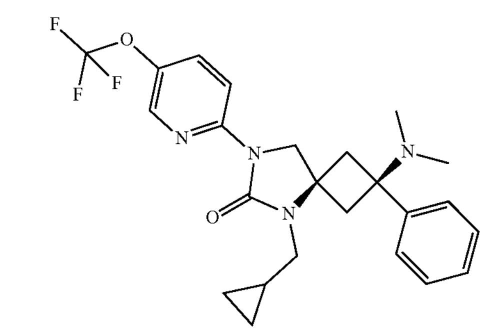 [SMILES: CN(C)[C@]1(c2ccccc2)C[C@@]2(CN(c3ccc(OC(F)(F)F)cn3)C(=O)N2CC2CC2)C1] | INT-14 | 2-bromo-5-(trifluoromethoxy)pyridine (step 1); bromomethylcyclopropane (step 2) | SC-15 | ¹H NMR (600 MHz, DMSO-d₆) δ 8.24-8.19 (m, 2H), 7.81-7.76 (m, 1H), 7.44 (t, J = 7.6 Hz, 2H), 7.38-7.32 (m, 3H), 3.51 (s, 2H), 3.25 (d, J = 6.7 Hz, 2H), 2.84-2.78 (m, 2H), 2.69-2.64 (m, 2H), 1.85 (s, 6H), 1.10 (ddt, J = 9.7, 8.1, 3.2 Hz, 1H), 0.53 (dt, J = 10.3, 2.9 Hz, 2H), 0.41-0.33 (m, 2H). | 461.2 |

-continued

| Example | Chemical name | Chemical structure | Reactant I | Reactant II | in analogy to method | ¹H NMR data | m/z (M + H)⁺ |
|---|---|---|---|---|---|---|---|
| SC-33 | Cis-5-(cyclopropylmethyl)-2-(dimethylamino)-7-((3-fluorooxetan-3-yl)methyl)-2-(3-fluorophenyl)-5,7-diazaspiro[3.4]octan-6-one | 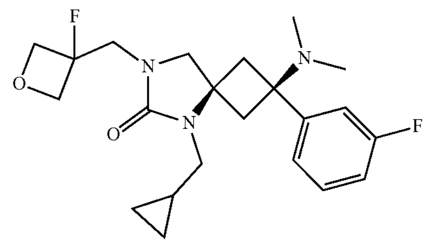 [SMILES: CN(C)[C@]1(c2cccc(F)c2)C[C@@]2(CN(CC3(F)COC3)C(=O)N2CC2CC2)C1] | INT-45 | (3-fluorooxetan-3-yl)methyl 4-methylbenzenesulfonate | SC-15 (step 2) | ¹H NMR (600 MHz, DMSO-d₆) δ 7.44 (q, J = 7.4 Hz, 1H), 7.19-7.07 (m, 3H), 4.48 (ddd, J = 44.0, 20.0, 7.9 Hz, 4H), 3.49 (d, J = 23.3 Hz, 2H), 3.11 (d, J = 6.6 Hz, 2H), 2.90 (s, 2H), 2.68-2.60 (m, 2H), 2.60-2.52 (m, 2H), 1.85 (s, 6H), 1.08-0.95 (m, 1H), 0.53-0.41 (m, 2H), 0.36-0.24 (m, 2H). | 406.2 |
| SC-34 | Cis-5-(cyclopropylmethyl)-7-(6-cyclopropylpyridin-3-yl)-2-(dimethylamino)-2-phenyl-5,7-diazaspiro[3.4]octan-6-one | 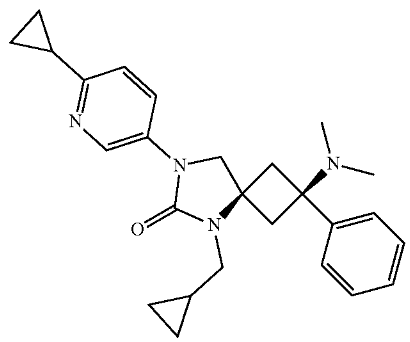 [SMILES: CN(C)[C@]1(c2ccccc2)C[C@@]2(CN(c3ccc(C4CC4)nc3)C(=O)N2CC2CC2)C1] | INT-14 | 5-Bromo-2-cyclopropylpyridine (step 1); bromomethylcyclopropane (step 2) | SC-15 | ¹H NMR (600 MHz, DMSO-d₆) δ 8.26 (d, J = 2.6 Hz, 1H), 7.60 (dt, J = 8.5, 2.1 Hz, 1H), 7.42 (t, J = 7.6 Hz, 2H), 7.36-7.28 (m, 3H), 7.14 (d, J = 8.6 Hz, 1H), 3.36 (s, 2H), 3.25 (d, J = 6.7 Hz, 2H), 2.82-2.76 (m, 2H), 2.71-2.65 (m, 2H), 2.02-1.94 (m, 1H), 1.87 (s, 6H), 1.17-1.02 (m, 1H), 0.88-0.82 (m, 2H), 0.78 (dq, J = 6.8, 4.1, 3.6 Hz, 2H), 0.51 (dt, J = 8.3, 3.0 Hz, 2H), 0.39-0.31 (m, 2H). | 417.3 |
| SC-35 | Cis-7-(6-cyclopropyl-4-methylpyridin-3-yl)-5-(cyclopropylmethyl)-2-(dimethylamino)-2-phenyl-5,7-diazaspiro[3.4]octan-6-one | 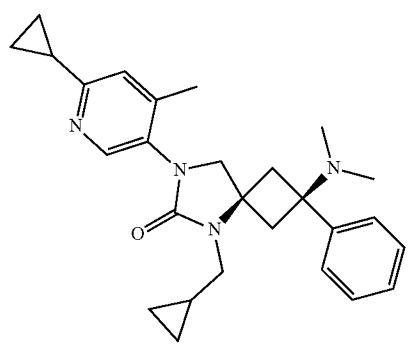 [SMILES: Cc1cc(C2CC2)ncc1N1C[C@]2(C[C@](c3ccccc3)(N(C)C)C2)N(CC2CC2)C1=O] | INT-14 | 5-bromo-2-cyclopropyl-4-methylpyridine (step 1), bromomethylcyclopropane (step 2) | SC-12 for step 1; SC-15 (step 2) for step 2 | ¹H NMR (600 MHz, DMSO-d₆) δ 8.05 (s, 1H), 7.37 (t, J = 7.6 Hz, 2H), 7.33-7.26 (m, 2H), 7.29-7.24 (m, 1H), 7.10 (d, J = 1.1 Hz, 1H), 3.20 (d, J = 6.5 Hz, 2H), 3.17 (s, 2H), 2.82-2.76 (m, 2H), 2.69-2.63 (m, 2H), 2.05 (s, 3H), 1.99 (tt, J = 8.2, 4.8 Hz, 1H), 1.87 (s, 6H), 1.08 (ddt, J = 9.7, 8.0, 3.2 Hz, 1H), 0.87 (dt, J = 8.1, 3.0 Hz, 2H), 0.83-0.80 (m, 2H), 0.54-0.47 (m, 2H), 0.37-0.30 (m, 2H). | 431.3 |

-continued

| Example | Chemical name | Chemical structure | Reactant I | Reactant II | in analogy to method | ¹H NMR data | m/z (M + H)⁺ |
|---|---|---|---|---|---|---|---|
| SC-36 | Cis-7-(6-cyclopropyl-4-methylpyridin-3-yl)-2-(dimethylamino)-5-((3-fluorooxetan-3-yl)methyl)-2-phenyl-5,7-diazaspiro[3.4]octan-6-one | 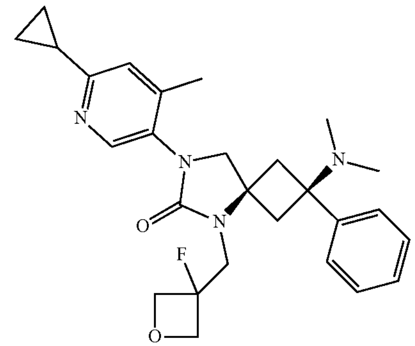 [SMILES: Cc1cc(C2CC2)ncc1N1C[C@]2(C[C@](c3ccccc3)(N(C)C)C2)N(CC2(F)COC2)C1=O] | INT-14 | 5-bromo-2-cyclopropyl-4-methylpyridine (step 1), (3-fluorooxetan-3-yl)methyl 4-methylbenzenesulfonate (step 2) | SC-12 for step 1; SC-15 (step 2) for step 2 | ¹H NMR (600 MHz, DMSO-d₆) δ 8.07 (s, 1H), 7.37 (t, J = 7.6 Hz, 2H), 7.33-7.22 (m, 3H), 7.12 (s, 1H), 4.82-4.70 (m, 2H), 4.63 (dd, J = 20.6, 8.0 Hz, 2H), 3.85 (d, J = 22.0 Hz, 2H), 3.19 (s, 2H), 2.84-2.74 (m, 2H), 2.64-2.55 (m, 2H), 2.05 (s, 3H), 2.00 (tt, J = 8.2, 4.8 Hz, 1H), 1.85 (s, 6H), 0.92-0.86 (m, 2H), 0.84-0.79 (m, 2H). | 465.3 |
| SC-38 | Cis-2-(dimethylamino)-2-phenyl-7-(2-pyridin-4-yl)pyrimidin-5-yl)-5,7-diazaspiro[3.4]octan-6-one | 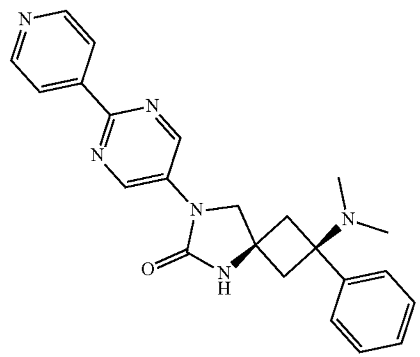 [SMILES: CN(C)[C@]1(c2ccccc2)C[C@@]2(CN(c3cnc(-c4ccncc4)nc3)C(=O)N2)C1] | INT-14 | 5-bromo-2-(4-pyridyl)pyrimidine | SC-12 | ¹H NMR (600 MHz, DMSO-d₆ + TFA); δ 10.59 (s, 1H), 9.01-8.96 (m, 3H), 8.72 (d, J = 6.9 Hz, 2H), 8.08 (s, 1H), 7.69 (dd, J = 6.6, 2.9 Hz, 2H), 7.57 (dd, J = 5.0, 1.8 Hz, 3H), 3.30-3.24 (m, 2H), 3.10-3.05 (m, 2H), 2.52 (s, 6H). | 401.2 |

-continued

| Example | Chemical name | Chemical structure | Reactant I | Reactant II | in analogy to method | ¹H NMR data | m/z (M + H)⁺ |
|---|---|---|---|---|---|---|---|
| SC-39 | Cis-5-(cyclopropylmethyl)-2-(dimethylamino)-2-phenyl-7-[5-(trifluoromethyl)pyridin-3-yl]-5,7-diazaspiro[3.4]octan-6-one | 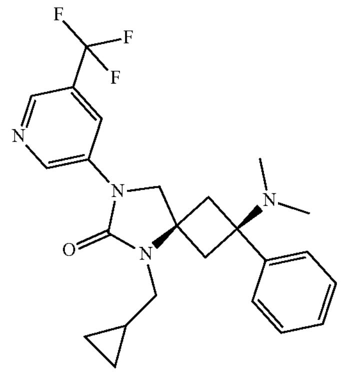 [SMILES: CN(C)[C@]1(c2ccccc2)C[C@@]2(CN(c3cncc(C(F)(F)F)c3)C(=O)N2CC2CC2)C1] | INT-43 | 3-Bromo-5-trifluoromethylpyridine | SC-12 | ¹H NMR (600 MHz, DMSO-d₆) δ 8.67 (d, J = 2.5 Hz, 1H), 8.52 (d, J = 2.0 Hz, 1H), 8.25 (t, J = 2.3 Hz, 1H), 7.43 (t, J = 7.5 Hz, 2H), 7.34 (t, J = 7.3 Hz, 1H), 7.32-7.27 (m, 2H), 3.59 (s, 2H), 3.32 (d, J = 6.7 Hz, 2H), 2.85-2.80 (m, 2H), 2.77-2.71 (m, 2H), 1.88 (s, 6H), 1.18-1.09 (m, 1H), 0.53 (dt, J = 8.2, 3.0 Hz, 2H), 0.41-0.34 (m, 2H). | 445.2 |
| SC-40 | Cis-5-[5-(cyclopropylmethyl)-2-(dimethylamino)-6-oxo-2-phenyl-5,7-diazaspiro[3.4]octan-7-yl]-3-(trifluoromethyl)pyridine-2-carbonitrile | 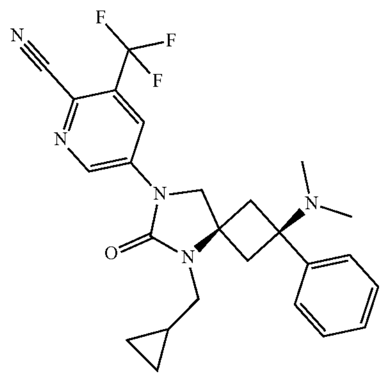 [SMILES: CN(C)[C@]1(c2ccccc2)C[C@@]2(CN(c3cnc(C#N)c(C(F)(F)F)c3)C(=O)N2CC2CC2)C1] | INT-43 | 5-Bromo-2-cyano-3-(trifluoromethyl)pyridine | SC-12 | ¹H NMR (600 MHz, DMSO-d₆): δ 8.81 (d, J = 2.4 Hz, 1H), 8.43 (d, J = 2.5 Hz, 1H), 7.43 (d, J = 7.6 Hz, 2H), 7.37-7.31 (m, 1H), 7.30-7.25 (m, 2H), 3.71 (s, 2H), 3.37 (d, J = 6.7 Hz, 2H), 2.83 (d, J = 13.7 Hz, 2H), 2.78 (d, J = 13.5 Hz, 2H), 1.88 (s, 6H), 1.20-1.11 (m, 1H), 0.54 (dt, J = 8.2, 3.0 Hz, 2H), 0.43-0.33 (m, 2H). | 470.2 |
| SC-42 | Cis-5-(cyclopropylmethyl)-2-(dimethylamino)-2-(3-fluorophenyl)-7-[(1-hydroxycyclobutyl)methyl]-5,7-diazaspiro[3.4]octan-6-one | 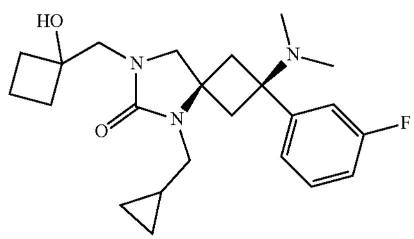 [SMILES: CN(C)[C@]1(c2cccc(F)c2)C[C@@]2(CN(CC3(O)CCC3)C(=O)N2CC2CC2)C1] | INT-45 | [1-[tert-butyl(dimethyl)silyl]oxycyclobutyl]methyl 4-methylbenzenesulfonate | SC-37 | ¹H NMR (600 MHz, DMSO-d₆): δ 7.46 (q, J = 7.3 Hz, 1H), 7.17 (s, 3H), 3.11 (d, J = 6.5 Hz, 2H), 3.02 (s, 2H), 2.99 (s, 2H), 2.77-2.57 (m, 4H), 2.01-1.86 (br s, 6H), 1.86-1.74 (m, 4H), 1.59-1.51 (m, 1H), 1.42-1.32 (m, 1H), 1.06-0.98 (m, 1H), 0.50-0.43 (m, 2H), 0.33-0.26 (m, 2H). | 402.3 |

| Example | Chemical name | Chemical structure | Reactant I | Reactant II | in analogy to method | ¹H NMR data | m/z (M + H)⁺ |
|---|---|---|---|---|---|---|---|
| SC-43 | Cis-5-(cyclopropylmethyl)-2-(dimethylamino)-2-phenyl-7-(2-pyridin-4-ylpyrimidin-5-yl)-5,7-diazaspiro[3.4]octan-6-one | 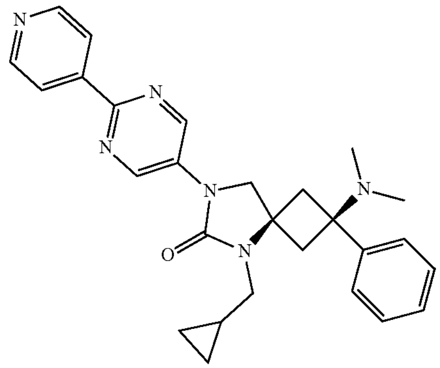 [SMILES: CN(C)[C@]1(c2ccccc2)C[C@@]2(CN(c3cnc(-c4ccncc4)nc3)C(=O)N2CC2CC2)C1] | SC-38 | bromomethylcyclopropane | SC-15 (step 2) | ¹H NMR (600 MHz, DMSO-d₆) δ 8.94 (s, 2H), 8.72-8.68 (m, 2H), 8.17-8.13 (m, 2H), 7.44 (t, J = 7.5 Hz, 2H), 7.35 (t, J = 7.4 Hz, 1H), 7.31 (d, J = 7.5 Hz, 2H), 3.60 (s, 2H), 2.84 (d, J = 13.7 Hz, 2H), 2.76 (d, J = 13.6 Hz, 2H), 1.88 (s, 6H), 1.20-1.08 (m, 1H), 0.58-0.50 (m, 2H), 0.43-0.35 (m, 2H). One CH₂ signal overlaps with residual water peak (observed in HSQC: (3.3; 44.8)). | 455.3 |
| SC-45 | Cis-3-[5-(cyclopropylmethyl)-2-(dimethylamino)-6-oxo-2-phenyl-5,7-diazaspiro[3.4]octan-7-yl]propanenitrile | 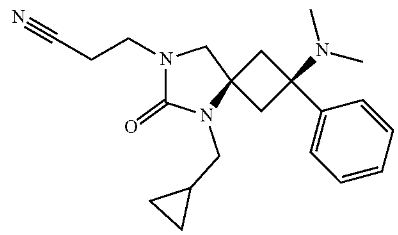 [SMILES: CN(C)[C@]1(c2ccccc2)C[C@@]2(CN(CCC#N)C(=O)N2CC2CC2)C1] | INT43 | 3-Bromopropionitrile | SC-44 | ¹H NMR (600 MHz, DMSO-d₆) δ 7.40 (t, J = 7.6 Hz, 2H), 7.34-7.27 (m, 3H), 3.21 (t, J = 6.6 Hz, 2H), 3.12 (d, 7 = 6.6 Hz, 2H), 2.92 (s, 2H), 2.67 (d, J = 13.2 Hz, 2H), 2.60 (d, J = 13.1 Hz, 2H), 2.56 (t, J = 6.5 Hz, 2H), 1.84 (s, 6H), 1.06-0.99 (m, 1H), 0.52-0.44 (m, 2H), 0.34-0.27 (m, 2H). | 353.2 |

| Example | Chemical name | Chemical structure | Reactant I | Reactant II | in analogy to method | $^1$H NMR data | m/z (M + H)$^+$ |
|---|---|---|---|---|---|---|---|
| SC-46 | Cis-5-(cyclopropylmethyl)-2-(dimethylamino)-7-[(1-hydroxycyclobutyl)methyl]-2-phenyl-5,7-diazaspiro[3.4]octan-6-one | 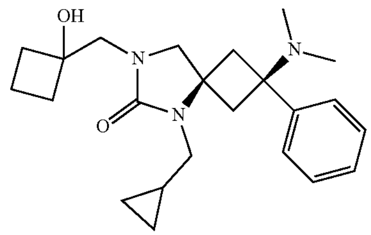 [SMILES: CN(C)[C@]1(c2ccccc2)C[C@@]2(CN(CC3(O)CCC3)C(=O)N2CC2CC2)C1] | INT-43 | [1-[tert-butyl(dimethyl)silyl]oxycyclobutyl]methyl 4-methylbenzenesulfonate | SC-37 | $^1$H NMR (600 MHz, DMSO-d$_6$): δ 7.39 (t, J = 7.6 Hz, 2H), 7.32-7.25 (m, 3H), 3.10 (d, J = 6.6 Hz, 2H), 3.01 (s, 2H), 2.98 (s, 2H), 2.65-2.59 (m, 2H), 2.59-2.53 (m, 2H), 1.86-1.80 (m, 8H), 1.77 (qd, J = 9.4, 2.5 Hz, 2H), 1.59-1.52 (m, 1H), 1.36 (dp, J = 11.3, 8.9 Hz, 1H), 1.06-0.98 (m, 1H), 0.47 (dt, J = 10.1, 2.9 Hz, 2H), 0.33-0.26 (m, 2H). | 384.3 |
| SC-47 | Cis-5-(cyclopropylmethyl)-2-(dimethylamino)-7-(3-fluorophenyl)-2-[2-(oxetan-3-yl)ethyl]-5,7-diazaspiro[3.4]octan-6-one | 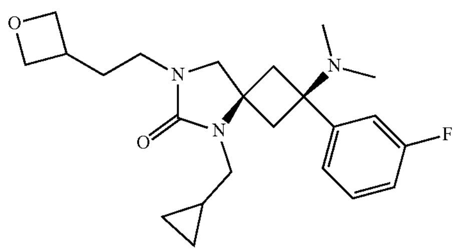 [SMILES: CN(C)[C@]1(c2cccc(F)c2)C[C@@]2(CN(CCC3COC3)C(=O)N2CC2CC2)C1] | INT-45 | 2-(oxetan-3-yl)ethyl 4-methylbenzenesulfonate | SC-44 | $^1$H NMR (600 MHz, DMSO-d$_6$): δ 7.49-7.41 (m, 1H), 7.18-7.11 (m, 3H), 4.54 (dd, J = 7.8, 5.8 Hz, 2H), 4.17 (t, J = 6.1 Hz, 2H), 3.08 (d, J = 6.5 Hz, 2H), 2.89 (t, J = 6.9 Hz, 2H), 2.82 (s, 2H), 2.85-2.76 (m, 1H), 2.67-2.61 (m, 2H), 2.59-2.53 (m, 2H), 1.85 (s, 6H), 1.62 (q, J = 7.2 Hz, 2H), 1.04-0.97 (m, 1H), 0.47 (dt, J = 10.4, 3.0 Hz, 2H), 0.31-0.25 (m, 2H). | 402.3 |

Names and structures of exemplified compounds:

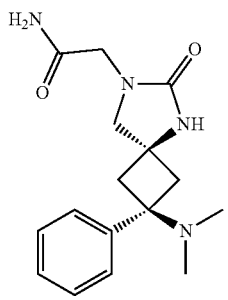

cis-2-(2-(dimethylamino)-6-
oxo-2-phenyl-5,7-diazaspiro
[3.4]octan-7-yl)acetamide

SC-1

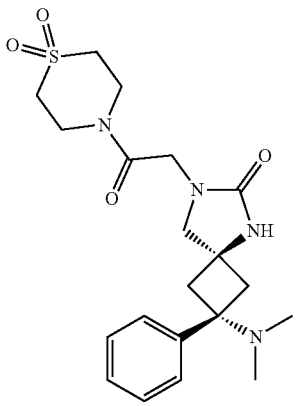

trans-2-(dimethylamino)-7-
(2-(1,1-dioxidothiomorpholino)-
2-oxoethyl)-2-phenyl-5,7-
diazaspiro[3.4]octan-6-one

SC-4

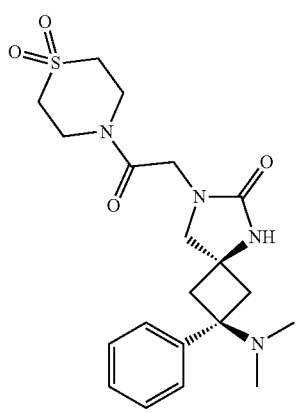

cis-2-(dimethylamino)-7-(2-(1,1-
dioxidothiomorpholino)-2-
oxoethyl)-2-phenyl-5,7-
diazaspiro[3.4]octan-6-one

SC-2

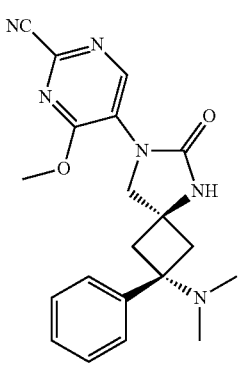

trans-5-(2-(dimethylamino)-6-
oxo-2-phenyl-5,7-
diazaspiro[3.4]octan-7-yl)-4-
methoxypyrimidine-2-
carbonitrile

SC-5

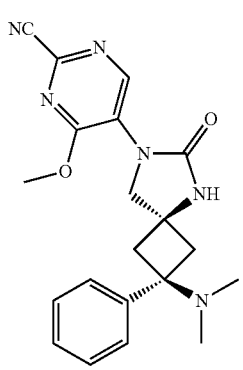

cis-5-(2-(dimethylamino)-6-
oxo-2-phenyl-5,7-diazaspiro
[3.4]octan-7-yl)-4-
methoxypyrimidine-2-
carbonitrile

SC-3

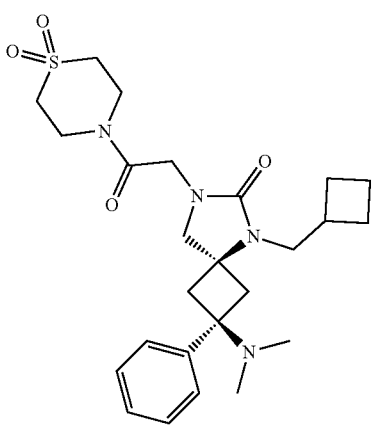

cis-5-(cyclobutylmethyl)-2-(dimethylamino)-7-
(2-(1,1-dioxidothiomorpholino)-2-oxoethyl)-2-
phenyl-5,7-diazaspiro[3.4]octan-6-one

SC-6

SC-7

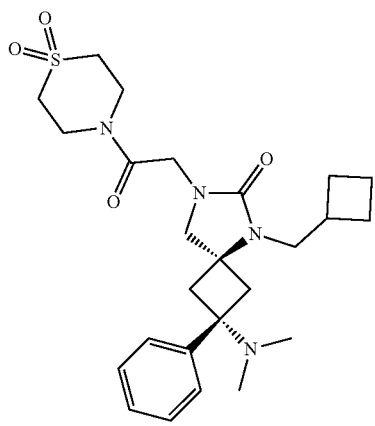

trans-5-(cyclobutylmethyl)-2-
(dimethylamino)-7-(2-(1,1-
dioxidothiomorpholino)-2-oxoethyl)-
2-phenyl-5,7-diazaspiro[3.4]octan-6-one

SC-10

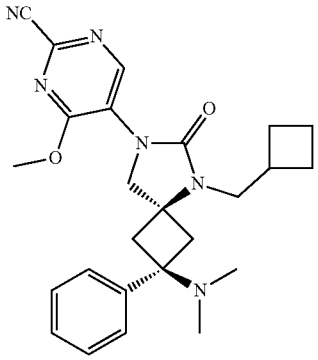

cis-5-(5-(cyclobutylmethyl)-2-
(dimethylamino)-6-oxo-2-
phenyl-5,7-diazaspiro[3.4]octan-7-yl)-4-
methoxypyrimidine-2-carbonitrile

SC-8

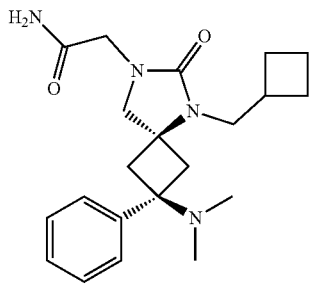

cis-2-(5-(cyclobutylmethyl)-2-
(dimethylamino)-6-oxo-2-
phenyl-5,7-diazaspiro[3.4]octan-
7-yl)acetamide

SC-11

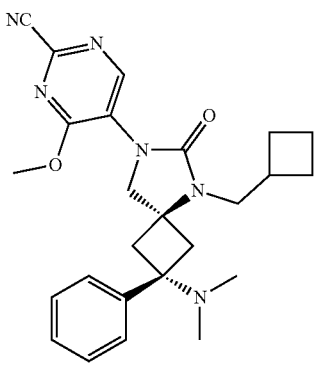

trans-5-(5-(cyclobutylmethyl)-2-
(dimethylamino)-6-oxo-2-
phenyl-5,7-diazaspiro[3.4]octan-7-yl)-4-
methoxypyrimidine-2-carbonitrile

SC-9

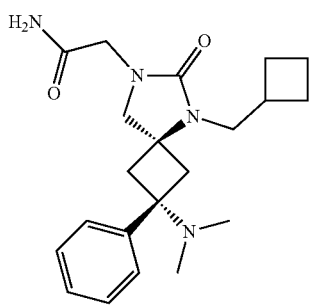

trans-2-(5-(cyclobutylmethyl)-2-
(dimethylamino)-6-oxo-2-
phenyl-5,7-diazaspiro[3.4]octan-
7-yl)acetamide

SC-12 cis-2-(dimethylamino)-7-(4-methyl-2-morpholin-
4-ylpyrimidin-5-yl)-2-phenyl-5,7-
diazaspiro[3.4]octan-6-one

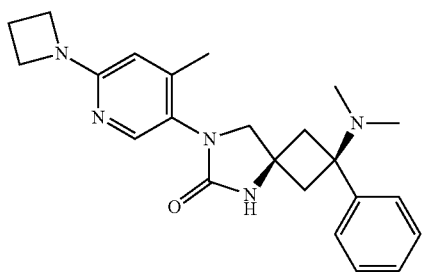

cis-7-(6-(azetidin-1-yl)-4-methylpyridin-3-yl)-2-(dimethylamino)-2-phenyl-5,7-diazaspiro[3.4]octan-6-one

SC-13

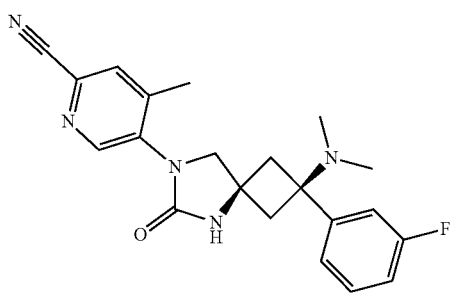

cis-5-(2-(dimethylamino)-2-(3-fluorophenyl)-6-oxo-5,7-diazaspiro[3.4]octan-7-yl)-4-methylpicolinonitrile

SC-14

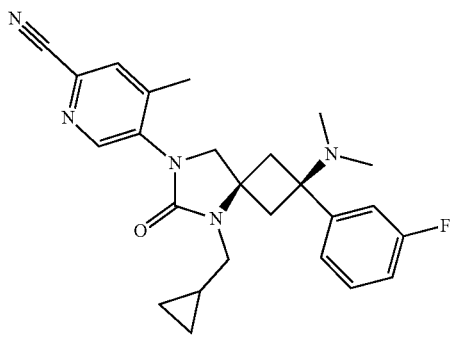

cis-5-(5-cyclopropylmethyl)-2-(dimethylamino)-2-(3-fluorophenyl)-6-oxo-5,7-diazaspiro[3.4]octan-7-yl)-4-methylpicolinonitrile

SC-15

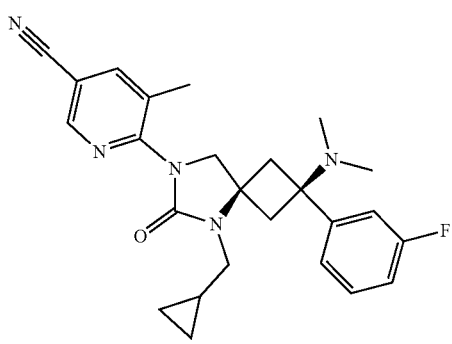

cis-6-(5-cyclopropylmethyl)-2-(dimethylamino)-2-(3-fluorophenyl)-6-oxo-5,7-diazaspiro[3.4]octan-7-yl)-5-methylnicotinonitrile

SC-16

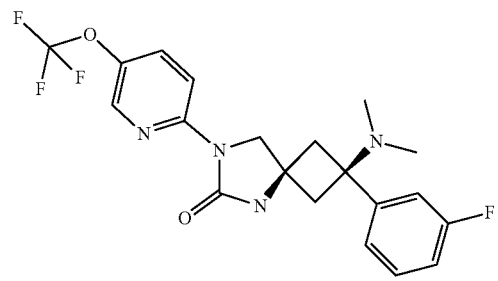

cis-2-(dimethylamino)-2-(3-fluorophenyl)-7-(5-(trifluoromethoxy)pyridin-2-yl)-5,7-diazaspiro[3.4]octan-6-one

SC-17

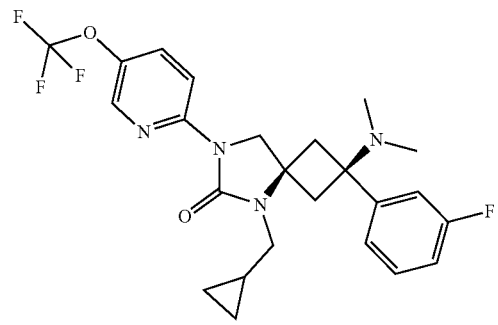

cis-5-(cyclopropylmethyl)-2-(dimethylamino)-2-(3-fluorophenyl)-7-(5-(trifluoromethoxy)pyridin-2-yl)-5,7-diazaspiro[3.4]octan-6-one

SC-18

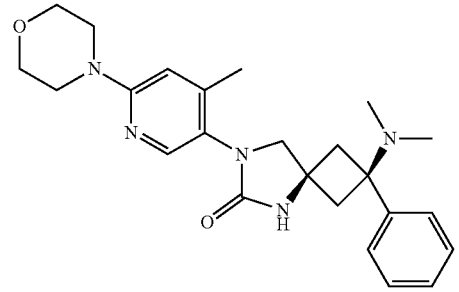

cis-2-(dimethylamino)-7-(4-methyl-6-morpholinopyridin-3-yl)-2-phenyl-5,7-diazaspiro[3.4]octan-6-one

SC-19

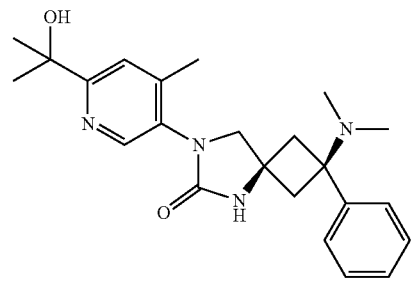

cis-2-(dimethylamino)-7-(6-(2-hydroxypropan-2-yl)-4-methylpyridin-3-yl)-2-phenyl-5,7-diazaspiro[3.4]octan-6-one

SC-20

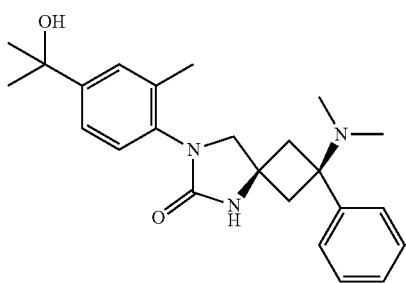

cis-2-(dimethylamino)-7-(4-(2-hydroxypropan-
2-yl)-2-methylphenyl)-2-phenyl-5,7-diazaspiro
[3.4]octan-6-one

SC-21

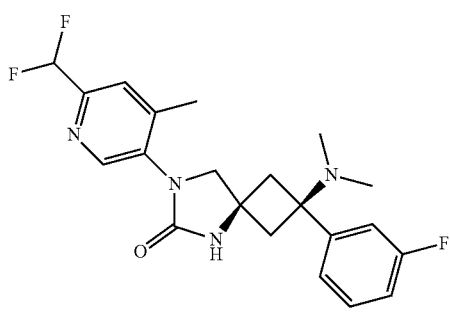

cis-7-(6-(difluoromethyl)-4-methylpyridin-3-yl)-2-
(dimethylamino)-2-(3-fluorophenyl)-5,7-diazaspiro
[3.4]octan-6-one

SC-22

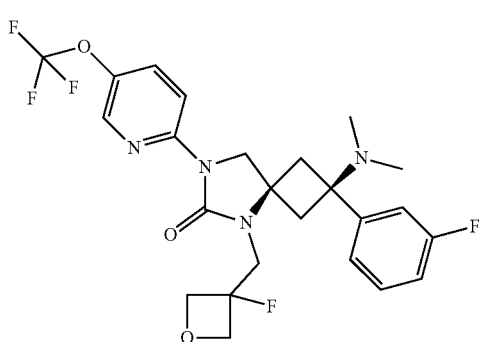

cis- -2-(dimethylamino)-5-((3-fluorooxetan-3-yl)methyl)-2-
(3-fluorophenyl)-7-(5-(trifluoromethoxy)pyridin-2-yl)-5,7-
diazaspiro[3.4]octan-6-one

SC-23

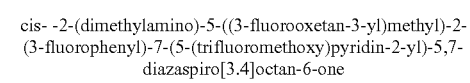
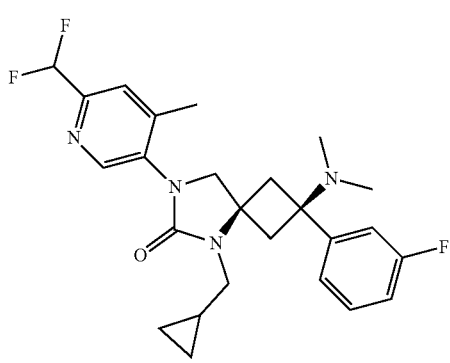

cis-5-(cyclopropylmethyl)-7-(6-(difluoromethyl)-4-
methylpyridin-3-yl)-2-(dimethylamino)-2-
(3-fluorophenyl)-5,7-
diazaspiro[3.4]octan-6-one

SC-24

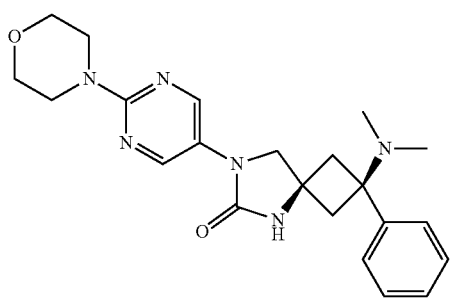

cis-2-(dimethylamino)-7-(2-morpholinopyrimidin-
5-yl)-2-phenyl-5,7-diazaspiro[3.4]octan-6-one

SC-25

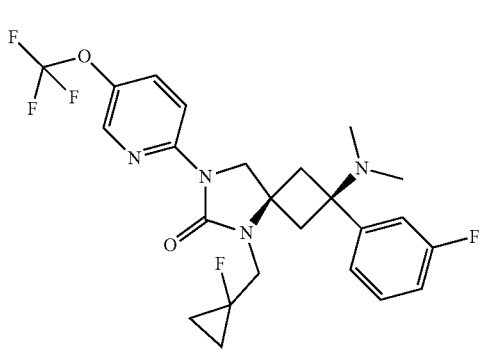

cis-2-(dimethylamino)-5-((1-fluorocyclopropyl)methyl)-2-
(3-fluorophenyl)-7-(5-(trifluoromethoxy)pyridin-2-yl)-5,7-
diazaspiro[3.4]octan-6-one

SC-26 cis-2-(dimethylamino)-2-(3-fluorophenyl)-5-((1-
hydroxycyclobutyl)methyl)-7-(5-(trifluoromethoxy)
pyridin-2-yl)-5,7-
diazaspiro[3.4]octan-6-one

SC-27

SC-28

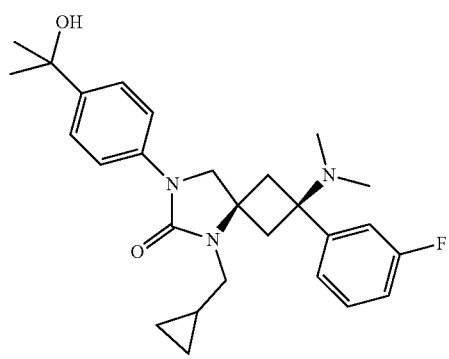

cis-5-(cyclopropylmethyl)-2-(dimethylamino)-
2-(3-fluorophenyl)-7-(4-(2-hydroxypropan-2-
yl)phenyl)-5,7-diazaspiro[3.4]octan-6-one

SC-29

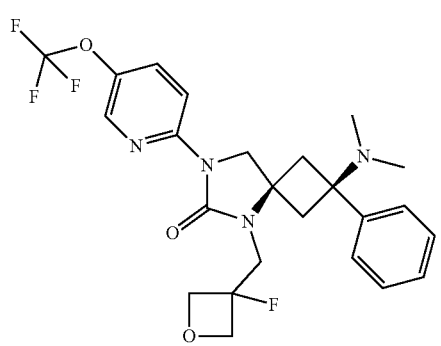

cis-2-(dimethylamino)-5-((3-fluorooxetan-3-yl)methyl)-
2-phenyl-7-(5-(trifluoromethoxy)pyridin-2-yl)-
5,7-diazaspiro[3.4]octan-6-one

SC-30

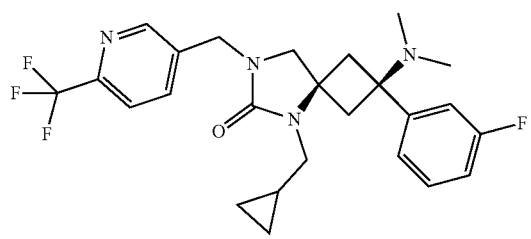

cis-5-(cyclopropylmethyl)-2-(dimethylamino)-2-(3-fluorophenyl)-
7-((6-(trifluoromethyl)pyridin-3-yl)methyl)-5,7-diazaspiro[3.4]
octan-6-one

SC-31

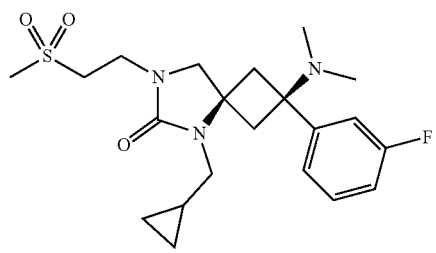

cis-5-(cyclopropylmethyl)-2-(dimethylamino)-2-
(3-fluorophenyl)-7-(2-(methylsulfonyl)ethyl)-
5,7-diazaspiro[3.4]octan-6-one

SC-32

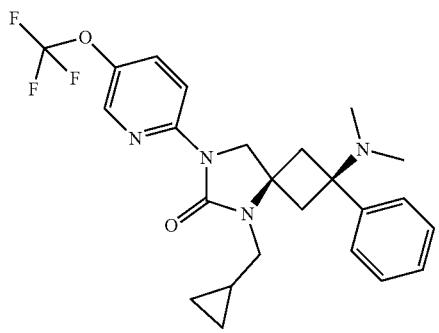

cis-5-(cyclopropylmethyl)-2-(dimethylamino)-
2-phenyl-7-(5-(trifluoromethoxy)pyridin-2-yl)-
5,7-diazaspiro[3.4]octan-6-one

SC-33

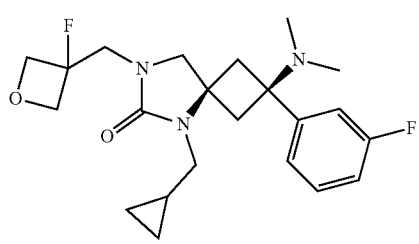

cis-5-(cyclopropylmethyl)-2-(dimethylamino)-
7-((3-fluorooxetan-3-yl)methyl)-2-(3-
fluorophenyl)-5,7-diazaspiro[3.4]octan-6-one

SC-34

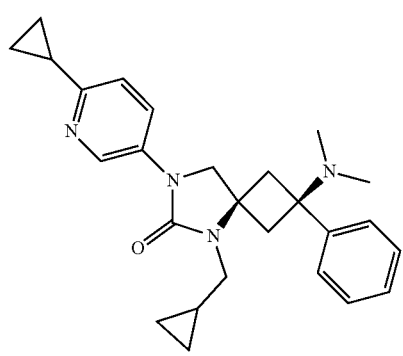

cis-5-(cyclopropylmethyl)-7-(6-cyclopropylpyridin-
3-yl)-2-(dimethylamino)-2-phenyl-5,7-
diazaspiro[3.4]octan-6-one

SC-35

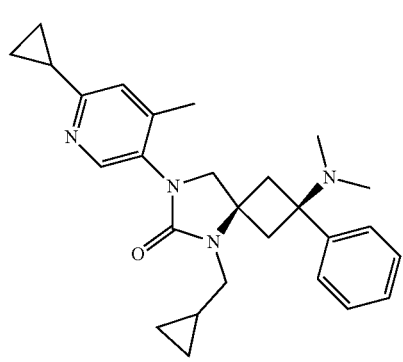

cis-7-(6-cyclopropyl-4-methylpyridin-3-yl)-5-
(cyclopropylmethyl)-2-(dimethylamino)-
2-phenyl-5,7-diazaspiro[3.4]octan-6-one

SC-36

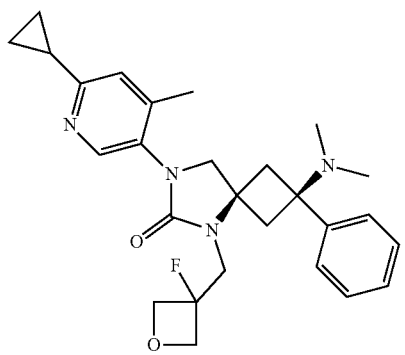

cis-7-(6-cyclopropyl-4-methylpyridin-3-yl)-2-
(dimethylamino)-5-((3-fluorooxetan-3-yl)methyl)-
2-phenyl-5,7-diazaspiro[3.4]octan-6-one

SC-37

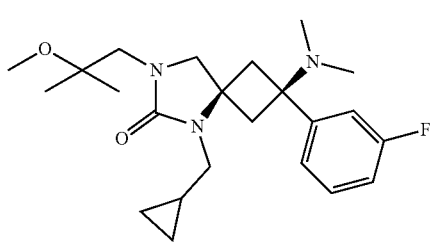

cis-5-(cyclopropylmethyl)-2-(dimethylamino)-2-
(3-fluorophenyl)-7-(2-methoxy-2-methylpropyl)-5,7-
diazaspiro[3.4]octan-6-one

SC-38

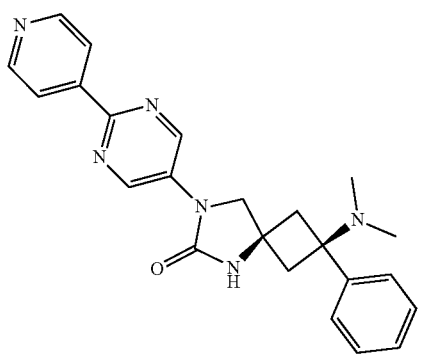

cis-2-(dimethylamino)-2-phenyl-7-(2-pyridin-
4-ylpyrimidin-5-yl)-5,7-diazaspiro[3.4]octan-6-one

SC-39

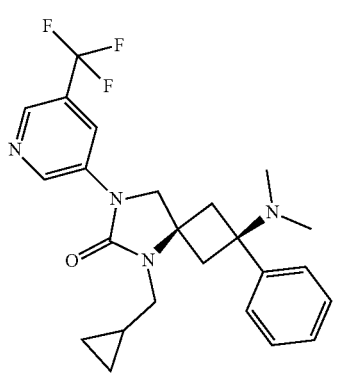

cis-5-(cyclopropylmethyl)-2-
(dimethylamino)-2-phenyl-7-
[5-(trifluoromethyl)pyridin-3-yl]-5,7-
diazaspiro[3.4]octan-6-one

SC-40

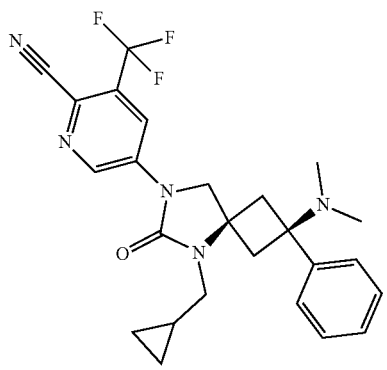

cis-5-[5-(cyclopropylmethyl)-2-(dimethylamino)-
6-oxo-2-phenyl-5,7-diazaspiro[3.4]octan-7-
yl]-3-(trifluoromethyl)pyridine-
2-carbonitrile

SC-41

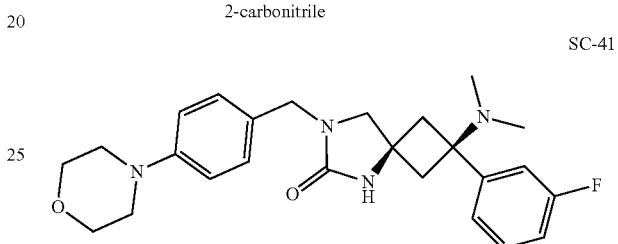
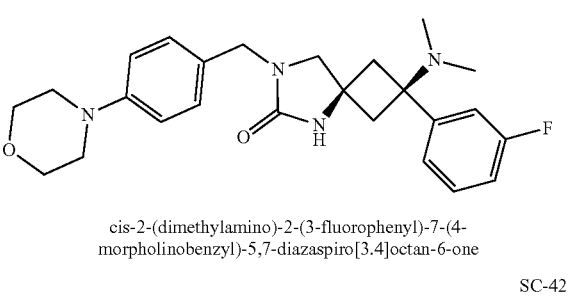

cis-2-(dimethylamino)-2-(3-fluorophenyl)-7-(4-
morpholinobenzyl)-5,7-diazaspiro[3.4]octan-6-one

SC-42

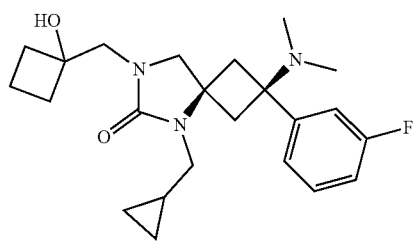

cis-5-(cyclopropylmethyl)-2-(dimethylamino)-2-
(3-fluorophenyl)-7-[(1-hydroxycyclobutyl)
methyl]-5,7-diazaspiro[3.4]octan-6-one

SC-43

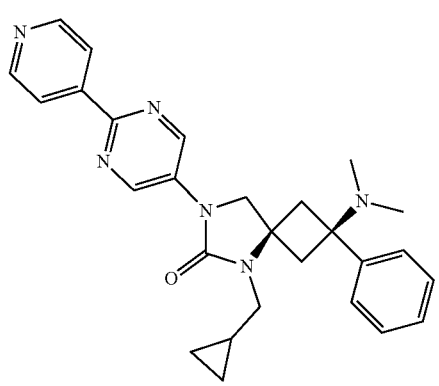

cis-5-(cyclopropylmethyl)-2-(dimethylamino)-2-
phenyl-7-(2-pyridin-4-ylpyrimidin-5-yl)-
5,7-diazaspiro[3.4]octan-6-one -continued

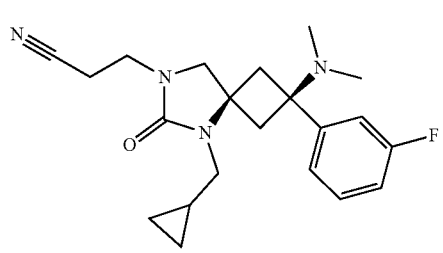

cis-3-(5-(cyclopropylmethyl)-2-(dimethylamino)-2-(3-fluorophenyl)-6-oxo-5,7-diazaspiro[3.4]octan-7-yl)propanenitrile

SC-44

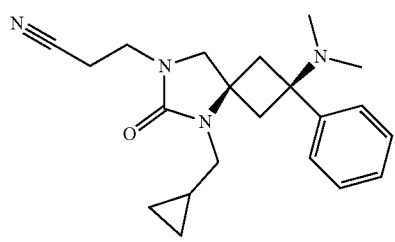

cis-3-[5-(cyclopropylmethyl)-2-(dimethylamino)-6-oxo-2-phenyl-5,7-diazaspiro[3.4]octan-7-yl]propanenitrile

SC-45

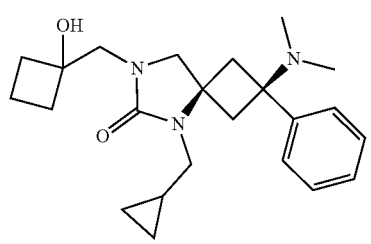

cis-5-(cyclopropylmethyl)-2-(dimethylamino)-7-[(1-hydroxycyclobutyl)methyl]-2-phenyl-5,7-diazaspiro[3.4]octan-6-one

SC-46

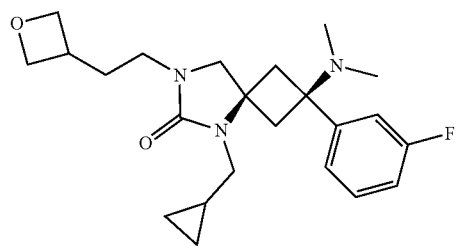

cis-5-(cyclopropylmethyl)-2-(dimethylamino)-2-(3-fluorophenyl)-7-[2-(oxetan-3-yl)ethyl]-5,7-diazaspiro[3,4]octan-6-one

SC-47

Pharmacological Investigations

Functional investigation on the human mu-opioid receptor (hMOP), human kappa-opioid receptor (hKOP), human delta-opioid receptor (hDOP), and human nociceptin/orphanin FQ peptide receptor (hNOP)

Human Mu-Opioidpeptide (hMOP) Receptor Binding Assay

The hMOP receptor binding assay was performed as homogeneous SPA-assay (scintillation proximity assay) using the assay buffer 50 mM TRIS-HCl (pH 7.4) supplemented with 0.052 mg/ml bovine serum albumin (Sigma-Aldrich Co. St. Louis, Mo.). The final assay volume (250 µl/well) included 1 nM of [N-allyl-2.3-$^3$H]naloxone as ligand (PerkinElmer Life Sciences. Inc. Boston, Mass. USA) and either test compound in dilution series or 25 µM unlabelled naloxone for determination of unspecific binding. The test compound was diluted with 25% DMSO in $H_2O$ to yield a final 0.5% DMSO concentration which also served as a respective vehicle control. The assay was started by adding wheat germ agglutinin coated SPA beads (GE Healthcare UK Ltd. Buckinghamshire. UK) which had been preloaded with hMOP receptor membranes (PerkinElmer Life Sciences. Inc. Boston, Mass. USA). After incubation for 90 minutes at RT and centrifugation for 20 minutes at 500 rpm the signal rate was measured by means of a 1450 Microbeta Trilux ß-counter (PerkinElmer Life Sciences/Wallac. Turku. Finland). Half-maximal inhibitory concentration (IC50) values reflecting 50% displacement of [$^3$H]naloxone-specific receptor binding were calculated by nonlinear regression analysis and Ki values were calculated by using the Cheng-Prusoff equation. (Cheng and Prusoff. 1973).

Human Kappa-Opioidpeptide (hKOP) Receptor Binding Assay

The hKOP receptor binding assay is run as homogeneous SPA-assay (scintillation proximity assay) using the assay buffer 50 mM TRIS-HCl (pH 7.4) supplemented with 0.076 mg BSA/ml. The final assay volume of 250 µl per well includes 2 nM of [$^3$H]U69,593 as ligand, and either test compound in dilution series or 100 µM unlabelled naloxone for determination of unspecific binding. The test compound is diluted with 25% DMSO in $H_2O$ to yield a final 0.5% DMSO concentration which serves as respective vehicle control, as well. The assays are started by the addition of wheat germ agglutinin coated SPA beads (1 mg SPA beads/250 µl final assay volume per well) which has been preloaded for 15 minutes at room temperature with hKOP receptor membranes (14.8 µg/250 µl final assay volume per well). After short mixing on a mini-shaker, the microtiter plates are covered with a lid and the assay plates are incubated for 90 minutes at room temperature. After this incubation, the microtiter plates are sealed with a topseal and centrifuged for 20 minutes at 500 rpm. The signal rate is measured after a short delay of 5 minutes by means of a 1450 Microbeta Trilux ß-counter (PerkinElmer Life Sciences/Wallac, Turku, Finland). Half-maximal inhibitory concentration (IC50) values reflecting 50% displacement of [$^3$H]U69.593-specific receptor binding are calculated by nonlinear regression analysis and Ki values are calculated by using the Cheng-Prusoff equation, (Cheng and Prusoff, 1973).

Human Delta-Opioidpeptide (hDOP) Receptor Binding Assay

The hDOP receptor binding assay is performed as homogeneous SPA-assay using the assay buffer 50 mM TRIS-HCl, 5 mM $MgCl_2$ (pH 7.4). The final assay volume (250 µl/well) includes 1 nM of [Tyrosyl-3,5-$^3$H]2-D-Ala-deltorphin II as ligand, and either test compound in dilution series or 10 µM unlabelled naloxone for determination of unspecific binding. The test compound is diluted with 25% DMSO in $H_2O$ to yield a final 0.5% DMSO concentration which serves as respective vehicle control, as well. The assays are started by the addition of wheat germ agglutinin coated SPA beads (1 mg SPA beads/250 µl final assay volume per well) which has been preloaded for 15 minutes at room temperature with hDOP receptor membranes (15.2 µg/250 µl final assay volume per well). After short mixing on a mini-shaker, the microtiter plates are covered with a lid and the assay plates are incubated for 120 minutes at room temperature and centrifuged for 20 minutes at 500 rpm. The signal rate is measured by means of a 1450 Microbeta Trilux ß-counter (PerkinElmer Life Sciences/Wallac, Turku, Finland). Half-maximal inhibitory concentration (IC50) values reflecting 50% displacement of [Tyrosyl-3,5-$^3$H]2-D-Ala-deltorphin II-specific receptor binding are calculated by nonlinear regression analysis and Ki values are calculated by using the Cheng-Prusoff equation, (Cheng and Prusoff, 1973).

Human Nociceptin/Orphanin FQ Peptide (hNOP) Receptor Binding Assay

The hNOP receptor binding assay was performed as homogeneous SPA-assay (scintillation proximity assay) using the assay buffer 50 mM TRIS-HCl, 10 mM $MgCl_2$, 1 mM EDTA (pH 7.4). The final assay volume (250 µl/well) included 0.5 nM of [leucyl-$^3$H]nociceptin as ligand (PerkinElmer Life Sciences. Inc. Boston, Mass. USA) and either test compound in dilution series or 1 µM unlabelled nociceptin for determination of unspecific binding. The test compound was diluted with 25% DMSO in $H_2O$ to yield a final 0.5% DMSO concentration which also served as a respective vehicle control. The assay was started by adding wheat germ agglutinin coated SPA beads (GE Healthcare UK Ltd. Buckinghamshire. UK) which had been preloaded with hNOP receptor membranes (PerkinElmer Life Sciences. Inc. Boston, Mass. USA). After incubation for 60 minutes at RT and centrifugation for 20 minutes at 500 rpm the signal rate was measured by means of a 1450 Microbeta Trilux ß-counter (PerkinElmer Life Sciences/Wallac. Turku. Finland). Half-maximal inhibitory concentration (IC50) values reflecting 50% displacement of [$^3$H]nociceptin-specific receptor binding were calculated by nonlinear regression analysis and Ki values were calculated by using the Cheng-Prusoff equation. (Cheng and Prusoff. 1973).

| Example | hNOP Ki [nM] or % inhibition at 1 µM | hMOP Ki [nM] or % inhibition at 1 µM |
| --- | --- | --- |
| SC-1 | 200 | 19% |
| SC-2 | 850 | 12% |
| SC-3 | 370 | 3605 |
| SC-4 | 860 | 15 |
| SC-5 | 800 | 99 |
| SC-6 | 1 | 285 |
| SC-7 | 230 | 2 |
| SC-8 | 3 | 100 |
| SC-9 | 380 | 48 |
| SC-10 | 2 | 157 |
| SC-11 | 99 | 3 |
| SC-12 | 630 | 13% |
| SC-13 | 860 | 18% |
| SC-15 | 13 | 1330 |
| SC-16 | 31 | 1315 |
| SC-18 | 55 | 805 |
| SC-19 | 1810 | 5890 |
| SC-20 | 1165 | 5840 |
| SC-21 | 775 | 3580 |
| SC-22 | 380 | 11% |
| SC-23 | 25 | 545 |
| SC-24 | 23 | 1185 |
| SC-26 | 91 | 1015 |
| SC-27 | 12 | 335 |
| SC-28 | 46 | 78 |
| SC-29 | 16 | 65 |
| SC-31 | 15 | 150 |
| SC-32 | 36 | 100 |
| SC-33 | 23 | 115 |
| SC-34 | 17 | 50 |
| SC-35 | 19 | 185 |
| SC-36 | 10 | 330 |
| SC-37 | 37 | 44 |
| SC-39 | 5 | 48 |
| SC-40 | 6 | 102 |
| SC-41 | 21 | 465 |
| SC-42 | 21 | 125 |
| SC-43 | 31 | 83 |
| SC-44 | 15 | 110 |
| SC-45 | 25 | 37 |
| SC-46 | 29 | 48 |
| SC-47 | 9 | 44 |

Protocol for [$^{35}$S]GTPγS Functional NOP/MOP/KOP/DOP Assays

Cell membrane preparations of CHO-K1 cells transfected with the human MOP receptor (Art.-No. RBHOMM) or the human DOP receptor (Art.-No.RBHODM), and HEK293 cells transfected with the human NOP receptor (Art.-No.RBHORLM) or the human KOP receptor (Art.-No. 6110558) are available from PerkinElmer (Waltham, Mass.). Membranes from CHO-K1 cells transfected with the human nociceptin/orphanin FQ peptide (hNOP) receptor (Art.-No. 93-0264$C_2$, DiscoveRx Corporation, Freemont, Calif.) are also used. [$^{35}$S]GTPγS (Art.-No. NEG030H; Lot-No. #0112, #0913, #1113 calibrated to 46.25 TBq/mmol) is available from PerkinElmer (Waltham, Mass.).

The [$^{35}$S]GTPγS assays are carried out essentially as described by Gillen et al (2000). They are run as homogeneous scintillation proximity (SPA) assays in microtiter luminescence plates, where each well contains 1.5 mg of WGA-coated SPA-beads. To test the agonistic activity of test compounds on recombinant hNOP, hMOP, hDOP, and hKOP receptor expressing cell membranes from CHO-K1 or HEK293 cells, 10 or 5 µg membrane protein per assay are incubated with 0.4 nM [$^{35}$S]GTPγS and serial concentrations of receptor-specific agonists in buffer containing 20 mM HEPES pH 7.4, 100 mM NaCl, 10 mM MgCl2, 1 mM EDTA, 1 mM dithiothreitol, 1.28 mM $NaN_3$, and 10 µM GDP for 45 min at room temperature. The microtiter plates are then centrifuged for 10 min at 830 g to sediment the SPA beads. The microtiter plates are sealed and the bound radioactivity [cpm] is determined after a delay of 15 min by means of a 1450 Microbeta Trilux (PerkinElmer, Waltham, Mass.).

The unstimulated basal binding activity ($UBS_{obs}$ [cpm]) is determined from 12 unstimulated incubates and is set as 100% basal binding. For determination of the potency and the efficacy, the arithmetic mean of the observed total [$^{35}$S]GTPγS binding ($TB_{obs}$ [cpm]) of all incubates (duplicates) stimulated by the receptor-specific agonists (i.e. N/OFQ, SNC80, DAMGO, or U69,593) are transformed in percent total binding ($TB_{obs}$ [%]) relative to the basal binding activity (i.e. 100% binding). The potency ($EC_{50}$) of the respective agonist and its maximal achievable total [$^{35}$S]GTPγS binding ($TB_{calc}$ [%]) above its calculated basal binding ($UBS_{calc}$ [%]) are determined from its transformed data ($TB_{obs}$ [%]) by means of nonlinear regression analysis with XLfit for each individual concentration series. Then the difference between the calculated unstimulated [$^{35}$S]GTPγS binding ($UBS_{calc}$ [%]) and the maximal achievable total [$^{35}$S]GTPγS binding ($TB_{calc}$ [%]) by each tested agonist is determined (i.e. $Bl_{calc}$ [%]). This difference ($Bl_{calc}$ [%]) as a measure of the maximal achievable enhancement of [$^{35}$S]GTPγS binding by a given agonist is used to calculate the relative efficacy of test compounds versus the maximal achievable enhancement by a receptor-specific full agonist, e.g. N/OFQ ($Bl_{calc-N/OFQ}$ [%]) which is set as 100% relative efficacy for the hNOP receptor. Likewise, the percentage efficacies of test compounds at the hDOP, hMOP, or hKOP receptor are determined versus the calculated maximal enhancement of [$^{35}$S]GTPγS binding by the full agonists SNC80 ($Bl_{calc\text{-}SNC80}$ [%]), DAMGO ($Bl_{calc\text{-}DAMGO}$ [%]) and U69,593 ($Bl_{calc\text{-}U69,593}$ [%]) which are set as 100% relative efficacy at each receptor, respectively.

The invention claimed is:

1. A compound according to general formula (I)

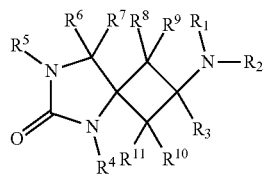

wherein
$R^1$ and $R^2$ independently of one another mean
—H;
—$C_1$-$C_6$-alkyl, linear or branched, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$;
a 3-12-membered cycloalkyl moiety, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$; wherein said 3-12-membered cycloalkyl moiety is optionally connected through —$C_1$-$C_6$-alkylene-, linear or branched, saturated or unsaturated, unsubstituted; or
a 3-12-membered heterocycloalkyl moiety, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$;
wherein said 3-12-membered heterocycloalkyl moiety is optionally connected through -$C_1$-$C_6$-alkylene-, linear or branched, saturated or unsaturated, unsubstituted;
or
$R^1$ and $R^2$ together with the nitrogen atom to which they are attached form a ring and mean —(CH$_2$)$_{3\text{-}6}$—; —(CH$_2$)$_2$—O—(CH$_2$)$_2$—; or —(CH$_2$)$_2$—NR$^A$—(CH$_2$)$_2$—, wherein R$^A$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;
$R^3$ means
—$C_1$-$C_6$-alkyl, linear or branched, saturated or unsaturated, unsubstituted, mono- or polysubstituted;
a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;
a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;
a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or
a 5-14-membered heteroaryl moiety, unsubstituted, mono- or polysubstituted; wherein said 5-14-membered heteroaryl moiety is optionally connected through -$C_1$-$C_6$-alkylene-, linear or branched, saturated or unsaturated, unsubstituted, mono- or polysubstituted;
$R^4$ means
—H;
—$C_1$-$C_6$-alkyl, linear or branched, saturated or unsaturated, unsubstituted, mono- or polysubstituted; wherein said -$C_1$-$C_6$-alkyl is optionally connected through —C(=O)—, —C(=O)O—, or —S(=O)$_2$—;
a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted; or wherein said 3-12-membered cycloalkyl moiety is optionally connected through —C(=O)—, —C(=O)O—, —C(=O)O—CH$_2$—, or —S(=O)$_2$—;
a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted; or wherein said 3-12-membered heterocycloalkyl moiety is optionally connected through —C(=O)—, —C(=O)O—, —C(=O)O—CH$_2$—, or —S(=O)$_2$—;
a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or wherein said 6-14-membered aryl moiety is optionally connected through —C(=O)—, —C(=O)O—, —C(=O)O—CH$_2$—, or —S(=O)$_2$—; or
a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted; or wherein said 5-14-membered heteroaryl moiety is optionally connected through —C(=O)—, —C(=O)O—, —C(=O)O—CH$_2$—, or —S(=O)$_2$—;
$R^5$ means
—H;
—$C_1$-$C_6$-alkyl, linear or branched, saturated or unsaturated, unsubstituted, mono- or polysubstituted; wherein said -$C_1$-$C_6$-alkyl is optionally connected through —C(=O)—, —C(=O)O—, or —S(=O)$_2$—;
a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted; or wherein said 3-12-membered cycloalkyl moiety is optionally connected through —C(=O)—, —C(=O)O—, —C(=O)O—$CH_2$—, or —S(=O)$_2$—;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted; or wherein said 3-12-membered heterocycloalkyl moiety is optionally connected through —C(=O)—, —C(=O)O—, —C(=O)O—$CH_2$—, or —S(=O)$_2$—;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or wherein said 6-14-membered aryl moiety is optionally connected through —C(=O)—, —C(=O)O—, —C(=O)O—$CH_2$—, or —S(=O)$_2$—; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted; or wherein said 5-14-membered heteroaryl moiety is optionally connected through —C(=O)—, —C(=O)O—, —C(=O)O—$CH_2$—, or —S(=O)$_2$—;

$R^6$, $R^7$, $R^8$, $R^9$, $R^{10}$, and $R^{11}$ independently of one another mean —H, —F, —Cl, —Br, —I, —OH, or -$C_1$-$C_6$-alkyl, linear or branched, saturated or unsaturated, unsubstituted, mono- or polysubstituted;

or $R^6$ and $R^7$ together mean =O;

wherein "mono- or polysubstituted" means that one or more hydrogen atoms are replaced by substituents independently of one another selected from the group consisting of —F, —Cl, —Br, —I, —CN, —$R^{12}$, —C(=O)$R^{12}$, —C(=O)O$R^{12}$, —C(=O)N$R^{12}R^{13}$, —O—($CH_2CH_2$—O)$_{1-30}$—H, —O—($CH_2CH_2$—O)$_{1-30}$—$CH_3$, =O, —O$R^{12}$, —OC(=O)$R^{12}$, —OC(=O)O$R^{12}$, —OC(=O)N$R^{12}R^{13}$, —$NO_2$, —N$R^{12}R^{13}$, —$NR^{12}$—($CH_2$)$_{1-6}$—C(=O)$R^{13}$, —$NR^{12}$—($CH_2$)$_{1-6}$—C(=O)O$R^{13}$, —$NR^{14}$—($CH_2$)$_{1-6}$—C(=O)N$R^{12}R^{13}$, —$NR^{12}$C(=O)$R^{13}$, —$NR^{12}$C(=O)—O$R^{13}$, —$NR^{14}$C(=O)N$R^{12}R^{13}$, —$NR^{12}$S(=O)$_2R^{13}$, —S$R^{12}$, —S(=O)$R^{12}$, —S(=O)$_2R^{12}$, —S(=O)$_{20}R^{12}$, and —S(=O)$_2$N$R^{12}R^{13}$;

wherein $R^{12}$, $R^{13}$ and $R^{14}$ independently of one another mean —H;

—$C_1$-$C_6$-alkyl, linear or branched, saturated or unsaturated, unsubstituted or substituted with one, two, three or four substituents independently of one another selected from the group consisting of —F, —Cl, —Br, —I, —CN, =O, —OH, —$NH_2$, —NH—$C_1$-$C_6$-alkyl, —N($C_1$-$C_6$-alkyl)$_2$, —$C_1$-$C_6$-alkyl, —O—$C_1$-$C_6$-alkyl, —C(=O)OH, —C(=O)O$C_1$-$C_4$-alkyl, —C(=O)$NH_2$, —C(=O)NH—$C_1$-$C_6$-alkyl, —C(=O)N($C_1$-$C_6$-alkyl)$_2$, -S-$C_1$-$C_6$-alkyl, —S(=O)—$C_1$-$C_6$-alkyl and —S(=O)$_2$—$C_1$-$C_6$-alkyl;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, =O, —OH, —$NH_2$, —NH—$C_1$-$C_6$-alkyl, —N($C_1$-$C_6$-alkyl)$_2$, —$C_1$-$C_6$-alkyl, —O—$C_1$-$C_6$-alkyl, —C(=O)OH, —C(=O)O$C_1$-$C_4$-alkyl, —C(=O)$NH_2$, —C(=O)NH—$C_1$-$C_6$-alkyl, —C(=O)N($C_1$-$C_6$-alkyl)$_2$, -S-$C_1$-$C_6$-alkyl, —S(=O)—$C_1$-$C_6$-alkyl and —S(=O)$_2$—$C_1$-$C_6$-alkyl;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, =O, —OH, —$NH_2$, —NH—$C_1$-$C_6$-alkyl, —N($C_1$-$C_6$-alkyl)$_2$, —$C_1$-$C_6$-alkyl, —O—$C_1$-$C_6$-alkyl, —C(=O)OH, —C(=O)O$C_1$-$C_4$-alkyl, —C(=O)$NH_2$, —C(=O)NH—$C_1$-$C_6$-alkyl, —C(=O)N($C_1$-$C_6$-alkyl)$_2$, -S-$C_1$-$C_6$-alkyl, —S(=O)—$C_1$-$C_6$-alkyl and —S(=O)$_2$—$C_1$-$C_6$-alkyl;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —NH—$C_1$-$C_6$-alkyl, —N($C_1$-$C_6$-alkyl)$_2$, —$C_1$-$C_6$-alkyl, —O—$C_1$-$C_6$-alkyl, —C(=O)OH, —C(=O)O$C_1$-$C_4$-alkyl, —C(=O)$NH_2$, —C(=O)NH—$C_1$-$C_6$-alkyl, —C(=O)N($C_1$-$C_6$-alkyl)$_2$, -S-$C_1$-$C_6$-alkyl, —S(=O)—$C_1$-$C_6$-alkyl and —S(=O)$_2$—$C_1$-$C_6$-alkyl; or a 5-14-membered heteroaryl moiety, unsubstituted, mono- or polysubstituted; wherein said 5-14-membered heteroaryl moiety is optionally connected through -$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, -$NH_2$, —NH—$C_1$-$C_6$-alkyl, —N($C_1$-$C_6$-alkyl)$_2$, —$C_1$-$C_6$-alkyl, —O—$C_1$-$C_6$-alkyl, —C(=O)OH, —C(=O)O$C_1$-$C_4$-alkyl, —C(=O)$NH_2$, —C(=O)NH—$C_1$-$C_6$-alkyl, —C(=O)N($C_1$-$C_6$-alkyl)$_2$, -S—$C_1$-$C_6$-alkyl, —S(=O)—$C_1$-$C_6$-alkyl and —S(=O)$_2$—$C_1$-$C_6$-alkyl;

or $R^{12}$ and $R^{13}$ within -C(=O)N$R^{12}R^{13}$, —OC(=O)N$R^{12}R^{13}$, —N$R^{12}R^{13}$, —$NR^{14}$—($CH_2$)$_{1-6}$-C(=O)N$R^{12}R^{13}$, —$NR^{14}$C(=O)—N$R^{12}R^{13}$, or —S(=O)$_2$N$R^{12}R^{13}$ together with the nitrogen atom to which they are attached form a ring and mean —($CH_2$)$_{3-6}$—; —($CH_2$)$_2$—O—($CH_2$)$_2$—; or —($CH_2$)$_2$—$NR^B$—($CH_2$)$_2$—, wherein $R^B$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;
or a physiologically acceptable salt thereof.

2. The compound according to claim 1, wherein $R^6$, $R^7$, $R^8$, $R^9$, $R^{10}$, and $R^{11}$ independently of one another mean —H, —F, —OH, or —$C_1$-$C_6$-alkyl; or $R^6$ and $R^7$ together mean =O.

3. The compound according to claim 1, wherein
$R^1$ means —H; and $R^2$ means —$C_1$-$C_6$-alkyl, linear or branched, saturated or unsaturated, unsubstituted, mono- or polysubstituted with one, two, three or four substituents independently of one another selected from the group consisting of —F, —Cl, —Br, —I, —OH, —$OCH_3$, —CN and —$CO_2CH_3$;
$R^1$ means —$CH_3$; and $R^2$ means —$C_1$-$C_6$-alkyl, linear or branched, saturated or unsaturated, unsubstituted, mono- or polysubstituted with one, two, three or four substituents independently of one another selected from the group consisting of —F, —Cl, —Br, —I, —OH, —$OCH_3$, —CN and —$CO_2CH_3$;
$R^1$ means —H or —$CH_3$; and $R^2$ means a 3-12-membered cycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$;
$R^1$ means —H or —$CH_3$; and $R^2$ means a 3-12-membered cycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$; wherein said 3-12-membered cycloalkyl moiety is connected through —$CH_2$—, unsubstituted; or
$R^1$ and $R^2$ together with the nitrogen atom to which they are attached form a ring and mean —$(CH_2)_{3-6}$—.

4. The compound according to claim 1, wherein $R^3$ means -$C_1$-$C_6$-alkyl, linear or branched, saturated or unsaturated, unsubstituted, mono- or polysubstituted.

5. The compound according to claim 1, wherein $R^3$ means a 6-14-membered aryl moiety, unsubstituted, mono- or polysubstituted, optionally connected through —$C_1$-$C_6$-alkylene-, linear or branched, saturated or unsaturated, unsubstituted.

6. The compound according to claim 1, wherein $R^3$ means a 5-14-membered heteroaryl moiety, unsubstituted, mono- or polysubstituted.

7. The compound according to claim 1, wherein $R^3$ means -phenyl, unsubstituted, mono-, di- or trisubstituted with —F, —Cl, —Br, —$C_1$-$C_4$-alkyl, —$CF_3$, —$CHF_2$, —$CH_2F$, —CN, —OH, —$OC_1$-$C_4$-alkyl, —$OCF_3$ or —$OCH_2OCH_3$; or
-pyridinyl or thienyl, in each case unsubstituted, mono-, di- or trisubstituted with —F, —Cl, —Br, —$C_1$-$C_4$-alkyl, —$CF_3$, —$CHF_2$, —$CH_2F$, —CN, —OH, —$OC_1$-$C_4$-alkyl, —$OCF_3$ or —$OCH_2OCH_3$.

8. The compound according to according to claim 1, wherein $R^4$ means H;
—$C_1$-$C_6$-alkyl, linear or branched, saturated or unsaturated, unsubstituted, mono- or polysubstituted;
a 3-12-membered cycloalkyl moiety, saturated or unsaturated, unsubstituted, mono- or polysubstituted; wherein the 3-12-membered cycloalkyl moiety is connected through —$C_1$-$C_6$-alkylene-, linear or branched, saturated or unsaturated, unsubstituted, mono- or polysubstituted; or
a 3-12-membered heterocycloalkyl moiety, saturated or unsaturated, unsubstituted, mono- or polysubstituted; wherein said 3-12-membered heterocycloalkyl moiety is connected through —$C_1$-$C_6$-alkylene-, linear or branched, saturated or unsaturated, unsubstituted, mono- or polysubstituted.

9. The compound according to according to claim 1, wherein $R^4$ means a 6-14-membered aryl moiety, unsubstituted, mono- or polysubstituted; wherein said 6-14-membered aryl moiety is connected through —$C_1$-$C_6$-alkylene-, linear or branched, saturated or unsaturated, unsubstituted, mono- or polysubstituted; or
a 5-14-membered heteroaryl moiety, unsubstituted, mono- or polysubstituted; wherein said 5-14-membered heteroaryl moiety is connected through —$C_1$-$C_6$-alkylene-, linear or branched, saturated or unsaturated, unsubstituted, mono- or polysubstituted.

10. The compound according to claim 1, wherein, $R^5$ means -H.

11. The compound according to claim 1, wherein $R^5$ means -$C_1$-$C_6$-alkyl, linear or branched, saturated or unsaturated, unsubstituted or substituted with one, two, three or four substituents independently of one another selected from the group consisting of —F, —Cl, —Br, —I, —CN, —OH, —O—$C_1$-$C_4$-alkyl, —O—$(CH_2CH_2$—$O)_{1-30}$—H, —O—$(CH_2CH_2$—$O)_{1-30}$—$CH_3$, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2$$C_1$-$C_4$-alkyl.

12. The compound according to claim 1, wherein $R^5$ means -$C_1$-$C_6$-alkyl, linear or branched, saturated or unsaturated, monosubstituted with a 3-12-membered heterocycloalkyl moiety, saturated or unsaturated, unsubstituted, mono- or polysubstituted; or $R^5$ means a 3-12-membered heterocycloalkyl moiety, wherein said 3-12-membered heterocycloalkyl moiety is optionally connected through —C=O—.

13. The compound according to claim 1, wherein $R^5$ means a 3-12-membered cycloalkyl moiety, saturated or unsaturated, unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —$C_1$-$C_4$-alkyl-OH, —O—$(CH_2CH_2$-$O)_{1-30}$—H, —O—$(CH_2CH_2$—$O)_{1-30}$—$CH_3$, —C(=O)OH, —C(=O)$C_1$-$C_4$-alkyl, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —$NH_2$, -NH$C_1$-$C_4$-alkyl, N($C_1$-$C_4$-alkyl)$_2$, —NHC(=O)—$C_1C_4$-alkyl, —N($C_1$-$C_4$-alkyl)C(=O)$C_1$-$C_4$-alkyl, —S(=O)$C_1$-$C_4$-alkyl and —S(=O)$_2$$C_1$-$C_4$-alkyl; wherein said 3-12-membered cycloalkyl moiety is optionally connected through —$C_1$-$C_6$-alkylene-, linear or branched, saturated or unsaturated, unsubstituted.

14. The compound according to claim 1, wherein $R^5$ means a 3-12-membered heterocycloalkyl moiety, saturated or unsaturated, unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —$C_1$-$C_4$-alkyl-OH, —O—$(CH_2CH_2$—$O)_{1-30}$—H, —O—$(CH_2CH_2$—$O)_{1-30}$—$CH_3$, —C(=O)OH, —C(=O)$C_1$-$C_4$-alkyl, —C(=O)

$OC_1$-$C_4$-alkyl, —C(=O)$NH_2$, —C(=O)$NHC_1$-$C_4$-alkyl, —C(=O)N($C_1$-$C_4$-alkyl)$_2$, —$NH_2$, —$NHC_1$-$C_4$-alkyl, N($C_1$-$C_4$-alkyl)$_2$, —NHC(=O)—$C_1C_4$-alkyl, -N($C_1$-$C_4$-alkyl)C(=O)$C_1$-$C_4$-alkyl, —S(=O)$C_1$-$C_4$-alkyl and —S(=O)$_2C_1$-$C_4$-alkyl; wherein said 3-12-membered heterocycloalkyl moiety is optionally connected through —$C_1$-$C_6$-alkylene-, linear or branched, saturated or unsaturated, unsubstituted.

15. The compound according to claim 1, wherein $R^5$ means -phenyl, unsubstituted, mono- or polysubstituted; wherein said phenyl is optionally connected through —$C_1$-$C_6$-alkylene-, linear or branched, saturated or unsaturated, unsubstituted, mono- or polysubstituted; or wherein said phenyl is optionally connected through —C(=O)—, —C(=O)O—, —C(=O)O—$CH_2$—, or —S(=O)$_2$—.

16. The compound according to claim 1, wherein $R^5$ means a bicyclic 9-10-membered heteroaryl moiety, unsubstituted, mono- or polysubstituted.

17. The compound according to claim 1, wherein $R^5$ has a meaning selected from the group consisting of:

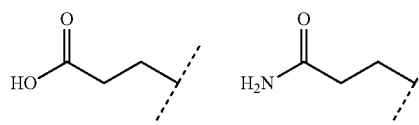

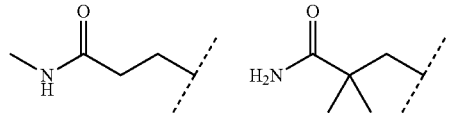

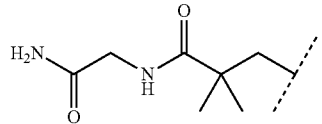

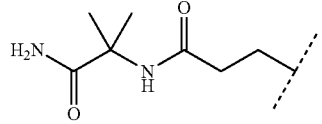

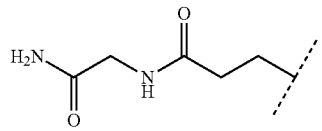

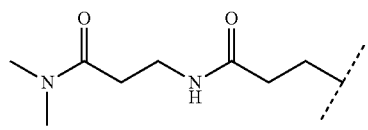

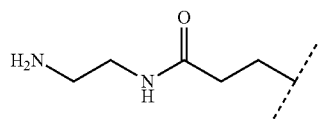

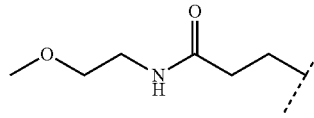

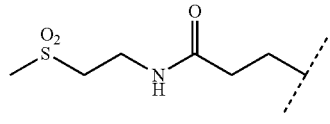

-continued

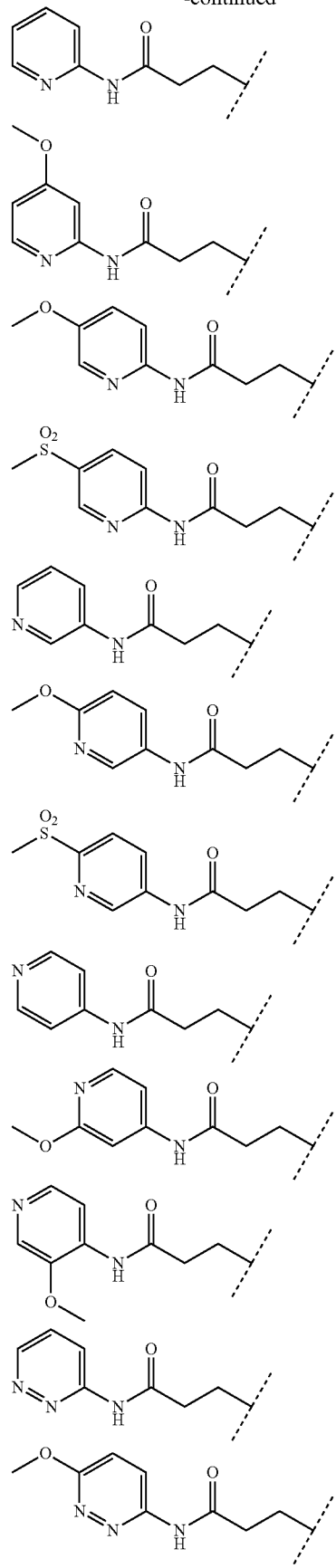

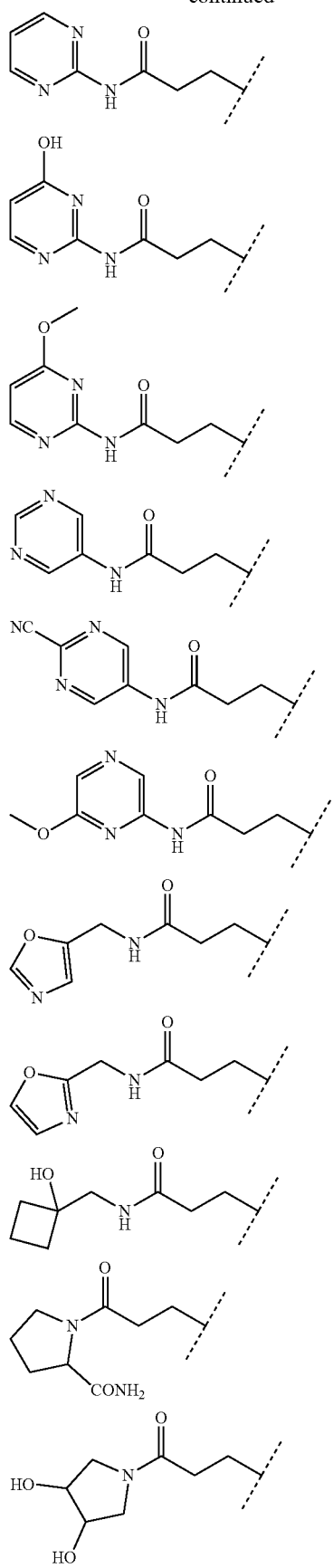
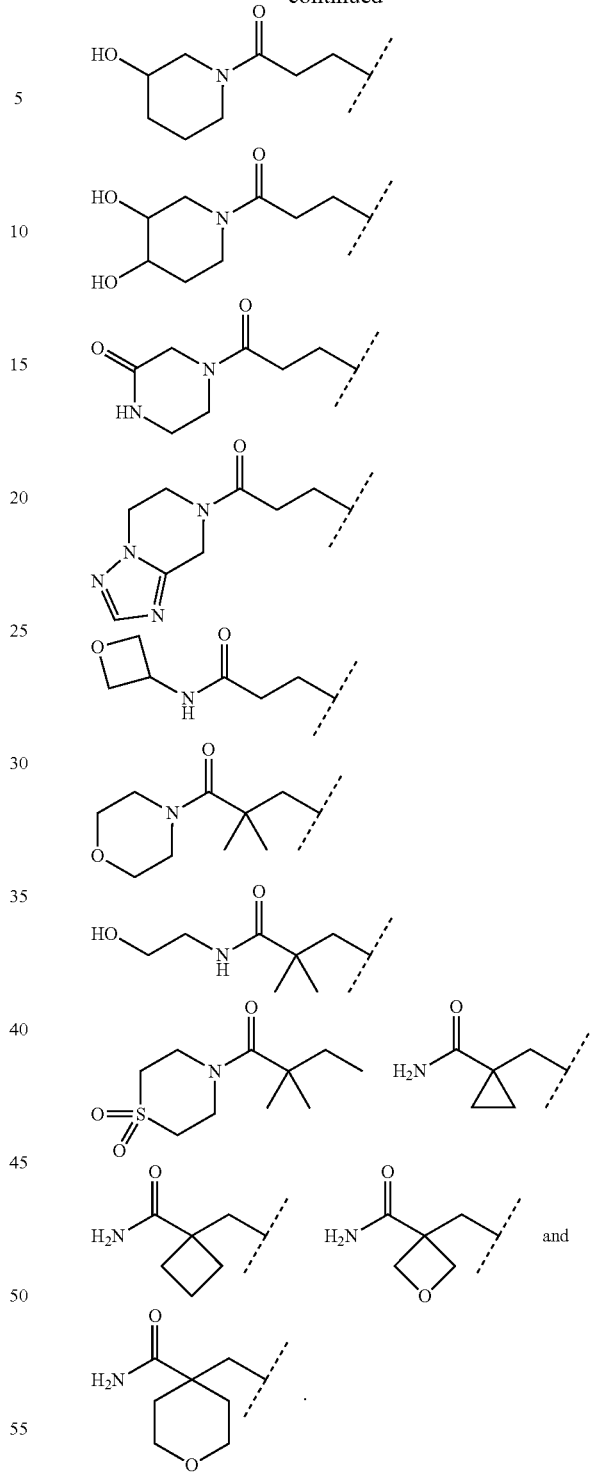

18. The compound according to claim 1, wherein
$R^1$ means —H or -CH$_3$;
$R^2$ means -C$_1$-C$_6$-alkyl, linear or branched, saturated, unsubstituted; -cyclopropyl; or -cyclopropylmethylene;
or $R^1$ and $R^2$ together with the nitrogen atom to which they are attached form a ring and mean -azetidine or -pyrrolidine;
$R^3$ means -phenyl, -thienyl or -pyridinyl, in each case unsubstituted or substituted with one, two, three or four substituents independently of one another selected from the group consisting of —F, —Cl, —Br, —CN, —C$_1$-C$_4$-alkyl, —CH$_3$, —CH$_2$CH$_3$, —CH$_2$F, —CHF$_2$, —CF$_3$, —OCF$_3$, —OH, —O—C$_1$-C$_4$-alkyl, —OCH$_3$, —C(=O)NH$_2$, C(=O)NHCH$_3$, —C(=O)N(CH$_3$)$_2$, —NH$_2$, -NHCH$_3$, —N(CH$_3$)$_2$, —NHC(=O)CH$_3$, —CH$_2$OH, SOCH$_3$ and SO$_2$CH$_3$; or R$^4$ means
- —H;
- —C$_1$-C$_6$-alkyl, linear or branched, saturated, unsubstituted or substituted with one, two, three or four substituents independently of one another selected from the group consisting of —F, —Cl, —Br, —I, —CN, —OH, =O, —S(=O)$_2$—C$_1$-C$_4$-alkyl and —O—C$_1$-C$_4$-alkyl;
- 3-6-membered cycloalkyl, unsubstituted or substituted with one, two, three or four substituents independently of one another selected from the group consisting of —F, —Cl, —Br, —I, —CN, —OH, and —O—C$_1$-C$_4$-alkyl, wherein said 3-6-membered cycloalkyl is connected through —C$_1$-C$_6$-alkylene;
- 3-12-membered heterocycloalkyl, saturated or unsaturated, unsubstituted or substituted with one, two, three or four substituents independently of one another selected from the group consisting of —F, —Cl, —Br, —I, —CN, —OH, and —O—C$_1$-C$_4$-alkyl; wherein said 3-12-membered heterocycloalkyl is optionally connected through —C$_1$-C$_6$-alkylene-, unsubstituted or substituted with =O;
- 6-14-membered aryl, unsubstituted or substituted with one, two, three or four substituents independently of one another selected from the group consisting of —F, —Cl, —Br, —I, —CN, —OH, and —O—C$_1$-C$_4$-alkyl; wherein said 6-14-membered aryl is optionally connected through —C$_1$-C$_6$-alkylene- or —S(=O)$_2$—;

R$^5$ means
- —H;
- —C$_1$-C$_6$-alkyl, linear or branched, saturated or unsaturated, unsubstituted or substituted with one, two, three or four substituents independently of one another selected from the group consisting of —F, —Cl, —Br, —I, —CN, =O, —OH, —O—C$_1$-C$_4$-alkyl, —O—(CH$_2$CH$_2$—O)$_{1-30}$—H, —O—(CH$_2$CH$_2$—O)$_{1-30}$—CH$_3$, —C(=O)OH, —C(=O)C$_1$-C$_4$-alkyl, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —(C=O)-heterocycloalkyl, —S(=O)C$_1$-C$_4$-alkyl, —S(=O)$_2$C$_1$-C$_4$-alkyl, —NH$_2$, —NH—C$_1$-C$_4$-alkyl, —N(C$_1$-C$_4$-alkyl)$_2$, —NHC(=O)—C$_1$-C$_4$-alkyl, —NH—S(=O)$_2$C$_1$-C$_4$-alkyl;
- 3-12-membered heterocycloalkyl, saturated or unsaturated, unsubstituted or substituted with one, two, three or four substituents independently of one another selected from the group consisting of —F, —Cl, —Br, —I, —CN, =O, —OH, —C$_1$-C$_4$-alkyl, —NH$_2$, —NH—C$_1$-C$_4$-alkyl, —N(C$_1$-C$_4$-alkyl)$_2$, —NHC(=O)—C$_1$-C$_4$-alkyl, —NHS(=O)$_2$—C$_1$-C$_4$-alkyl, —O—C$_1$-C$_4$-alkyl, —O—(CH$_2$CH$_2$—O)$_{1-30}$—H, —O—(CH$_2$CH$_2$—O)$_{1-30}$—CH$_3$, —C(=O)OH, —C(=O)C$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl, —S(=O)$_2$C$_1$-C$_4$-alkyl, -phenyl, —C(=O)-phenyl, —C(=O)-pyridyl, -pyridyl, -pyrimidinyl, and -pyridazinyl; wherein said 3-12-membered heterocycloalkyl moiety is optionally connected through —C$_1$-C$_6$-alkylene-, linear or branched, saturated or unsaturated, unsubstituted; or wherein said 3-12-membered heterocycloalkyl moiety is optionally connected through —C=O— or -CH$_2$-C=O—;
- -1,2-benzodioxole, -pyrazinyl, -pyridazinyl, -pyridinyl, -pyrimidinyl, -thienyl, -imidazolyl,
- -benzimidazolyl, -thiazolyl, -1,3,4-thiadiazolyl, -benzothiazolyl, -oxazolyl,
- -benzoxazolyl, -pyrazolyl,
- -quinolinyl, -isoquinolinyl, -quinazolinyl, -indolyl, -indolinyl,
- -benzo[c][1,2,5]oxadiazolyl,
- -imidazo[1,2-a]pyrazinyl, or -1H-pyrrolo[2,3-b]pyridinyl, in each case unsubstituted, mono- or polysubstituted;

and

R$^6$, R$^7$, R$^8$, R$^9$, R$^{10}$, and R$^{11}$ mean —H; or R$^6$ and R$^7$ together mean =O and R$^8$, R$^9$, R$^{10}$, and R$^{11}$ mean —H.

19. The compound according to claim 1, which is selected from the group consisting of 2-(2-(dimethylamino)-6-oxo-2-phenyl-5,7-diazaspiro[3.4]octan-7-yl)acetamide
2-(dimethylamino)-7-(2-(1,1-dioxidothiomorpholino)-2-oxoethyl)-2-phenyl-5,7-diazaspiro-[3.4]-octan-6-one
5-(2-(dimethylamino)-6-oxo-2-phenyl-5,7-diazaspiro[3.4]octan-7-yl)-4-methoxy-pyrimidine-2-carbonitrile
5-(cyclobutylmethyl)-2-(dimethylamino)-7-(2-(1,1-dioxidothiomorpholino)-2-oxo-ethyl)-2-phenyl-5,7-diazaspiro[3.4]octan-6-one
2-(5-(cyclobutylmethyl)-2-(dimethylamino)-6-oxo-2-phenyl-5,7-diazaspiro[3.4]octan-7-yl)acetamide
5-(5-(cyclobutylmethyl)-2-(dimethylamino)-6-oxo-2-phenyl-5,7-diazaspiro[3.4]octan-7-yl)-4-methoxypyrimidine-2-carbonitrile
2-(dimethylamino)-7-(4-methyl-2-morpholin-4-ylpyrimidin-5-yl)-2-phenyl-5,7-diazaspiro[3.4]octan-6-one
7-(6-(azetidin-1-yl)-4-methylpyridin-3-yl)-2-(dimethylamino)-2-phenyl-5,7-diazaspiro[3.4]octan-6-one
5-(2-(dimethylamino)-2-(3-fluorophenyl)-6-oxo-5,7-diazaspiro[3.4]octan-7-yl)-4-methylpicolino-nitrile
5-(5-(cyclopropylmethyl)-2-(dimethylamino)-2-(3-fluorophenyl)-6-oxo-5,7-diazaspiro[3.4]octan-7-yl)-4-methyl-picolinonitrile
6-(5-(cyclopropylmethyl)-2-(dimethylamino)-2-(3-fluorophenyl)-6-oxo-5,7-diazaspiro[3.4]octan-7-yl)-5-methyl-nicotinonitrile
2-(dimethylamino)-2-(3-fluorophenyl)-7-(5-(trifluoromethoxy)pyridin-2-yl)-5,7-diazaspiro[3.4]-octan-6-one
5-(cyclopropylmethyl)-2-(dimethylamino)-2-(3-fluorophenyl)-7-(5-(trifluoromethoxy)pyridin-2-yl)-5,7-diazaspiro[3.4]octan-6-one 2-(dimethylamino)-7-(4-methyl-6-morpholinopyridin-3-yl)-2-phenyl-5,7-diazaspiro[3.4]octan-6-one
2-(dimethylamino)-7-(6-(2-hydroxypropan-2-yl)-4-methylpyridin-3-yl)-2-phenyl-5,7-diazaspiro-[3.4]octan-6-one
2-(dimethylamino)-7-(4-(2-hydroxypropan-2-yl)-2-methylphenyl)-2-phenyl-5,7-diazaspiro[3.4]-octan-6-one
7-(6-(difluoromethyl)-4-methylpyridin-3-yl)-2-(dimethylamino)-2-(3-fluorophenyl)-5,7-diazaspiro-[3.4]octan-6-one
2-(dimethylamino)-5-((3-fluorooxetan-3-yl)methyl)-2-(3-fluorophenyl)-7-(5-(trifluoromethoxy)-pyridin-2-yl)-5,7-diazaspiro[3.4]octan-6-one
5-(cyclopropylmethyl)-7-(6-(difluoromethyl)-4-methylpyridin-3-yl)-2-(dimethylamino)-2-(3-fluoro-phenyl)-5,7-diazaspiro[3.4]octan-6-one
2-(dimethylamino)-7-(2-morpholinopyrimidin-5-yl)-2-phenyl-5,7-diazaspiro[3.4]octan-6-one
2-(dimethylamino)-5-((1-fluorocyclopropyl)methyl)-2-(3-fluorophenyl)-7-(5-(trifluoromethoxy)-pyridin-2-yl)-5,7-diazaspiro[3.4]octan-6-one
2-(dimethylamino)-2-(3-fluorophenyl)-5-((1-hydroxycyclobutyl)methyl)-7-(5-(trifluoromethoxy)-pyridin-2-yl)-5,7-diazaspiro[3.4]octan-6-one
5-(cyclopropylmethyl)-2-(dimethylamino)-2-(3-fluorophenyl)-7-(4-(2-hydroxypropan-2-yl)phenyl)-5,7-diazaspiro[3.4]octan-6-one
2-(dimethylamino)-5-((3-fluorooxetan-3-yl)methyl)-2-phenyl-7-(5-(trifluoromethoxy)pyridin-2-yl)-5,7-diazaspiro[3.4]octan-6-one
5-(cyclopropylmethyl)-2-(dimethylamino)-2-(3-fluorophenyl)-7-((6-(trifluoromethyl)pyridin-3-yl)methyl)-5,7-diazaspiro[3.4]octan-6-one
5-(cyclopropylmethyl)-2-(dimethylamino)-2-(3-fluorophenyl)-7-(2-(methylsulfonyl)ethyl)-5,7-diazaspiro[3.4]octan-6-one
5-(cyclopropylmethyl)-2-(dimethylamino)-2-phenyl-7-(5-(trifluoromethoxy)pyridin-2-yl)-5,7-diazaspiro[3.4]octan-6-one
5-(cyclopropylmethyl)-2-(dimethylamino)-7-((3-fluorooxetan-3-yl)methyl)-2-(3-fluorophenyl)-5,7-diazaspiro[3.4]octan-6-one
5-(cyclopropylmethyl)-7-(6-cyclopropylpyridin-3-yl)-2-(dimethylamino)-2-phenyl-5,7-diazaspiro-[3.4]octan-6-one
7-(6-cyclopropyl-4-methylpyridin-3-yl)-5-(cyclopropylmethyl)-2-(dimethylamino)-2-phenyl-5,7-diazaspiro[3.4]octan-6-one
7-(6-cyclopropyl-4-methylpyridin-3-yl)-2-(dimethylamino)-5-((3-fluorooxetan-3-yl)methyl)-2-phenyl-5,7-diazaspiro[3.4]octan-6-one
5-(cyclopropylmethyl)-2-(dimethylamino)-2-(3-fluorophenyl)-7-(2-methoxy-2-methylpropyl)-5,7-diazaspiro[3.4]octan-6-one
2-(dimethylamino)-2-phenyl-7-(2-pyridin-4-ylpyrimidin-5-yl)-5,7-diazaspiro[3.4]octan-6-one
5-(cyclopropylmethyl)-2-(dimethylamino)-2-phenyl-7-[5-(trifluoromethyl)pyridin-3-yl]-5,7-diazaspiro[3.4]octan-6-one
5-[5-(cyclopropylmethyl)-2-(dimethylamino)-6-oxo-2-phenyl-5,7-diazaspiro[3.4]octan-7-yl]-3-(trifluoromethyl)pyridine-2-carbonitrile
2-(dimethylamino)-2-(3-fluorophenyl)-7-(4-morpholinobenzyl)-5,7-diazaspiro[3.4]octan-6-one
5-(cyclopropylmethyl)-2-(dimethylamino)-2-(3-fluorophenyl)-7-[(1-hydroxycyclobutyl)methyl]-5,7-diazaspiro[3.4]octan-6-one
5-(cyclopropylmethyl)-2-(dimethylamino)-2-phenyl-7-(2-pyridin-4-ylpyrimidin-5-yl)-5,7-diaza-spiro[3.4]octan-6-one
3-(5-(cyclopropylmethyl)-2-(dimethylamino)-2-(3-fluorophenyl)-6-oxo-5,7-diazaspiro[3.4]octan-7-yl)propanenitrile
3-[5-(cyclopropylmethyl)-2-(dimethylamino)-6-oxo-2-phenyl-5,7-diazaspiro[3.4]octan-7-yl]-propanenitrile
5-(cyclopropylmethyl)-2-(dimethylamino)-7-[(1-hydroxycyclobutyl)methyl]-2-phenyl-5,7-diaza-spiro[3.4]octan-6-one
5-(cyclopropylmethyl)-2-(dimethylamino)-2-(3-fluorophenyl)-7-[2-(oxetan-3-yl)ethyl]-5,7-diaza-spiro[3.4]octan-6-one
cis-2-(2-(dimethylamino)-6-oxo-2-phenyl-5,7-diazaspiro[3.4]octan-7-yl)acetamide
cis-2-(dimethylamino)-7-(2-(1,1-dioxidothiomorpholino)-2-oxoethyl)-2-phenyl-5,7-diazaspiro-[3.4]octan-6-one
cis-5-(2-(dimethylamino)-6-oxo-2-phenyl-5,7-diazaspiro[3.4]octan-7-yl)-4-methoxy-pyrimidine-2-carbonitrile
trans-2-(dimethylamino)-7-(2-(1,1-dioxidothiomorpholino)-2-oxoethyl)-2-phenyl-5,7-diazaspiro-[3.4]octan-6-one
trans-5-(2-(dimethylamino)-6-oxo-2-phenyl-5,7-diazaspiro[3.4]octan-7-yl)-4-methoxypyrimidine-2-carbonitrile
cis-5-(cyclobutylmethyl)-2-(dimethylamino)-7-(2-(1,1-dioxidothiomorpholino)-2-oxo-ethyl)-2-phenyl-5,7-diazaspiro[3.4]octan-6-one
trans-5-(cyclobutylmethyl)-2-(dimethylamino)-7-(2-(1,1-dioxidothiomorpholino)-2-oxoethyl)-2-phenyl-5,7-diazaspiro[3.4]octan-6-one
cis-2-(5-(cyclobutylmethyl)-2-(dimethylamino)-6-oxo-2-phenyl-5,7-diazaspiro[3.4]-octan-7-yl-)acetamide
trans-2-(5-(cyclobutylmethyl)-2-(dimethylamino)-6-oxo-2-phenyl-5,7-diazaspiro[3.4]-octan-7-yl)-acetamide
cis-5-(5-(cyclobutylmethyl)-2-(dimethylamino)-6-oxo-2-phenyl-5,7-diazaspiro[3.4]-octan-7-yl)-4-methoxypyrimidine-2-carbonitrile
trans-5-(5-(cyclobutylmethyl)-2-(dimethylamino)-6-oxo-2-phenyl-5,7-diazaspiro[3.4]-octan-7-yl)-4-methoxypyrimidine-2-carbonitrile cis-2-(dimethylamino)-7-(4-methyl-2-morpholin-4-ylpyrimidin-5-yl)-2-phenyl-5,7-diazaspiro-[3.4]octan-6-one
cis-7-(6-(azetidin-1-yl)-4-methylpyridin-3-yl)-2-(dimethylamino)-2-phenyl-5,7-diazaspiro[3.4]octan-6-one
cis-5-(2-(dimethylamino)-2-(3-fluorophenyl)-6-oxo-5,7-diazaspiro[3.4]octan-7-yl)-4-methyl-picolinonitrile
cis-5-(5-(cyclopropylmethyl)-2-(dimethylamino)-2-(3-fluorophenyl)-6-oxo-5,7-diazaspiro[3.4]octan-7-yl)-4-methylpicolinonitrile
cis-6-(5-(cyclopropylmethyl)-2-(dimethylamino)-2-(3-fluorophenyl)-6-oxo-5,7-diazaspiro[3.4]octan-7-yl)-5-methylnicotinonitrile
cis-2-(dimethylamino)-2-(3-fluorophenyl)-7-(5-(trifluoromethoxy)pyridin-2-yl)-5,7-diazaspiro[3.4]-octan-6-one
cis-5-(cyclopropylmethyl)-2-(dimethylamino)-2-(3-fluorophenyl)-7-(5-(trifluoromethoxy)pyridin-2-yl)-5,7-diazaspiro[3.4]octan-6-one
cis-2-(dimethylamino)-7-(4-methyl-6-morpholinopyridin-3-yl)-2-phenyl-5,7-diazaspiro[3.4]octan-6-one
cis-2-(dimethylamino)-7-(6-(2-hydroxypropan-2-yl)-4-methylpyridin-3-yl)-2-phenyl-5,7-diazaspiro-[3.4]octan-6-one
cis-2-(dimethylamino)-7-(4-(2-hydroxypropan-2-yl)-2-methylphenyl)-2-phenyl-5,7-diazaspiro-[3.4]octan-6-one
cis-7-(6-(difluoromethyl)-4-methylpyridin-3-yl)-2-(dimethylamino)-2-(3-fluorophenyl)-5,7-diaza-spiro[3.4]octan-6-one
cis-2-(dimethylamino)-5-((3-fluorooxetan-3-yl)methyl)-2-(3-fluorophenyl)-7-(5-(trifluoromethoxy)-pyridin-2-yl)-5,7-diazaspiro[3.4]octan-6-one
cis-5-(cyclopropylmethyl)-7-(6-(difluoromethyl)-4-methylpyridin-3-yl)-2-(dimethylamino)-2-(3-fluorophenyl)-5,7-diazaspiro[3.4]octan-6-one
cis-2-(dimethylamino)-7-(2-morpholinopyrimidin-5-yl)-2-phenyl-5,7-diazaspiro[3.4]octan-6-one
cis-2-(dimethylamino)-5-((1-fluorocyclopropyl)methyl)-2-(3-fluorophenyl)-7-(5-(trifluoromethoxy)-pyridin-2-yl)-5,7-diazaspiro[3.4]octan-6-one
cis-2-(dimethylamino)-2-(3-fluorophenyl)-5-((1-hydroxycyclobutyl)methyl)-7-(5-(trifluoromethoxy)-pyridin-2-yl)-5,7-diazaspiro[3.4]octan-6-one
cis-5-(cyclopropylmethyl)-2-(dimethylamino)-2-(3-fluorophenyl)-7-(4-(2-hydroxypropan-2-yl)-phenyl)-5,7-diazaspiro[3.4]octan-6-one
cis-2-(dimethylamino)-5-((3-fluorooxetan-3-yl)methyl)-2-phenyl-7-(5-(trifluoromethoxy)pyridin-2-yl)-5,7-diazaspiro[3.4]octan-6-one
cis-5-(cyclopropylmethyl)-2-(dimethylamino)-2-(3-fluorophenyl)-7-((6-(trifluoromethyl)pyridin-3-yl)methyl)-5,7-diazaspiro[3.4]octan-6-one
cis-5-(cyclopropylmethyl)-2-(dimethylamino)-2-(3-fluorophenyl)-7-(2-(methylsulfonyl)ethyl)-5,7-diazaspiro[3.4]octan-6-one
cis-5-(cyclopropylmethyl)-2-(dimethylamino)-2-phenyl-7-(5-(trifluoromethoxy)pyridin-2-yl)-5,7-diazaspiro[3.4]octan-6-one
cis-5-(cyclopropylmethyl)-2-(dimethylamino)-7-((3-fluorooxetan-3-yl)methyl)-2-(3-fluorophenyl)-5,7-diazaspiro[3.4]octan-6-one
cis-5-(cyclopropylmethyl)-7-(6-cyclopropylpyridin-3-yl)-2-(dimethylamino)-2-phenyl-5,7-diaza-spiro[3.4]octan-6-one
cis-7-(6-cyclopropyl-4-methylpyridin-3-yl)-5-(cyclopropylmethyl)-2-(dimethylamino)-2-phenyl-5,7-diazaspiro[3.4]octan-6-one
cis-7-(6-cyclopropyl-4-methylpyridin-3-yl)-2-(dimethylamino)-5-((3-fluorooxetan-3-yl)methyl)-2-phenyl-5,7-diazaspiro[3.4]octan-6-one
cis-5-(cyclopropylmethyl)-2-(dimethylamino)-2-(3-fluorophenyl)-7-(2-methoxy-2-methylpropyl)-5,7-diazaspiro[3.4]octan-6-one
cis-2-(dimethylamino)-2-phenyl-7-(2-pyridin-4-ylpyrimidin-5-yl)-5,7-diazaspiro[3.4]octan-6-one
cis-5-(cyclopropylmethyl)-2-(dimethylamino)-2-phenyl-7-[5-(trifluoromethyl)pyridin-3-yl]-5,7-diazaspiro[3.4]octan-6-one
cis-5-[5-(cyclopropylmethyl)-2-(dimethylamino)-6-oxo-2-phenyl-5,7-diazaspiro[3.4]octan-7-yl]-3-(trifluoromethyl)pyridine-2-carbonitrile
cis-2-(dimethylamino)-2-(3-fluorophenyl)-7-(4-morpholinobenzyl)-5,7-diazaspiro[3.4]octan-6-one
cis-5-(cyclopropylmethyl)-2-(dimethylamino)-2-(3-fluorophenyl)-7-[(1-hydroxycyclobutyl)methyl]-5,7-diazaspiro[3.4]octan-6-one
cis-5-(cyclopropylmethyl)-2-(dimethylamino)-2-phenyl-7-(2-pyridin-4-ylpyrimidin-5-yl)-5,7-diazaspiro[3.4]octan-6-one
cis-3-(5-(cyclopropylmethyl)-2-(dimethylamino)-2-(3-fluorophenyl)-6-oxo-5,7-diazaspiro[3.4]octan-7-yl)propanenitrile
cis-3-[5-(cyclopropylmethyl)-2-(dimethylamino)-6-oxo-2-phenyl-5,7-diazaspiro[3.4]octan-7-yl]-propanenitrile
cis-5-(cyclopropylmethyl)-2-(dimethylamino)-7-[(1-hydroxycyclobutyl)methyl]-2-phenyl-5,7-diaza-spiro[3.4]octan-6-one -continued cis-5-(cyclopropylmethyl)-2-(dimethylamino)-2-(3-fluorophenyl)-7-[2-(oxetan-3-yl)ethyl]-5,7-diaza-spiro[3.4]octan-6-one or a physiologically acceptable salt thereof.

20. A medicament comprising a compound according to claim 1.

21. A method of treating pain in a subject in need thereof, said method comprising administering to said subject an effective amount therefor of at least one compound according to claim 1.

* * * * *